United States Patent
Piu et al.

(10) Patent No.: US 9,486,405 B2
(45) Date of Patent: Nov. 8, 2016

(54) METHODS FOR THE TREATMENT OF PEDIATRIC OTIC DISORDERS

(71) Applicant: Otonomy, Inc., San Diego, CA (US)

(72) Inventors: Fabrice Piu, San Diego, CA (US); Qiang Ye, San Diego, CA (US); Luis A. Dellamary, San Marcos, CA (US); Carl Lebel, Malibu, CA (US)

(73) Assignee: OTONOMY, INC., San Diego, CA (US)

( * ) Notice: Subject to any disclaimer, the term of this patent is extended or adjusted under 35 U.S.C. 154(b) by 0 days.

(21) Appl. No.: 14/469,408

(22) Filed: Aug. 26, 2014

(65) Prior Publication Data

US 2015/0290124 A1 Oct. 15, 2015

Related U.S. Application Data

(60) Provisional application No. 61/870,318, filed on Aug. 27, 2013, provisional application No. 61/914,904, filed on Dec. 11, 2013.

(51) Int. Cl.
| | | |
|---|---|---|
| A61K 31/496 | (2006.01) | |
| A61K 9/00 | (2006.01) | |
| A61K 47/10 | (2006.01) | |
| A61K 47/18 | (2006.01) | |

(52) U.S. Cl.
CPC ........... *A61K 9/0046* (2013.01); *A61K 9/0019* (2013.01); *A61K 31/496* (2013.01); *A61K 47/10* (2013.01); *A61K 47/18* (2013.01)

(58) Field of Classification Search
CPC .................................................. A61K 31/496
See application file for complete search history.

(56) References Cited

U.S. PATENT DOCUMENTS

| | | | |
|---|---|---|---|
| 4,188,373 A | 2/1980 | Krezanoski | |
| 4,478,822 A | 10/1984 | Haslam et al. | |
| 4,938,763 A | 7/1990 | Dunn et al. | |
| 4,968,507 A | 11/1990 | Zentner et al. | |
| 5,292,516 A | 3/1994 | Viegas et al. | |
| 5,324,519 A | 6/1994 | Dunn et al. | |
| 5,401,741 A | 3/1995 | Sato et al. | |
| 5,421,818 A | 6/1995 | Arenberg | |
| 5,474,529 A | 12/1995 | Arenberg | |
| 5,476,446 A | 12/1995 | Arenberg | |
| 5,503,848 A | 4/1996 | Perbellini et al. | |
| 5,702,716 A | 12/1997 | Dunn et al. | |
| 5,744,153 A | 4/1998 | Yewey et al. | |
| 5,861,174 A | 1/1999 | Stratton et al. | |
| 5,990,194 A | 11/1999 | Dunn et al. | |
| 6,004,573 A | 12/1999 | Rathi et al. | |
| 6,045,528 A | 4/2000 | Arenberg et al. | |
| 6,117,949 A | 9/2000 | Rathi et al. | |
| 6,177,434 B1 | 1/2001 | Kopke et al. | |
| 6,201,065 B1 | 3/2001 | Pathak et al. | |
| 6,201,072 B1 | 3/2001 | Rathi et al. | |
| 6,239,113 B1 | 5/2001 | Dawson et al. | |
| 6,284,804 B1 | 9/2001 | Singh et al. | |
| 6,287,588 B1 | 9/2001 | Shih et al. | |
| 6,316,011 B1 | 11/2001 | Ron et al. | |
| 6,359,016 B2 | 3/2002 | Singh et al. | |
| 6,392,036 B1 | 5/2002 | Karlsson et al. | |
| 6,488,952 B1 | 12/2002 | Kennedy et al. | |
| 6,509,327 B1 | 1/2003 | Cagle et al. | |
| 6,649,621 B2 | 11/2003 | Kopke et al. | |
| 6,740,664 B2 | 5/2004 | Cagle et al. | |
| 7,001,615 B1 | 2/2006 | Singh et al. | |
| 7,018,645 B1 | 3/2006 | Piao et al. | |
| 7,220,431 B2 | 5/2007 | Sawchuk et al. | |
| 7,524,834 B2 | 4/2009 | Karlsson et al. | |
| 8,390,018 B2 | 3/2013 | Jang | |
| 2001/0034339 A1 | 10/2001 | Singh et al. | |
| 2002/0076441 A1 | 6/2002 | Shih et al. | |
| 2002/0107238 A1 | 8/2002 | Bandyopadhyay et al. | |
| 2002/0169142 A1 | 11/2002 | Jafari et al. | |
| 2003/0092776 A1 | 5/2003 | Ron et al. | |
| 2003/0139382 A1 | 7/2003 | Wall et al. | |
| 2003/0229333 A1 | 12/2003 | Ashton | |
| 2004/0022853 A1 | 2/2004 | Ashton et al. | |
| 2004/0082509 A1 | 4/2004 | Bonny | |
| 2004/0101506 A1 | 5/2004 | Fust | |
| 2004/0101560 A1 | 5/2004 | Sawchuk et al. | |
| 2004/0204471 A1 | 10/2004 | Seibert | |
| 2005/0147585 A1 | 7/2005 | Schwarz | |
| 2005/0214338 A1 | 9/2005 | Guitton et al. | |

(Continued)

FOREIGN PATENT DOCUMENTS

| | | |
|---|---|---|
| CN | 101664381 | 3/2010 |
| EP | 0551626 | 7/1993 |

(Continued)

OTHER PUBLICATIONS

Khoo, X., et al. "Formulations for trans-tympanic antibiotic delivery." Biomaterials. (2013), vol. 34, pp. 1281-1288.*
Ahn et al. Lipoic acid rescues DBA mice from early-onset age-related hearing impairment. Neuroreport 19(13):1265-9. 2008.
Arnold et al. Novel slow- and fast-type drug release round-window microimplants for local drug application to the cochlea: an experimental study in guinea pigs. Audiol Neurootol 10(1):53-63. 2005.
Auris Medical. press release reporting initiating of phase I/II clinical trial with AM-101. Feb. 22, 2007.
Auris Medical. press release reporting results of phase I/II clinical trial with AM-111. Jun. 21, 2006.
Battaglia et al. Combination therapy (intratympanic dexamethasone + high-dose prednisone taper) for the treatment of idiopathic sudden sensorineural hearing loss. Otol Neurotol 29(4):453-60. 2008.
Bird et al. Intratympanic versus intravenous delivery of methylprednisolone to cochlear perilymph. Otology & Neurotology 28(8):1124-1130. 2007.
Campbell et al. Oral-D-methionine (MRX-1024) significantly protects against cisplatininduced hearing loss: a phase II study in humans. Abst 32nd Ann MidWinter Res Meeting. ARO Abstracts 32:7. Feb 14-19, 2009.
Chang et al. Prolonged antifungal effects of clotrimazole-containing mucoadhesive thermosensitive gels on vaginitis. J of Controlled Release. 82:39-50 (2002).

(Continued)

*Primary Examiner* — Noble Jarrell
*Assistant Examiner* — John S Kenyon
(74) *Attorney, Agent, or Firm* — Wilson, Sonsini, Goodrich & Rosati

(57) ABSTRACT

Disclosed herein are methods for the treatment of pediatric otic diseases or conditions with antimicrobial agent compositions and formulations administered locally to an individual afflicted with an otic disease or condition, through direct application of these compositions and formulations onto or via perfusion into the targeted auris structure(s).

18 Claims, 20 Drawing Sheets

(56) References Cited

U.S. PATENT DOCUMENTS

| | | |
|---|---|---|
| 2005/0287200 A1 | 12/2005 | Murthy |
| 2006/0013858 A1 | 1/2006 | Trune |
| 2006/0034889 A1 | 2/2006 | Jo et al. |
| 2006/0046970 A1 | 3/2006 | Bowman et al. |
| 2006/0063802 A1 | 3/2006 | Guitton et al. |
| 2006/0257488 A1 | 11/2006 | Hubbard |
| 2006/0264897 A1 | 11/2006 | Lobl et al. |
| 2006/0269602 A1 | 11/2006 | Dasch et al. |
| 2007/0048338 A1 | 3/2007 | Ladd |
| 2007/0110788 A1 | 5/2007 | Hissong et al. |
| 2007/0167918 A1 | 7/2007 | Reed et al. |
| 2007/0178051 A1 | 8/2007 | Pruitt et al. |
| 2008/0124385 A1 | 5/2008 | Campbell |
| 2008/0181952 A1 | 7/2008 | Vogel et al. |
| 2008/0318918 A1 | 12/2008 | Campbell et al. |
| 2009/0093449 A1 | 4/2009 | Bowman et al. |
| 2009/0156566 A1 | 6/2009 | Wall et al. |
| 2009/0246255 A1 | 10/2009 | Meyer |
| 2009/0297533 A1 | 12/2009 | Lichter et al. |
| 2009/0306225 A1 | 12/2009 | Lichter et al. |
| 2009/0324552 A1 | 12/2009 | Lichter et al. |
| 2009/0325938 A1 | 12/2009 | Lichter et al. |
| 2010/0004225 A1 | 1/2010 | Lichter et al. |
| 2010/0009952 A1 | 1/2010 | Lichter et al. |
| 2010/0015228 A1 | 1/2010 | Lichter et al. |
| 2010/0015263 A1 | 1/2010 | Lichter et al. |
| 2010/0016218 A1 | 1/2010 | Lichter et al. |
| 2010/0016450 A1 | 1/2010 | Lichter et al. |
| 2010/0021416 A1 | 1/2010 | Lichter et al. |
| 2010/0022661 A1 | 1/2010 | Lichter et al. |
| 2010/0036000 A1 | 2/2010 | Lichter et al. |
| 2010/0197800 A1 | 8/2010 | Friedman et al. |
| 2010/0273864 A1 | 10/2010 | Lichter et al. |
| 2011/0166060 A1 | 7/2011 | Simons et al. |
| 2012/0277199 A1 | 11/2012 | Ye et al. |
| 2013/0116210 A1 | 5/2013 | Lichter et al. |
| 2013/0216609 A1 | 8/2013 | Lichter et al. |
| 2015/0150793 A1 | 6/2015 | Lichter et al. |
| 2016/0038594 A1 | 2/2016 | Lichter et al. |

FOREIGN PATENT DOCUMENTS

| | | |
|---|---|---|
| EP | 2567710 | 3/2013 |
| JP | H01258620 A | 10/1989 |
| JP | 07-215877 | 8/1995 |
| JP | 2001-520188 | 4/1999 |
| JP | 2004-507450 | 10/2001 |
| JP | 2001526246 A | 12/2001 |
| JP | 2004-536836 | 1/2003 |
| JP | 2006509791 A | 3/2006 |
| JP | 2006-97031 | 4/2006 |
| JP | 2006-111585 | 4/2006 |
| WO | WO 97/38698 | 10/1997 |
| WO | WO 99/24051 | 5/1999 |
| WO | WO 99/32151 | 7/1999 |
| WO | WO 99/32152 | 7/1999 |
| WO | WO 00/07603 | 2/2000 |
| WO | WO 00/50005 | 8/2000 |
| WO | WO 02/056890 | 7/2002 |
| WO | WO 03/017990 | 3/2003 |
| WO | WO 03/034979 | 5/2003 |
| WO | WO 03/051375 | 6/2003 |
| WO | WO 03/071986 | 9/2003 |
| WO | WO 2004/050021 | 6/2004 |
| WO | WO-2006029074 A2 | 3/2006 |
| WO | WO 2006/099325 | 9/2006 |
| WO | WO 2006/102964 | 10/2006 |
| WO | WO 2007/031098 | 3/2007 |
| WO | WO 2007/031280 | 3/2007 |
| WO | WO 2007/037874 | 4/2007 |
| WO | WO 2007/037886 | 4/2007 |
| WO | WO 2007/038949 | 4/2007 |
| WO | WO 2008/001341 | 1/2008 |
| WO | WO 2008/073938 | 6/2008 |
| WO | WO 2008/076556 | 6/2008 |
| WO | WO 2009/132050 | 10/2009 |
| WO | WO 2010/011609 | 1/2010 |

OTHER PUBLICATIONS

Chen et al. Design and preparation of thermosensitive in situ gel of dexamethasone sodium phosphate. I Guangdong Coll Pharm 23(5):518-21. 2007 (English abstract).

Chen et al. Estrogen-related receptor beta/NR3B2 controls epithelial cell fate and endolymph production by the stria vascularis. Dev Cell 13(3):325-37. 2007.

Chen et al. Evaluation of thermosensitive in situ gel using dynamic theological experiment. Chin Pharm J 43(6):444-447. 2008 (English abstract).

Chen et al. In vivo distribution and pharmacokinetics of dexamethasone sodium phosphate thermosensitive in situ gel following intratympanic injection. Sichuan Da Xue Xue Bao Yi Xue Ban 37(3):456-9. 2006 (English translation).

Chen et al. Preparation and characterization of dexamethasone acetate-loaded solid lipid nanoparticles. Chinese J Pharm 39(4):261-264. 2008 (English abstract).

Chen et al. Study on dexamethasone thermosensitive in situ gel for treating deafness. Chin Pharm J 41(9):685-688. 2006 (English abstract).

Choi et al. A novel class of phosphonate nucleosides. 9-[(1-phosphonomethoxycyclopropyl)methyl]guanine as a potent and selective anti-HBV agent. J Med Chem. May 20, 2004 (11):2864-2869.

Choi et al. Biological roles of lysophospholipid receptors revealed by genetic null mice: an update. Biochim Biophys Acta. Sep. 2008 1781(9):531-539.

Choi et al. Effect of additives on the physicochemical properties of liquid suppository bases. International Journal of Pharmaceutics. 1999. 190(1):13-19.

Choi et al. Enhanced production of insulin-like growth factor I fusion protein in *Escherichia coli* by coexpression of the down-regulated genes identified by transcriptome profiling. Applied and Environmental Microbiology. (2003) 69(8):4737-4742.

Choi et al. Regulation of keratin 19 gene expression by estrogen in human breast cancer cells and identification of the estrogen responsive gene region. Mol Cell Endocrinol 164(1-2):225-237. 2000.

Choi et al. Synthesis and antiviral activity of novel exomethylene cyclopropyl nucleosides. Nucleosides Nucleotides Nucleic Acids. Apr.-Jul. 2001 20(4-7):1059-1062.

Choi et al. The design and evaluation of heparin-binding foldamers. Angew Chem Int Ed Engl. 44(41):6685-6689. 2005.

Choi et al. Use of combinatorial genetic libraries to humanize N-linked glycosylation in the yeast *Pichia pastoris*. PNAS USA 100(9):5022-5027. 2003.

Ciprodex. product label. 2009.

Database WPI. Section Ch. Week 201029 Thomson Scientific. London. Preparation of Gelatin Sustained-release Composition for Treating Mastitis of Milk Cow Comprises Spraying Aqueous Solution of Ciprofloxacin and Chitosan Film Polymer to try and Distributing into Aqueous Solution of Poloxamer. download Feb. 5, 2014, 2 pages.

Dellamary et al. Assessing and optimizing osmolality of poloxamer 407 hydrogel formulations for sustained inner ear drug delivery. Abstract. 2010 AAPS National Biotechnology Conference in San Francisco.

Dellamary et al. Assessing and optimizing osmolality of poloxamer 407 hydrogel formulations for sustained inner ear drug delivery. Poster. 2010 AAPS National Biotechnology Conference in San Francisco.

Dellamary et al. Development of poloxamer hydrogel formulations for sustained inner ear drug delivery. Abstract. 2010 AAPS National Biotechnology Conference in San Francisco.

Dellamary et al. Development of poloxamer hydrogel formulations for sustained inner ear drug delivery. Poster. 2010 AAPS National Biotechnology Conference in San Francisco, 2010.

(56) References Cited

OTHER PUBLICATIONS

Dellamary et al. Novel poloxamer hydrogel formulations for sustained drug delivery to the middle ear. Abstract. 2010 AAPS Annual Meeting in New Orleans. Nov. 14-Nov. 18, 2010.
Dellamary et al. Novel poloxamer hydrogel formulations for sustained inner ear drug delivery. Poster. Controlled Release Society 37th Annual Meeting and Exposition in Portland. Jul. 10-14, 2010.
Dellamary et al. Sustained drug delivery to the middle ear via a novel poloxamer hydrogel formulation. Poster. 2010 AAPS Annual Meeting in New Orleans. Nov. 14-Nov. 18, 2010.
Dellamary et al. Novel poloxamer hydrogel formulations for sustained inner ear drug delivery . Abstract, Controlled Release Society 37th Annual Meeting and Exposition in Portland Jul. 10-14, 2010.
Derin et al. The effects of L-carnitine on presbyacusis in the rat model. Clin Otolaryngol Allied Sci 29(3):238-41. 2004.
Dourmishev et al. Waardenburg syndrome. Intl J Dermatol 38:656-663 (1999).
Elgen. Remington's Pharmaceuticals Sciences. 1985. 17th ed. pp. 1836-1837.
Endo et al. Novel strategy for treatment of inner ears using a biodegradable gel. Laryngoscope 115(11):2016-20. 2005.
EP 09800852.7 Examination Report dated Jul. 24, 2013.
EP 09800852.7 Search Report dated Nov. 26, 2012.
EP10825524.1 European Search Report dated Feb. 5, 2014.
Feng et al. In vitro and in vivo biodegradation of sustained-release vehicle poloxamer 407 in situ gel. Lin Chung Er Bi Yan Hou Tou Jing Wai Ke Za Zhi 22(1):28-31. 2008 (English translation).
Feng et al. In vitro and in vivo biodegradation of sustained-release vehicle polozamer 407 in situ gel. Zhonghua Yi Xue Za Zhi, Aug. 28, 2007 87(32):2289-91 (English Abstract and Translation).
Feng et al. Effect of poloxamer 407 on the middle ear and inner ear after regional perfusion in guinea pigs. Zhonghua Er Bi Yan Hou Tou Jing Wai Ke Za Zhi 42(6):443-6, 2007 (English translation).
Fernandez et al. Self-curing controlled release systems for steroids. Application of prednisolone-based polymeric systems to ear diseases. Biomaterials 26(16):3311-8. 2005.
Friedman et al. GRM7 variants confer susceptibility to age-related hearing impairment. Hum Mol Genet 18(4):785-96. 2009.
García-Berrocal et al. Does the serological study for viral infection in autoimmune inner ear disease make sense? O.R.L. (2008) 70:16-20.
Garduno-Anaya et al. Dexamethasone inner ear perfusion by intratympanic injection in unilateral Ménierè's disease: a two-year prospective, placebo-controlled, double-blind, randomized trial. Otolaryngol Head Neck Surg 133(2):285-94. 2005.
GB0823378.5 combined search and examination report dated Feb. 27, 2009.
GB0823378.5 examination report dated Oct. 23, 2009.
GB0907065.7 combined search and examination report dated Nov. 16, 2009.
GB0912650.9 combined search and examination report dated Oct. 23, 2009.
Gubbels et al. Functional auditory hair cells produced in the mammalian cochlea by in utero gene transfer. Nature 455(7212):537-41. 2008.
Guyot et al. Intratympanic application of an antiviral agent for the treatment of Ménière's disease. ORL (2008) 70:21-27.
Hall et al. Anti-Pneumocystis Activities of Aromatic Diamidoxine Prodrugs. Antimicrobial Agents & Chemotherapy, 1998, American Society for Microbiology 42(4):666-674 (1998).
Hargunani et al. Intratympanic injection of dexamethasone: time course of inner ear distribution and conversion to its active form. Otol Neurotol 27(4):564-9. 2006.
Harris et al. Prevention of noise-induced hearing loss with Src-PTK inhibitors. Hear Res 208(1-2):14-25. 2005.
Harris et al. Treatment of corticosteroid-responsive autoimmune inner ear disease with methotrexate: a randomized controlled trial. JAMA 290(14):1875-83. 2003.
Harris. Immunology of the inner ear: response of the inner ear to antigen challenge. Otorhinolaryngology Head and Neck Surgery. (1983) 91:18-32.
Hill et al. Cisplatin-induced ototoxicity: effect of intratympanic dexamethasone injections. Otol Neurotol 29:1005-11. 2008.
Hoffer et al. Transtympanic management of tinnitus. Otolaryngol Clin North Am 36(2):353-8. 2003.
Hoshino et al. The non-steroidal anti-inflammatory drugs protect mouse cochlea against acoustic injury. Tohoku J Exp Med 216(1):53-9. 2008.
http://medical-dictionary.thefreedictionary.com/glucocorticoid.
http://www.hearinglossweb.com/Medical/cures/instr.htm.
Inaoka et al. Local application of hepatocyte growth factor using gelatin hydrogels attenuates noise-induced bearing loss in guinea pigs. Acta Otolaryngol 129(4):453-7. 2009.
Jeong et al. Biodegradable block copolymers as injectable drug-delivery systems. Nature (1997) 388:860-862.
Jeong et al. Drug release from biodegradable injectable thermosensitive hydrogel of PEG-PLGA-PEG triblock copolymers. J. Control. Release (2000) 63:155-163.
Jeong et al. Thermosensitive sol-gel reversible hydrogels. Adv. Drug Delivery Rev. (2002) 54:37-51.
Jia et al. Intratympanic dexamethasone for refractory sudden deafness. Lin Chung Er Bi Yan Hou Tou Jing Wai Ke Za Zhi 22(7):309-11. 2008 (English translation).
Karolewicz et al. Thermosensitive polymers in drug form technology II. Possibilities of use of thermosensitive polymers as active substance carriers. Polimery W Medycynie 38(1):15-26. 2008 (English language abstract).
Keithley et al. GDNF protects the cochlea against noise damage. Neuroreport 9(10):2183-7. 1998.
Kim et al. Effects of tumor necrosis factor alpha antagonist, platelet activating factor antagonist, and nitric oxide synthase inhibitor on experimental otitis media with effusion. Ann Otol Rhinol Laryngol 115(8):617-23. 2006.
Kitahara et al. Up-regulation of cochlear aquaporin-3 mRNA expression after intra-endolymphatic sac application of dexamethasone. Neurol Res. 25(8):865-70. 2003.
Lamm et al. The effect of prednisolone and non-steroidal anti-inflammatory agents on the normal and noise-damaged guinea pig inner ear. Hear Res 115(1-2):149-61. 1998.
Lavreysen et al. Therapeutic potential of group III metabotropic glutamate receptors. Curr Med Chem I 5(7): 671-84. 2008.
Lee et al. Novel therapy for hearing loss: delivery of insulin-like growth factor 1 to the cochlea using gelatin hydrogel. Otol Neurotol 28(7):976-81. 2007.
Lee et al. Regional delivery of vancomycin using pluronic F-127 to inhibit methicillin resistant *Staphylococcus aureus* (MRSA) growth in chronic otitis media in vitro and in vivo. J Control Release 96(1): 1-7. 2004.
Liu et al. Permeability of different Dexamethasone drugs through round window membrane. Zhonghua Er Bi Yan Hou Tou Jing Wai Ke Za Zhi 41(3):211-5. 2006 (English abstract).
Majithiya et al. Thermoreversible-mucoadhesive Gel for Nasal Delivery of Sumatriptan. AAPS PharmSciTech (2006) 7(3):E1-E7.
Mansour et al. Ocular Poloxamer-Based Ciprofloxacin Hydrochloride in Situ Forming Gels. Drug Development and Industrial Pharmacy. 34(7):744-752. 2008.
McCarthy et al. Alport syndrome: a review. Clinical Eye and Vision Care 12:139-150 (2000).
McGuinness et al. Exogenous BDNF rescues rat spiral ganglion neurons in vivo. Otol Neurotol 26(5):1064-72. 2005.
Meltser et al. Estrogen receptor beta protects against acoustic trauma in mice. J Clin Invest 118(4):1563-70. 2008.
Miceli et al. Molecular pharmacology and therapeutic potential of neuronal Kv7-modulating drugs. Curr Opin Phannacol 8(1):65-74. 2008.
Mitsukawa et al. A selective metabotropic glutamate receptor 7 agonist: activation of receptor signaling via an allosteric site modulates stress parameters in vivo. Proc Natl Acad Sci U S A 102(51):18712-7. 2005.

(56) References Cited

OTHER PUBLICATIONS

Mostafa Transtympanic Membrane Delivery of Antibiotics-Pharmacokinetic Studies in Chinchillas. Dissertation submitted to the Graduate School of the University of Minnesota in Mar. 2007.
Nakagawa et al. Local drug delivery to inner ear for treatment of hearing loss. Curr Drug Ther 3:143-147. 2008.
Nance et al. The Genetics of Deafness. Mental Retardation and Developmental Disabilities. 2003. Wiley-Liss. 9:109-119.
Nishimaki et al. Reduction of metabotropic glutamate receptor-mediated heterosynaptic inhibition of developing MNTB-LSO inhibitory synapses. Eur J Neurosci 26(2):323-30. 2007.
Nouvian et al. Degeneration of sensory outer hair cells following pharmacological blockade of cochlear KCNQ channels in the adult guinea pig. Eur .1. Neurosci 17(12):2553-62. 2003.
Oldstone. Virus-induced autoimmunity: molecular mimicry as a route to autoimmune disease. J. Autoimmun. (1989) 2(suppl): 187-194.
Oliveira et al. Viral etiology for inner ear diseases: proven, unproven, unlikely. ORL (2008) 70:42-51.
Park et al. Effect of inhibitor of tumor necrosis factor-alpha and oxatomide on immune mediated otitis media. Laryngoscope 116(9):1642-6. 2006.
Parnes et al. Corticosteroid pharmacokinetics in the inner ear fluids: an animal study followed by clinical application. Laryngoscope 109(7 Pt 2 Supplement No. 91):1-17. 1999.
Paulson et al. A novel controlled local drug delivery system for inner ear disease. Laryngoscope 118(4):706-11. 2008.
PCT/US10/053214 Search Report dated Jul. 1, 2011.
PCT/US2008/061330 International Search Report mailed Jul. 31, 2008.
PCT/US2009/051172 International Search report mailed Feb. 18, 2010.
PCT/US2009/067552 International Search Report mailed Aug. 18, 2010.
Peng et al. Clinical investigation of different routes of administration of dexamethasone on sudden deafness. Lin Chung Er Bi Yan Hou Tou ling Wai Ke Za Zhi 22(10):442-5. 2008 (English translation).
Piu et al. OTO-104: A Sustained-Release Dexamethasone Hydrogel for the Treatment of Otic Disorders. Otol & Neurology. 32(1):171-179 (2011).
Piu et al. Towards predicting human inner ear pharmacokinetics: allometric scaling using guinea pigs and sheep. Abstract, ARO Meeting , Feb. 6-10, 2010.
Piu. OTO-104: a sustained release dexamethasone hydrogel formulation for the treatment of Meniere's disease. Oral presentation title: Recent topics in Meniere's disease treatment> Nov. 16, 2010.
Plontke et al. Rapid clearance of methylprednisolone after intratympanic application in humans. Comment on: Bird PA, Begg El, Zhang M, et al. Intratympanic versus intravenous delivery of methylprednisolone to cochlear perilymph. Otol Neurotol 2007; 28:1124-30. Otol Neurotol 29(5):732-3. 2008.
Pondugula et al. Glucocorticoids stimulate cation absorption by semicircular canal duct epithelium via epithelial sodium channel. Am I Physiol Renal Physiol 286(6):F1127-35. 2004.
Pondugula et al. Glueocorticoid regulation of genes in the amiloride-sensitive sodium transport pathway by semicircular canal duct epithelium of neonatal rat. Physiol Genomics 24(2):114-23. 2006.
Psillas et al. Potential efficacy of early treatment of acute acoustic trauma with steroids and piracetam after gunshot noise. Eur Arch Otorhinolaryngol 265(12):1465-9. 2008.
Puel. Chemical synaptic transmission in the cochlea. Prog Neurobiol 47(6):449-76, 1995.
Qi et al. Development of a Poloxamer Analogs/Carbopol-based in situ Gelling and Mucoadhesive Ophthalmic Delivery System for Puerarin. International Journal of Pharmaceuticals. Elsevier BV. NL. 337(1-2): 178-187. 2007.
Salt et al. Distribution of Dexamethasone and Preservation of Inner Ear Function following Intratympanic Delivery of a Gel-Based Formulation. Audiology Neurology 16:323-335 (2011).
Salt et al. Local Inner Ear Drug Delivery and Pharmacokinetics. Drug Discovery Today. NIH,10(19):1299-1306 (2005).
Satoh et al. Tumor necrosis factor-alpha, an initiator, and etanercept, an inhibitor of cochlear inflanunation. Laryngoscope 112(9):1627-34. 2002.
Schoepp et al. Pharmacological agents acting at subtypes of metabotropic glutamate receptors. Neuropharmacology 38(10):1431-76. 1999.
Schuknecht. Ablation therapy for the relief of Ménière's disease. Laryngoscope. (1956) 66:859-870.
Seidman et al. Anti-intercellular adhesion molecule-1 antibody's effect on noise damage. Laryngoscope 119(4):707-12. 2009.
She et al. A short term study on the efficacies of intratympanic prednisolone and dexamethasone injection for subjective tinnitus. Lin Chung Er Bi Yan Hou Tou Jing Wai Ke Za Zhi 22(19):871-3. 2008 (English translation).
Shepherd et al. Neurotrophins and electrical stimulation for protection and repair of spiral ganglion neurons following sensorineural hearing loss. Hear Res 242(1-2):100-9. 2008.
Shin, et al. Mucoadhesive and Physicochemical Characterization of Carbopol-Poloxamer gels Containing Trimcinolone Acetonide. Drug Developement and Industrial Pharmacy. 26(3):307-312. 2000.
Shinohara et al. Neurotrophic factor intervention restores auditory function in deafened animals. Proc Natl Acad Sci U S A 99(3):1657-60. 2002.
Song Design and Synthesis of Factor Xa Inhibitors and Their Prodrugs. Bioogranic & Medicinal Chemistry Letters. 13:297-300 (2003).
Sun et al. In vitro permeability of round window membrane to transforming dexamethasone with delivery vehicles—a dosage estimation. Chin Med J (Engl) 120(24):2284-9. 2007.
Synphora AB. website printout for JB004/A 2009.
Tabuchi et al. Hearing impairment in TRPV4 knockout mice. Neurosci Lett 382(3):304-8. 2005.
Taguchi et al. Expressions of aquaporin-2, vasopressin type 2 receptor, transient receptor potential channel vanilloid (TRPV)1, and TRPV4 in the human endolymphatic sac. Laryngoscope 117(4):695-8. 2007.
Tahera et al. NF-kB mediated glucocorticoid response in the inner ear after acoustic trauma. J Neurosci Res 1;83(6):1066-76. 2006.
Takeda et al. Aquaporins as potential drug targets for Meniere's disease and its related diseases. Handb Exp Pharmacol 190:171-84. 2009.
Takeda et al. Decompression effects of erythritol on endolymphatic hydrops. Auris Nasus Larynx 36(2):146-51. 2009.
Takeda et al. The effects of V2 antagonist (OPC-31260) on endolymphatic hydrops. Hear Res 182(1-2):9-18. 2003.
Takemura et al. Direct inner ear infusion of dexamethasone attenuates noise-induced trauma in guinea pig. Hear Res 196(1-2):58-68. 2004.
Takumida and Anniko Nitric oxide in the inner ear. Cur Opin Neural 15(1):11-5. 2002.
Tang et al. COUP-TFI controls Notch regulation of hair cell and support cell differentiation. Development 133(18):3683-93. 2006.
The Royal National Institute for Deaf People (RNID), advertisement insert in Nature Reviews Drug Discovery. May 2009.
Thorne et al. Potential role of purinergic signalling in cochlear pathology. Audiol Neurootol 7(3):180-4. 2002.
U.S. Appl. No. 12/472,034 Notice of Allowance dated Sep. 30, 2013.
U.S. Appl. No. 12/486,697 Office Action dated Apr. 26, 2011.
U.S. Appl. No. 12/504,553 Office Action dated Feb. 14, 2012.
U.S. Appl. No. 12/506,091 Office Action dated Feb. 22, 2012.
U.S. Appl. No. 12/837,286 Office Action dated Mar. 13, 2013.
U.S. Appl. No. 13/500,971 Office Action dated Jul. 17, 2014.
U.S. Appl. No. 13/500,971 Office Action dated Mar. 11, 2013.
U.S. Appl. No. 13/500,971 Office Action dated Sep. 18, 2013.
Van Wijk et al. Local perfusion of the tumor necrosis factor alpha blocker infliximab to the inner ear improves autoimmune neurosensory hearing loss. Audiol Neurootol 11(6):357-65, 2006.

(56) References Cited

OTHER PUBLICATIONS

Varshosaz et al. Designing of a Thermosensitive Chitosan/Poloxamer In Situ Gel for Ocular Delivery of Ciprofloxacin. The Open Drug Delivery Journal. 2:61-70. Published 2008.
Viegas et al. Osmotic behavior of poloxamer 407 and other non-ionic surfactants in aqueous solutions. Int. J. Pharm. 160:157-162 (1998).
Wang et al. A novel dual inhibitor of calpains and lipid peroxidation (BN82270) rescues the cochlea from sound trauma. Neuropharmacology 52(6):1426-37, 2007.
Wang et al. Dose-dependent sustained release of dexamethasone in inner ear cochlear fluids using a novel local delivery approach. Audiol Neurotol 14:393-401. 2009.
Wang et al. Over-expression of X-linked inhibitor of apoptosis protein slows presbycusis in C57BL/6J mice. Neurobiol Aging. Aug. 26, 2008 [Epub ahead of print].
Wang et al. Pharmacokinetic and safety profile of OTO-104: a sustained release dexamethasone hydrogel for inner ear delivery. Abstract. ARO Meeting Feb. 6-10, 2010.
Wang et al. Pharmacokinetic and toxicity profile of OTO-104—a sustained release. ARO MidWinter meeting. Abstract 644. Feb. 8, 2010.
Wang et al. Pharmacokinetic and toxicity profile of the clinical candidate OTO-104: a sustained release dexamethasone hydrogel for inner ear delivery. 2010 Abstracts selected for AOS spring meeting. Las Vegas, NV. May 1-2, 2010.
Wang et al. Pharmacokinetic and toxicity profile of the clinical candidate OTO-104: a sustained release dexamethasone hydrogel for inner ear delivery. Abstract. COSM Meeting. May 1-2, 2010.
Wang et al. Pharmacokinetics of dexamethasone solution following intratympanic injection in guinea pig and sheep. Audiol Neurotol 16:233-241. 2011.
Wang et al. Principles of Inner Ear Sustained Release Following Intratympanic Administration. Laryngoscope 121:385-391 (2011).
Watanabe et al. Inhibition of inducible nitric oxide synthase lowers the cochlear damage by lipopolysaccharide in guinea pigs. Free Radic Res 32(4):363-70. 2000.
Watanabe et al. Nitric oxide synthase inhibitor reduces the apoptotic change in the cisplatin-treated cochlea of guinea pigs. Anticancer Drugs 11(9):731-5.2000.
Watanabe et al. Nitric oxide synthase inhibitor suppresses the ototoxic side effect of cisplatin in guinea pigs. Anticancer Drugs 11(5):401-6. 2000.
Yamamoto et al. Inhibition of Notch/RBP-J signaling induces hair cell formation in neonate mouse cochleas. J Mol Med 84(1):37-45. 2006.
Yang et al. Intratympanic immunosuppressives for prevention of inunune-mediated sensorineural hearing loss. Am J Otol 21(4):499-504. 2000.

Yildirim et al. Effect of intratympanic dexamethasone on noise-induced temporary threshold shift. Laryngoscope 115(7):1219-22. 2005.
Yun, et al. Prolonged Antifungal Effects of Clotrimazole-Containing Mucoadhesive Thermosensitive Gels on Vaginitis. Journal of Controlled Release. Elsevier, Amsterdam, NL. 82(1):39-50. 2002.
Zheng et al. Vanilloid receptors in hearing: altered cochlear sensitivity by vanilloids and expression of TRPV1 in the organ of corti. J Neurophysiol 90(1):444-55. 2003.
Zhou et al. Intratympanic administration of methylprednisolone reduces impact of experimental intensive impulse noise trauma on hearing. Acta Oto-Laryngologica 129:602-607. 2009.
Bovo et al. Immune-mediated inner ear disease. Acta Oto-Laryngologica 126:1012-1021 (2006).
Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).
Chen et al. Preliminary study on brain-targeted drug delivery via inner ear. Acta Pharmaceutica Sinica 42:1102-1106 (2007) (English Abstract).
Co-pending U.S. Appl. No. 14/741,092, filed Jun. 16, 2015.
Co-pending U.S. Appl. No. 14/836,184, filed Aug. 26, 2015.
Feng et al., Effect of Poloxamer 407 on the cochlear orphology and hearing function after perfusion in round window: experiment with guinea pigs. National Medical Journal of China 87:2289-2291 (2007) (English Translation).
Lloyd et al. A patient with tinnitus. Clin Otolaryngology 33:25-28 (2008).
Morden et al. Topical Fluoroquinolones for Eye and Ear. Am Fam Physician 62(8):1870-1876 (2000).
Pappas et al. Topical Antibiotic Ear Drops: Are They Safe? Int J Clin Pract. 60:1115-1119 (2006).
PCT/US2014/52754 International Search Report and Written Opinion dated Nov. 4, 2014.
Ross et al. Aqueous Solubilities of some variously Substituted Quinolone Antimicrobials. Int'l J of Pharm 63:237-250 (1990).
Sismanis. Tinnitus. Curr Neurol Neurosci Rep. 1(5):492-499 (2001).
U.S. Appl. No. 13/500,971 Office Action dated Jan. 9, 2015.
U.S. Appl. No. 13/500,971 Office Action dated May 29, 2015.
U.S. Appl. No. 13/645,126 Office Action dated Jan. 22, 2015.
U.S. Appl. No. 13/645,126 Office Action dated Jun. 12, 2015.
U.S. Appl. No. 13/848,636 Office Action dated May 14, 2015.
U.S. Appl. No. 14/618,926 Office Action dated Mar. 24, 2015.
U.S. Appl. No. 14/618,926 Office Action dated May 4, 2015.
U.S. Appl. No. 14/469,408 Office Action dated May 6, 2016.
U.S. Appl. No. 14/741,092 Office Action dated May 31, 2016.
PCT/US2014/052754 International Preliminary Report on Patentability dated Mar. 10, 2016.
U.S. Appl. No. 13/500,971 Office Action dated Mar. 24, 2016.
U.S. Appl. No. 13/500,971 Office Action dated Oct. 15, 2015.
U.S. Appl. No. 14/922,448 Office Action dated Apr. 15, 2016.

\* cited by examiner

Figure 2

| Ciprofloxacin (mg/ml) | CIPRODEX | CETRAXAL | 0.06% | 0.2% | 0.6% | 2% | 6% | 12% |
|---|---|---|---|---|---|---|---|---|
| | 3.0 | 2.0 | 0.6 | 2.0 | 6.0 | 20.0 | 60.0 | 120.0 |
| Guinea pigs | | | | | | | | |
| Regimen | bid, 7 days 10 µl AU | bid, 7 days 15 µl AU | Single IT 50 µl AU | Single IT 50 µl AU | Single IT 50 µl AU | Single IT 50 µl AU | Single IT 50 µl AU | Single IT 50 µl AU |
| Cumulative dose (mg) | 0.42 | 0.42 | 0.03 | 0.10 | 0.30 | 1.00 | 3.00 | 6.00 |
| Chinchillas | | | | | | | | |
| Regimen | bid, 3 days 10 µl AU | bid, 3 days 15 µl AU | Single IT 50 µl AU | Single IT 50 µl AU | Single IT 50 µl AU | Single IT 50 µl AU | Single IT 50 µl AU | Single IT 50 µl AU |
| Cumulative dose (mg) | 0.18 | 0.18 | 0.03 | 0.10 | 0.30 | 1.00 | 3.00 | 6.00 |

| | | $C_{max}$ µg/mL | AUC µg·h/mL | $AUC_{0-24}$ µg·h/mL | MRT h | T>MIC h | $C_{max}$/MIC ratio | $AUC_{0-24}$/MIC h |
|---|---|---|---|---|---|---|---|---|
| CIPRODEX | | 22.6 | 3078 | 303 | 188 (11) | 601 (22) | 11 | 152 |
| CETRAXAL | | 24.1 | 5411 | 405 | 217 (16) | 611 (29) | 12 | 203 |
| OTO-201 | 0.06% | 45.4 | 2288 | 1088 | 34 | 63 | 23 | 544 |
| | 0.2% | 68.5 | 3728 | 1645 | 37 | 90 | 35 | 823 |
| | 0.6% | 77.4 | 7663 | 1858 | 143 | 322 | 39 | 929 |
| | 2% | 96.9 | 11025 | 2326 | 200 | 413 | 48 | 1163 |
| | 6% | 91.7 | 23921 | 2200 | 246 | 715 | 46 | 1100 |
| | 12% | 99.9 | 32026 | 2398 | 293 | 721 | 50 | 1199 |

Figure 3

METHODS FOR THE TREATMENT OF PEDIATRIC OTIC DISORDERS

CROSS-REFERENCE

This application claims the benefit of U.S. Provisional Application No. 61/870,318 filed Aug. 27, 2013, and U.S. Provisional Application No., 61/914,904 filed Dec. 11, 2013, each of which is hereby incorporated by reference in its entirety.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein are compositions, formulations, therapeutic methods, uses, and kits for the controlled release of desired agents to at least one structure or region of the ear. Provided herein in some embodiments are methods of treating a pediatric otic disease or condition associated with a microbial infection, the method comprising administering into the middle ear of a pediatric patient in need thereof an aqueous thermoreversible gel composition comprising micronized ciprofloxacin and poloxamer 407. In some embodiments, the composition comprises 1.8 to 6.6% by weight of micronized ciprofloxacin and 15-17% by weight of poloxamer 407. In certain embodiments, the composition comprises 1.8-2.2% by weight of micronized ciprofloxacin. In other embodiments, the composition comprises 5.4-6.6% by weight of micronized ciprofloxacin.

In certain embodiments, the composition further comprises a buffering agent. In some embodiments, the buffering agent comprises tromethamine. In some embodiments, the composition further comprises an osmolality modifier. In some embodiments, the osmolality modifier comprises sodium chloride. In some embodiments, the the composition further comprises a pH adjusting agent. In some embodiments, the composition has a pH of about 7.0 to about 8.0. In some embodiments, the composition comprises micronized ciprofloxacin, poloxamer 407, sodium chloride, tromethamine, hydrochloric acid, and water. In some embodiments, the composition consists essentially of micronized ciprofloxacin, poloxamer 407, sodium chloride, tromethamine, hydrochloric acid, and water.

Some embodiments provided herein describe methods of treating a pediatric otic disease or condition associated with a microbial infection, the method comprising administering to a pediatric patient a composition that is free of butylated hydroxytoluene (BHT). In some embodiments, the composition is preservative-free.

In some embodiments, any composition described herein is administered to the pediatric patient through a single, intratympanic injection to each infected ear. In some embodiments, the composition is administered to a pediatric patient via an intratympanic injection anterior to the round window membrane. In some embodiments, the composition is administered to a pediatric patient via an intratympanic injection into the middle ear. In some embodiments, the composition is administered following myringotomy. In some embodiments, the composition is administered to the site of myringotomy of the pediatric patient. In certain embodiments, the composition is administered before tympanostomy tube placement. In other embodiments, the composition is administered after tympanostomy tube placement.

In some embodiments, the pediatric otic disease or condition is otitis externa or otitis media. In further or additional embodiments, the pediatric otic disease or condition is otitis media with effusion. In certain embodiments, the pediatric otic disease or condition is bilateral middle ear effusion.

In some embodiments, the pediatric patient is 6 months to 12 years old. In certain embodiments, the pediatric patient is 6 months to 2 years old. In other embodiments, the pediatric patient is 2 years to 12 years old.

In some embodiments, the pediatric otic disease or condition is associated with a bacterial infection. In certain embodiments, the bacterial infection is associated with *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof. In some embodiments, the pediatric otic disease or condition is associated with *Streptococcus pneumoniae, Haemophilus influenzae, Moraxella catarrhalis, Streptococcus pyogenes, Staphylococcus aureus*, or a combination thereof. In some embodiments, the pediatric otic disease or condition is associated with *Streptococcus pneumonia*. In some embodiments, the pediatric otic disease or condition is associated with *Haemophilus influenzae*. In some embodiments, the pediatric otic disease or condition is associated with *Moraxella catarrhalis*.

BRIEF DESCRIPTION OF FIGURES

FIG. 2: Summary of Composition A, CIPRODEX® and CETRAXAL® treatment regimens.

FIG. 3: Comparison of middle ear pharmacokinetic parameters of ciprofloxacin following administration of Composition A, CIPRODEX® or CETRAXAL®. AUC: Area under the curve; MRT: Mean residence time; MIC: Minimum inhibitory concentration. A MIC of 2 µg/ml was defined based upon the breakpoint for bacteria of intermediate susceptibility to ciprofloxacin.

DETAILED DESCRIPTION OF THE INVENTION

Figure 1:
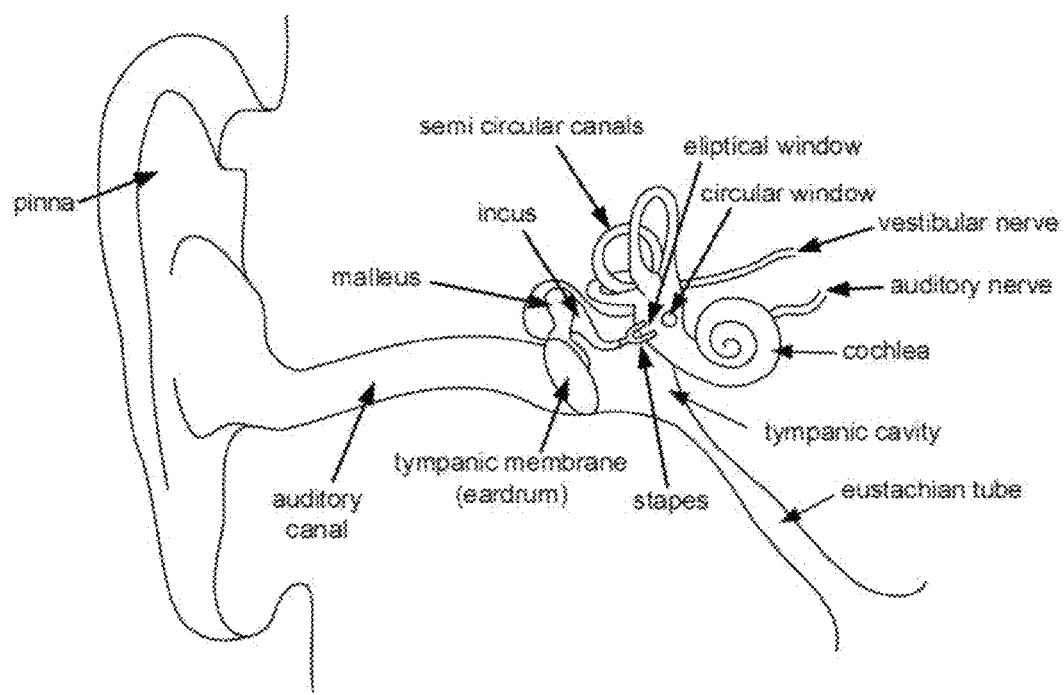
FIG. 1 illustrates the anatomy of the ear

Provided herein are controlled release antimicrobial agent compositions and formulations for the treatment of pediatric otic disorders or conditions, including otitis externa, otitis media, Ramsay Hunt syndrome, otosyphilis, AIED, Meniere's disease, and vestibular neuronitis. In some embodiments, the antimicrobial agent is ciprofloxacin. Compositions comprising combinations of therapeutic agents useful for the treatment of otic disorders, including combinations of different antimicrobial agents, as well as combinations of antimicrobial agents with other therapeutic agents, are also encompassed in certain embodiments disclosed herein.

Otitis externa (OE), also referred to as swimmer's ear, is an inflammation of the external ear and/or ear canal. OE is primarily caused by bacteria (e.g., *Pseudomonas aeruginosa* and *Staphylococcus aureus*) or fungi (e.g., *Candida albicans* and *Aspergillus*) in the outer ear, which establish infection following damage to the skin of the ear canal. Symptoms of OE include otalgia, swelling, and otorrhea. If the condition progresses significantly, OE may cause temporary conductive hearing loss as a result of the swelling and discharge. Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids.

Otitis media (OM) is an inflammation of the middle ear. Bacterial infection accounts for a large percentage of OM cases, with more than 40% of cases attributed to *Streptococcus pneumoniae* infection. However, viruses, as well as other microbes, may account for OM conditions. Because OM can be caused by a virus, bacteria or both, various antimicrobial agents are used to eliminate the underlying pathogen.

Syphilis is a venereal disease, caused by the spirochete *Treponema pallidum*, which may result in otic disorders, particularly cochleovestibular disorders, due to membranous labyrinthitis, and secondarily meningitis. Both acquired and congenital syphilis can cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes.

Treatment of otosyphilis (syphilis presenting otic symptoms) typically includes a combination of steroids and antibacterial agents. Such treatments may be effective in eradicating the spirochete organism while reducing inflammation. However, *Treponemas* may remain in the cochlear and vestibular endolymph even after eradication from other sites in the body. Accordingly, long term treatment with penicillins may be required to achieve complete eradication of the spirochete organism from the endolymph fluid.

Systemic antimicrobial administration for the treatment of otic disorders, e.g., OE, OM and otosyphilis, may create a potential inequality in drug concentration with higher circulating levels in the serum, and lower levels in the target auris interna organ structures. As a result, fairly large amounts of drug are required to overcome this inequality in order to deliver sufficient, therapeutically effective quantities to the inner ear. Further, bioavailability is often decreased due to metabolism of the drug by the liver. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant undesired side effects of systemic delivery of antimicrobial agents (which are generally understood to be toxic to cells), disclosed herein are methods and compositions for local delivery of antimicrobial agents to auris media structures. In some embodiments, the auris-acceptable sustained-release formulations disclosed herein are capable of being administered into the middle ear via intratympanic injection. In some embodiments, the auris-acceptable sustained-release formulations are administered into the middle ear through entry via a myringotomy incision site. Alternatively, the auris-acceptable sustained-release formulations is applied via syringe and needle, wherein the needle is inserted through the tympanic membrane into the middle ear.

In addition, localized treatment of the auris media structures also affords the one or more benefit of improved pK profiles, improved uptake, low systemic release, and/or improved toxicity profile.

Because of the localized targeting of the antimicrobial agent formulations and compositions, the risk of adverse effects can be reduced as a result of treatment with previously characterized toxic or ineffective antimicrobial agent. Localized administration of antimicrobial agent compositions reduces the risk of development of resistance to antibiotics compared to the risk for development of antibiotic resistance when an antibiotic is administered systemically. The compositions described herein are effective for recurring otic diseases or conditions including, for example, recurring ear infections in children without the need for changing treatment regimens (e.g., in response to development of antibiotic resistance). Accordingly, also contemplated within the scope of the embodiments herein is the use of antimicrobial agents in the treatment of otic diseases or conditions including otitis externa, otitis media, Ramsay Hunt syndrome, otosyphilis, AIED, Meniere's disease, and vestibular neuronitis, including therapeutic agents that have been previously rejected by practitioners because of adverse effects or ineffectiveness of the antimicrobial agent(s).

Also included within the embodiments disclosed herein is the use of additional auris media and/or auris interna-acceptable agents in combination with the antimicrobial agent formulations and compositions disclosed herein. When used, such agents assist in the treatment of hearing or equilibrium loss or dysfunction resulting from an autoimmune disorder, including vertigo, tinnitus, hearing loss, balance disorders, infections, inflammatory response or combinations thereof. Accordingly, agents that ameliorate or reduce the effects of vertigo, tinnitus, hearing loss, balance disorders, infections, inflammatory response or combinations thereof are also contemplated to be used in combination with the antimicrobial agent(s) described herein.

In some embodiments, the composition further comprises an antimicrobial agent as an immediate release agent wherein the immediate release antimicrobial agent is the same agent as the controlled-release agent, a different antimicrobial agent, an additional therapeutic agent, or a combination thereof. In some embodiments, the composition further comprises an additional therapeutic agent, including an additional antimicrobial agent, an anti-inflammatory agent, a corticosteroid, a cytotoxic agent, an anti-TNF agent, a collagen, a gamma-globulin, an interferon, a platelet activator factor antagonist, a nitric oxide synthase inhibitor, or combinations thereof. In another aspect, the additional therapeutic agent is an immediate release or a controlled release agent.

In some embodiments, the additional therapeutic agent is an immediate release agent. In some embodiments, the additional therapeutic agent is a controlled release agent.

Accordingly, provided herein are controlled release antimicrobial agent formulations and compositions to locally treat auris media and/or auris interna structures of pediatric patients, thereby avoiding side effects as a result of systemic administration of the antimicrobial agents. The locally applied antimicrobial agent formulations and compositions are compatible with auris media, and are administered either directly to the desired auris media structure of a pediatric patient, e.g. the tympanic cavity, or administered to a structure in direct communication with areas of the auris media.

By specifically targeting the auris media structures of the pediatric patient, adverse side effects as a result of systemic treatment are avoided. Moreover, by providing a controlled release antimicrobial agent formulation or composition to treat otic disorders, a constant and/or extended source of antimicrobial agent is provided to the pediatric patient suffering from an otic disorder, reducing or eliminating the variability of treatment.

Intratympanic injection of therapeutic agents is the technique of injecting a therapeutic agent behind the tympanic membrane into the auris media and/or auris interna. Despite early success with this technique (Schuknecht, Laryngoscope (1956) 66, 859-870) some challenges do remain. For example, access to the auris media, the site of drug absorption into the auris media, can be challenging.

In addition, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intratympanic compositions: the inner ear provides sui generis formulation challenges. Thus, compositions developed for other parts of the body have little to no relevance for an intra-tympanic composition.

There is little guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic formulations that feature suitable levels of pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the formulations described herein aid visualization of the administered compositions obviating the need for invasive procedures (e.g., removal of perilymph) during preclinical and/or clinical development of intratympanic therapeutics.

Provided herein are controlled release antimicrobial agent formulations and compositions to locally treat targeted auris structures of pediatric patients, thereby avoiding side effects as a result of systemic administration of the antimicrobial agent formulations and compositions. The locally applied antimicrobial agent formulations and compositions and devices are compatible with the targeted auris structures, and administered either directly to the desired targeted auris structure, e.g. the tympanic cavity, or administered to a structure in direct communication with areas of the auris media. By specifically targeting an auris structure, adverse side effects as a result of systemic treatment are avoided. Moreover, clinical studies have shown the benefit of having sustained exposure of drug to the perilymph of the cochlea, for example with improved clinical efficacy of sudden hearing loss when the therapeutic agent is given on multiple occasions. Thus, by providing a controlled release antimicrobial agent formulation or composition to treat otic disorders, a sustained, and/or extended source of antimicrobial agent is provided to the individual or patient suffering from an otic disorder, reducing or eliminating variability in treatment. Accordingly, one embodiment disclosed herein is to provide a composition that enables at least one antimicrobial agent to be released in therapeutically effective doses either at variable or constant rates such as to ensure a sustained release of the at least one agent.

In addition, the auris-acceptable sustained-release antimicrobial agent formulations and treatments described herein are provided to the target ear region of the individual in need, including the middle ear, and the individual in need is additionally administered an oral dose of antimicrobial agent. In some embodiments, the oral dose of antimicrobial agent is administered prior to administration of the auris-acceptable sustained-release antimicrobial agent formulation, and then the oral dose is tapered off over the period of time that the auris-acceptable sustained-release antimicrobial agent formulation is provided. Alternatively, the oral dose of antimicrobial agent is administered during administration of the auris-acceptable controlled-release antimicrobial agent formulation, and then the oral dose is tapered off over the period of time that the auris-acceptable controlled-release antimicrobial agent formulation is provided. Alternatively, the oral dose of antimicrobial agent is administered after administration of the auris-acceptable controlled-release antimicrobial agent formulation has been initiated, and then the oral dose is tapered off over the period of time that the auris-acceptable controlled-release antimicrobial agent formulation is provided.

In addition, the antimicrobial agent pharmaceutical compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated for the compositions and devices described herein are carriers, adjuvants and excipients that lack ototoxicity or are minimally ototoxic in order to allow effective treatment of the otic disorders contemplated herein with minimal side effects in the targeted regions or areas.

Intratympanic injection of compositions or devices creates several additional problems that must also be addressed before the composition or device can be administered. For example, there are many excipients that are ototoxic. While these excipients can be used when formulating an active agent for delivery by another method (e.g., topical), their use is generally limited, reduced or eliminated when formulating a delivery device to be administered to the ear due to their ototoxic effects.

By way of non-limiting example, the formulations disclosed herein are free or substantially free of alcohols, propylene glycol, and cyclohexane. In some embodiments, the formulations disclosed herein comprise less than about 50 ppm, less than about 25 ppm, less than about 20 ppm, less than about 10 ppm, less than about 5 ppm, less than about 1 ppm, of each of alcohols, propylene glycol, and cyclohexane.

In some embodiment, the use of preservatives is limited, reduced or eliminated when formulating the auris-acceptable sustained release formulation disclosed herein. As a non-limiting example, the use of the following commonly utilized preservatives should be limited, reduced or eliminated when formulating agents for administration to the ear: benzethonium chloride, benzalkonium chloride, butylated hydroxytoluene (BHT), and thiomersal. Thus, in some embodiments, the formulations disclosed herein are free or substantially free of benzethonium chloride, benzalkonium chloride, butylated hydroxytoluene (BHT), and thiomersal.

In some embodiments, the formulations disclosed herein comprise less than about 50 ppm, less than about 25 ppm, less than about 20 ppm, less than about 10 ppm, less than about 5 ppm, less than about 1 ppm, of each of benzethonium chloride, benzalkonium chloride, butylated hydroxytoluene (BHT), and thiomersal.

Certain antiseptics used to disinfect components of therapeutic preparations (or the devices utilized to administer the preparations) should be limited, reduced, or eliminated in otic preparations. For example, acetic acid, iodine, and merbromin are all known to be ototoxic. Additionally, chlorhexidene, a commonly used antiseptic, should be limited, reduced or eliminated to disinfect any component of an otic preparation (including devices used to administer the preparation) as it is highly ototoxic in minute concentrations (e.g., 0.05%). Thus, in some embodiments, the formulations disclosed herein are free or substantially free of acetic acid, iodine, merbromin, and chlorhexidene. In some embodiments, the formulations disclosed herein comprise less than about 50 ppm, less than about 25 ppm, less than about 20 ppm, less than about 10 ppm, less than about 5 ppm, less than about 1 ppm, of each of acetic acid, iodine, merbromin, and chlorhexidene.

Further, otic preparations require particularly low concentrations of several potentially-common contaminants that are known to be ototoxic. Other dosage forms, while seeking to limit the contamination attributable to these compounds, do not require the stringent precautions that otic preparations require. For example, the following contaminants should be absent or nearly absent from otic preparations: arsenic, lead, mercury, and tin. Thus, in some embodiments, a device disclosed herein is free or substantially free of arsenic, lead, mercury, and tin. In some embodiments, a device disclosed herein comprises less than about 50 ppm, less than about 25 ppm, less than about 20 ppm, less than about 10 ppm, less than about 5 ppm, less than about 1 ppm, of each of arsenic, lead, mercury, and tin.

CERTAIN DEFINITIONS

The term "auris-acceptable" with respect to a formulation, composition or ingredient, as used herein, includes having no persistent detrimental effect on the auris interna (or inner ear) of the subject being treated. By "auris-pharmaceutically acceptable," as used herein, refers to a material, such as a carrier or diluent, which does not abrogate the biological activity or properties of the compound in reference to the auris interna (or inner ear), and is relatively or is reduced in toxicity to the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

The term "about" refers to a variation customarily understood in the technical field of the present disclosure. In some embodiment, the term "about" refers to a variation of ±20%. In some embodiments, the term "about" refers to a variation of ±15%. In some embodiments, the term "about" refers to a variation of ±10%. In some embodiments, the term "about" refers to a variation of ±5%. In some embodiments, the term "about" refers to a variation of ±2%. In some embodiments, the term "about" refers to a variation of ±1%.

"Auris media" refers to the middle ear, including the tympanic cavity, auditory ossicles and oval window, which connects the middle ear with the inner ear.

"Blood plasma concentration" refers to the concentration of compounds provided herein in the plasma component of blood of a subject.

The term "diluent" refers to chemical compounds that are used to dilute the antimicrobial agent prior to delivery and which are compatible with the auris interna.

"Drug absorption" or "absorption" refers to the process of movement of the antimicrobial agents from the localized site of administration, by way of example only, the round window membrane of the inner ear, and across a barrier (the round window membranes, as described below) into the auris interna or inner ear structures. The terms "co-administration" or the like, as used herein, are meant to encompass administration of the antimicrobial agents to a single patient, and are intended to include treatment regimens in which the antimicrobial agents are administered by the same or different route of administration or at the same or different time.

The terms "effective amount" or "therapeutically effective amount," as used herein, refer to a sufficient amount of the active agent or otic agent (e.g., an antimicrobial agent, an anti-inflammatory agent) being administered that would be expected to relieve to some extent one or more of the symptoms of the disease or condition being treated. For example, the result of administration of an antimicrobial agent disclosed herein is reduction and/or alleviation of the signs, symptoms, or causes of tinnitus or balance disorders. For example, an "effective amount" for therapeutic uses is the amount of antimicrobial agent, including a formulation as disclosed herein required to provide a decrease or amelioration in disease symptoms without undue adverse side effects. The term "therapeutically effective amount" includes, for example, a prophylactically effective amount. An "effective amount" of an antimicrobial agent disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

The terms "enhance" or "enhancing" refers to an increase or prolongation of either the potency or duration of a desired effect of antimicrobial agent, or a diminution of any adverse symptomatology that is consequent upon the administration of the therapeutic agent. Thus, in regard to enhancing the effect of the antimicrobial agents disclosed herein, the term "enhancing" refers to the ability to increase or prolong, either in potency or duration, the effect of other therapeutic agents that are used in combination with the antimicrobial agent disclosed herein. An "enhancing-effective amount," as used herein, refers to an amount of antimicrobial agent or other therapeutic agent which is adequate to enhance the effect of another therapeutic agent or antimicrobial agent of the target auris structure in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, or advancement of a condition in a patient necessitating treatment.

The terms "kit" and "article of manufacture" are used as synonyms.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

As used herein, the term "antimicrobial agent" refers to compounds that inhibit the growth, proliferation, or multiplication of microbes, or that kill microbes. "Antimicrobial agents" may work by any suitable mechanism against the microbes, including by being toxic or cytostatic.

The term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, tympanostomy tubes, short electrodes, micro-prostheses or piston-like prostheses; needles; stem cell transplants; drug delivery devices; any cell-based therapeutic; or the like. Otic surgery includes middle ear surgery, inner ear surgery, tympanostomy, cochleostomy, labyrinthotomy, mastoidectomy, stapedectomy, stapedotomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

In prophylactic applications, compositions comprising the antimicrobial agents described herein are administered to a patient susceptible to or otherwise at risk of a particular disease, disorder or condition. For example, such conditions include and are not limited to otitis externa, otitis media, Ramsay Hunt syndrome, otosyphilis, AIED, Meniere's disease, and vestibular neuronitis. Such an amount is defined to be a "prophylactically effective amount or dose." In this use, the precise amounts also depend on the patient's state of health, weight, and the like.

As used herein "micronized ciprofloxacin" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent. In some embodiment, the "micronized ciprofloxacin" refers to micronized particles that are non-microencapsulated.

The mean residence time (MRT) is the average time that molecules of an active agent (e.g., a microbial agent) reside in an otic structure after a dose.

As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition, for example tinnitus, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Methods

Provided herein in some embodiments are methods of treating a pediatric otic disease or condition associated with a microbial infection. In some embodiments, the method comprises administering to a pediatric patient a composition comprising micronized ciprofloxacin and poloxamer 407. In some embodiments, the pediatric patient is 6 months to 12 years old. In certain embodiments, the pediatric patient is 6 months to 2 years old. In other embodiments, the pediatric patient is 2 years to 12 years old.

In some embodiments, the pediatric otic disease or condition is associated with a bacterial infection. In certain embodiments, the pediatric otic disease or condition is associated with *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof. In some embodiments, the pediatric otic disease or condition is associated with *Streptococcus pneumoniae, Haemophilus influenzae, Moraxella catarrhalis, Streptococcus pyogenes, Staphylococcus aureus*, or a combination thereof. In some embodiments, the pediatric otic disease or condition is associated with *Streptococcus pneumonia*. In some embodiments, the pediatric otic disease or condition is associated with *Haemophilus influenzae*. In some embodiments, the pediatric otic disease or condition is associated with *Moraxella catarrhalis*.

In some embodiments, the compositions described herein treat a pediatric otic disease or condition associated with traditionally resistant bacterial strains. In some embodiments, the compositions described herein treat a pediatric otic disease or condition associated with intermediate and resistant bacterial strains to ciprofloxacin. In some embodiments, the intermediate and resistant bacterial strains to ciprofloxacin exhibit a MIC above 2 µg/mL, above 25 µg/mL, above 50 µg/mL, or above 75 µg/mL.

In some embodiments, use of the compositions described herein provide adequate clinical cure against resistant microorganisms. In some embodiments, the time to clinical cure is 6 h, 8 h, 10 h, 12 h, 14 h, 16 h, 18 h, 20 h, 22 h, 24 h, 26 h, 28 h, 30 h, 32 h, 34 h, 36 h, 38 h, 40 h, 42 h, 44 h, 48 h, 50 h, 52 h, 54 h, 56 h, 58 h, 60 h, 64 h, 68 h, or 72 h. In certain embodiments, the time to clinical cure is about 12 h. In some embodiments, the time to clinical cure is less than 12 h. In certain embodiments, the time to clinical cure is about 18 h. In some embodiments, the time to clinical cure is less than 18 h. In certain embodiments, the time to clinical cure is about 24 h. In some embodiments, the time to clinical cure is less than 24 h. In certain embodiments, the time to clinical cure is about 36 h. In some embodiments, the time to clinical cure is less than 36 h. In certain embodiments, the time to clinical cure is about 48 h. In some embodiments, the time to clinical cure is less than 48 h. In certain embodiments, the resistant microorganisms are resistant to ciprofloxacin. In some embodiments, the methods described herein prevent or alleviate the potential for antibiotic resistance. In some embodiments, the use of the compositions described herein provides bacterial eradication. In certain embodiments, the methods described herein eradicate pre-therapy bacteria in the middle ear. In some embodiments, the use of the compositions described herein reduces middle ear effusion.

In some embodiments, the use of the compositions provided herein provides antimicrobial protection against biofilms. In some embodiments, the biofilms are present on tympanostomy tubes placed in a pediatric patient. In some embodiments, the compositions provided herein disrupt biofilms.

Some embodiments provided herein describe a method of treating or preventing post-surgical otorrhea. In some embodiments, the method comprises administering to a pediatric patient a composition comprising micronized ciprofloxacin and poloxamer 407. In some embodiments, the composition is administered to the myringotomy site prior to tympanostomy tube placement. In some embodiments, there is no visible otorrhea 3 days post-surgery. In other embodiments, there is no visible otorrhea 5 days post-surgery. In other embodiments, there is no visible otorrhea 7 days post-surgery. In other embodiments, there is no visible otorrhea 10 days post-surgery. In other embodiments, there is no visible otorrhea 14 days post-surgery.

In some embodiments, the methods described herein treat pediatric otic diseases or conditions without causing or leading to ototoxicity. In some embodiments, treatment of a pediatric otic disease or condition with a composition described herein provides minimal functional changes in hearing. In some embodiments, treatment of a pediatric otic disease or condition with a composition described herein provides no evidence of cochlear pathology. In some embodiments, treatment of a pediatric otic disease or condition with a composition described herein provides minimal threshold shifts. In some embodiments, treatment of a pediatric otic disease or condition with a composition described herein does not change or influence cochlear pathology. In some embodiments, treatment of a pediatric otic disease or condition with a composition described herein is not associated with cochlear toxicity. In some embodiments, treatment of a pediatric otic disease or condition with a composition described herein does not induce hair cell loss of the cochlea. In some embodiments, treatment of a pediatric otic disease or condition with a composition described herein does not affect the patency of tympanostomy tubes.

Anatomy of the Ear

As shown in FIG. 1, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Diseases

Pediatric otic disorders, including auris interna, auris media, and auris externa disorders, produce symptoms which include but are not limited to hearing loss, nystagmus, vertigo, tinnitus, inflammation, swelling, infection and congestion. These disorders may have many causes, such as infection, injury, inflammation, tumors and adverse response to drugs or other chemical agents.

Inflammatory Disorders of the Ear

Otitis externa (OE), also referred to as swimmer's ear, is an inflammation and/or infection of the external ear. OE is often caused by bacteria in the outer ear, which establish infection following damage to the skin of the ear canal. Primary bacterial pathogens that cause OE are *Pseudomonas aeruginosa* and *Staphylococcus aureus*, but the condition is associated with the presence of many other strains of gram positive and negative bacteria. OE is also sometimes caused by fungal infection in the outer ear, including *Candida albicans* and *Aspergillus*. Symptoms of OE include otalgia, swelling, and otorrhea. If the condition progresses significantly, OE may cause temporary conductive hearing loss as a result of the swelling and discharge.

Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids. Typical antibacterial agents for the treatment of OE include aminoglycosides (e.g., neomycin, gentamycin, and tobramycin), polymyxins (e.g., polymyxin B), fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, cefibuten, and ceftriaxone), penicillins (e.g., amoxicillin, amoxicillin-clavulanate, and penicillinase-resistant penicillins), and combinations thereof. Typical antifungal agents for the treatment of OE include clotrimazole, thimerasol, M-cresyl acetate, tolnaftate, itraconazole, and combinations thereof. Acetic acid is also administered to the ear, alone and in combination with other agents, to treat bacterial and fungal infections. Ear drops are often used as the vehicle for administration of the active agents. In the case that ear swelling has progressed substantially and ear drops do not penetrate significantly into the ear canal, a wick can be inserted into the ear canal to facilitate penetration of the treatment solutions. Oral antibiotics are also administered in the case of extensive soft tissue swelling that extends to the face and neck. When the pain of OE is extremely severe such that it interferes with normal activity, e.g., sleeping, pain relievers such as topical analgesics or oral narcotics may be given until the underlying inflammation and infection are alleviated.

Notably, some types of topical ear drops, such as ear drops containing neomycin, are safe and effective for use in the ear canal, but can be irritating and even ototoxic to the auris media, prompting concern that such topical preparations should not be used unless the tympanic membrane is known to be intact. Utilization of the formulations disclosed herein for the treatment of OE allows for use of active agents that are potentially damaging to the auris media, even when the tympanic membrane is not intact. Specifically, the controlled release formulations disclosed herein can be applied locally in the external ear with improved retention time, thus eliminating concern that the active agents will leak out of the ear canal into the auris media. Furthermore, otoprotectants can be added when ototoxic agents, such as neomycin, are used.

Treatment of severe OE with the antimicrobial compositions disclosed herein, particularly highly viscous and/or mucoadhesive formulations, also obviates the need for extended use of an ear wick. Specifically, the compositions disclosed herein have increased retention time in the ear canal as a result of the formulation technology, thus eliminating the need for a device to maintain their presence in the outer ear. The formulations can be applied in the outer ear with a needle or an ear dropper, and the active agents can be maintained at the site of inflammation without the aid of an ear wick. In some embodiments, antimicrobial agent compositions described herein further comprise anti-inflammatory agents and are useful in the treatment of otitis externa.

In some embodiments, the treatment of OE with antimicrobial formulations disclosed herein encompasses the treatment of granular myringitis, a specific form of OE characterized by chronic inflammation of the pars tensa of the tympanic membrane. The outer epithelial and underlying fibrous layers of the tympanic membrane are replaced by a proliferating granulation tissue. The predominant symptom is foul-smelling otorrhea. A variety of bacteria and fungi cause the condition, including *Proteus* and *Psuedomonas* species. Accordingly, antimicrobial agent formulations disclosed herein comprising antibacterial or antifungal agents are useful for the treatment of granular myringitis.

In some embodiments, the treatment of OE with antimicrobial formulations disclosed herein encompasses the treatment of chronic stenosing otitis externa. Chronic stenosing otitis externa is characterized by repeated infections, typically caused by bacteria or fungi. The primary symptoms are pruritus in the ear canal, otorrhea, and chronic swelling. Antimicrobial agent formulations disclosed herein comprising antibacterial or antifungal agents are useful for the treatment of chronic stenosing otitis externa.

In some embodiments, the treatment of OE with antimicrobial formulations disclosed herein encompasses the treatment of malignant or necrotizing external otitis, an infection involving the temporal and adjacent bones. Malignant external otitis is typically a complication of external otitis. It occurs primarily in persons with compromised immunity, especially in older persons with diabetes mellitus. Malignant external otitis is often caused by the bacteria *Pseudomonas aeruginosa*. Treatment typically involves correction of immunosuppression when possible, in conjunction with antibacterial therapy and pain relievers. According, antimicrobial agent formulations disclosed herein are useful for the treatment of malignant or necrotizing external otitis.

Otitis media (OM), which includes acute otitis media (AOM), chronic otitis media, otitis media with effusion (OME), recurrent acute otitis media (RAOM), chronic otitis media with effusion (COME), secretory otitis media, and chronic secretory otitis media as examples, is a condition affecting both adults and children. OM susceptibility is multifactorial and complex, including environmental, microbial and host factors. Bacterial infection accounts for a large percentage of OM cases, with more than 40% of cases attributed to *Streptococcus pneumoniae* infection. However, viruses, as well as other microbes, may also account for OM conditions. In some instances, otitis media is associated with eustachian tube dysfunction that is caused by, for example, anatomic blockage to inflammation, secondary to allergies, upper respiratory tract infection (URTI), trauma or the like.

Otitis media with effusion (OME) is characterized by a nonpurulent effusion of the middle ear that may be either mucoid or serous. Symptoms usually involve hearing loss or aural fullness. In children, hearing loss is generally mild and is often detected only with an audiogram. Serous otitis media is a specific type of OME caused by transudate formation as a result of a rapid decrease in middle ear pressure relative to the atmospheric pressure.

Because OM can be caused by a virus, bacteria or both, it is often difficult to identify the exact cause and thus the most appropriate treatment. Treatment options for OM include antibiotics, such as penicillins (e.g., amoxicillin and amoxicillin-clavulanate), clavulanate acid, trimethoprim-sulfamethoxazole, fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, cefibuten, and ceftriaxone), macrolides and azalides (e.g., erythromycin, clarithromycin, and azithromycin), sulfonamides, and combinations thereof. Surgical intervention is also available, including myringotomy, an operation to insert a tympanostomy tube through the tympanic membrane and into the patient's middle ear to drain the fluid and balance the pressure between the outer and middle ear. Antipyretics and analgesics, including benzocaine, ibuprofen and acetaminophen, may also be prescribed to treat accompanying fever or pain effects. Antimicrobial agent compositions disclosed herein comprising antibacterial or antifungal agents are useful for the treatment of pediatric otitis media (OM), which includes acute otitis media (AOM), chronic otitis media, otitis media with effusion (OME), recurrent acute otitis media (RAOM), chronic otitis media with effusion (COME), secretory otitis media, and chronic secretory otitis media or the like. In some embodiments, antimicrobial agent compositions described herein further comprise anti-inflammatory agents and are useful in the treatment of pediatric otitis media (OM), which includes acute otitis media (AOM), chronic otitis media, otitis media with effusion (OME), recurrent acute otitis media (RAOM), chronic otitis media with effusion (COME), secretory otitis media, and chronic secretory otitis media or the like. In some embodiments, the compositions disclosed herein comprising ciprofloxacin are useful for the treatment of pediatric otitis media with effusion. In some embodiments, the compositions disclosed herein comprising ciprofloxacin are useful for the treatment of pediatric bilateral middle ear effusion.

Regardless of the causative agent, increases in cytokine production, including interleukins and TNF, have been observed in the effluent media of individuals afflicted with OM. IL-1β, IL-6 and TNF-α are acute-phase cytokines that promote acute inflammatory response after infection with viruses and bacteria. Moreover, higher TNF-α levels have been associated with a history of multiple tympanostomy tube placements, indicating a role for TNF-α in chronic OM cases. Finally, direct injection of TNF-α and interleukins has been shown to induce middle ear inflammation in a guinea pig model. These studies support the role that cytokines may play in the origin and maintenance of OM in the auris media. Thus, treatment of OM includes the use of antimicrobial agents in conjunction with anti-inflammatory agents to eliminate the pathogen and treat the symptoms of inflammation. Such treatments include use of steroids, TNF-α inhibitors, platelet activating factor antagonists, nitric oxide synthase inhibitors, histamine antagonists, and combinations thereof in conjunction with the antimicrobial formulations disclosed herein.

Mastoiditis is an infection of the mastoid process, which is the portion of the temporal bone behind the ear. It is typically caused by untreated acute otitis media. Mastoiditis may be acute or chronic. Symptoms include pain, swelling, and tenderness in the mastoid region, as well as otalgia, erythematous, and otorrhea. Mastoiditis typically occurs as bacteria spread from the middle ear to the mastoid air cells, where the inflammation causes damage to the bony structures. The most common bacterial pathogens are *Streptococcus pneumoniae, Streptococcus pyogenes, Staphylococcus aureus*, and gram-negative bacilli. Accordingly, antimicrobial agent formulations disclosed herein comprising antibacterial agents effective against the bacteria are useful for the treatment of mastoiditis, including acute mastoiditis and chronic mastoiditis.

Bullous myringitis is an infection of the tympanic membrane, caused by a variety of bacteria and viruses, including *Mycoplasma* bacteria. The infection leads to inflammation of the tympanic membrane and nearby canal, and causes the formation of blisters on the ear drum. The primary symptom of Bullous myringitis is pain, which may be relieved through the administration of analgesics. Antimicrobial formulations disclosed herein comprising antibacterial and antiviral agents are useful for the treatment of Bullous myringitis.

Eustachian tubal catarrh, or Eustachian salpingitis, is caused from inflammation and swelling of the Eustachian tubes, resulting in a build-up of catarrh. Accordingly, antimicrobial formulations disclosed herein are useful for the treatment of Eustachian salpingitis.

Labyrinthitis, e.g., serous labyrinthitis, is an inflammation of the inner ear that involves one or more labyrinths housing the vestibular system. The primary symptom is vertigo, but the condition is also characterized by hearing loss, tinnitus, and nystagmus. Labrynthitis maybe acute, lasting for one to six weeks and being accompanied by severe vertigo and vomiting, or chronic, with symptoms lasting for months or even years. Labyrinthitis is typically caused by viral or bacterial infection. Accordingly, antimicrobial formulations disclosed herein comprising antibacterial and antiviral agents are useful for the treatment of labyrinthitis.

Facial nerve neuritis is a form of neuritis, an inflammation of the peripheral nervous system, afflicting the facial nerve. The primary symptoms of the condition are a tingling and burning sensation, and stabbing pains in the affected nerves. In severe cases, there may be numbness, loss of sensation, and paralysis of the nearby muscles. The condition is typically caused by herpes zoster or herpes simplex viral infection, but has also been associated with bacterial infection, e.g., leprosy. Accordingly, antimicrobial formulations disclosed herein comprising antibacterial and antiviral agents are useful for the treatment of facial nerve neuritis.

In some embodiments, antimicrobial formulations disclosed herein are also useful for the treatment of temporal bone osteoradionecrosis.

Ramsay Hunt Syndrome (Herpes Zoster Oticus)

Ramsay Hunt syndrome is caused by a herpes zoster infection of the auditory nerve. The infection may cause severe ear pain, hearing loss, vertigo, blisters on the outer ear, in the ear canal, as well as on the skin of the face or neck supplied by the nerves. Facial muscles may also become paralyzed if the facial nerves are compressed by the swelling. Hearing loss may be temporary or permanent, with vertigo symptoms usually lasting from several days to weeks.

Treatment of Ramsay Hunt's syndrome includes administration of antiviral agents, such as ganciclovir, acyclovir, famciclovir and valacyclovir. Antiviral agents may be given in combination with agents that treat symptoms of the infection, such as corticosteroids, analgesics and narcotics to relieve the pain, and scopolamine, diazempam, or other central nervous system agents to suppress vertigo. Capsaicin, lidocaine patches and nerve blocks may also be used. Surgery may be performed on compressed facial nerves to relieve facial paralysis.

Otosyphilis

Syphilis is a venereal disease, caused by the spirochete *Treponema pallidum*, which in its secondary and tertiary stages may result in otic disorders, particularly cochleovestibular disorders, due to membranous labyrinthitis, and secondarily meningitis. Both acquired and congenital syphilis can cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes. Syphilis infection may lead to congenital prenatal hearing loss, affecting approximately 11.2 per 100,000 live births in the United States, as well as sudden hearing loss in adults.

Treatment of otosyphilis (syphilis presenting otic symptoms) typically includes a combination of steroids (e.g., prednisilone) and antibacterial agents (e.g., benzathine penicillin G (BICILLIN LA®), penicillin G procaine, doxycycline, tetracycline, ceftriaxone, azithromycin). Such treatments may be effective in eradicating the spirochete organism. However, *Treponemas* may remain in the cochlear and vestibular endolymph even after eradication from other sites in the body. Accordingly, long term treatment with penicillins may be required to achieve complete eradication of the spirochete organism from the endolymph fluid. Also, in the case of a severe or advanced case of syphilis, a uricosuric drug, such as probenecid, may be administered in conjunction with the antibacterial agent to increase its efficacy.

Other Microbial Infections Causing Cochleovestibular Disorders

Other microbial infections are known to cause cochleovestibular disorders, including hearing loss. Such infections include rubella, cytomegalovirus, mononucleosis, varicella zoster (chicken pox), pneumonia, *Borrelia* species of bacteria (Lyme disease), and certain fungal infections. Accordingly, controlled release antimicrobial agent formulations disclosed herein are also used for localized treatment of these infections in the ear.

Autoimmune Inner Ear Disease

Autoimmune inner ear disease (AIED) is one of the few reversible causes of sensorineural hearing loss. It is a disorder appearing in both adults and children that often involves a bilateral disturbance of the audio and vestibular functions of the auris interna. In many cases, AIED occurs without systemic autoimmune symptoms, but up to one-third of patients also suffer from a systemic autoimmune illness, such as inflammatory bowel disease, rheumatoid arthritis, Ankylosing spondylitis, Systemic Lupus Erythematosus (SLE), Sjögren's Syndrome, Cogan's disease, ulcerative colitis, Wegener's granulomatosis and scleroderma. Behcet's disease, a multisystem disease, also commonly has audiovestibular problems. A classification scheme for AIED has been developed (Harris and Keithley *Otorhinolaryngology Head and Neck Surgery* (2002) 91, 18-32).

The immune system normally performs a crucial role in protecting the inner ear from invasive pathogens such as bacteria and viruses. However, in AIED the immune system itself begins to damage the delicate inner ear tissues. The inner ear is fully capable of mounting a localized immune response to foreign antigens. When a foreign antigen enters the inner ear, it is first processed by immunocompetent cells which reside in and around the endolymphatic sac. Once the foreign antigen has been processed by these immunocompetent cells, these cells secrete various cytokines which modulate the immune response of the inner ear. One result of this cytokine release is to facilitate the influx of inflammatory cells, which are recruited from the systemic circulation. These systemic inflammatory cells enter the cochlea via diapedesis through the spiral modiolar vein and its tributaries, and begin to participate in antigen uptake and deregulation just as it occurs in other parts of the body. Interleukin 1 (IL-1) plays an important role in modulating the innate (nonspecific) immune response and is a known activator of resting T helper cells and B-cells. T helper cells, once activated by IL-1, produce IL-2. IL-2 secretion results in differentiation of pluripotent T-cells into helper, cytotoxic and suppressor T-cell subtypes. IL-2 also assists T helper cells in the activation of B lymphocytes and probably plays a pivotal role in the immunoregulation of the immune response of the vestibular and cochlear regions. IL-2 is within the perilymph of the auris interna as early as 6 h after antigen challenge with peak levels at 18 h after antigen challenge. The perilymphatic levels of IL-2 then dissipate, and it is no longer present within the perilymph at 120 hours post antigen challenge.

Both IL-1β and tumor necrosis factor-α (TNF-α) may play a key role in the initiation and amplification of the immune response. IL-1β is expressed by the fibrocytes of the spiral ligament in the presence of trauma such as surgical trauma or acoustic trauma in a nonspecific response. TNF-α is expressed either by infiltrating systemic cells or by resident cells contained within the endolymphatic sac in the presence of antigen. TNF-α is released as part of the adaptive (specific) immune response in animal models. When antigen is injected into the auris interna of mice, IL-1β and TNF-α are both expressed and a vigorous immune response occurs. However, when antigen is introduced to the auris interna via the cerebral spinal fluid in the absence of trauma, only TNF-α is expressed and the immune response in minimal. Importantly, cochlear trauma in isolation also results in a minimal immune response. These results suggest that both the nonspecific and specific components of the immune response act in concert in the auris interna to achieve a maximal response.

Thus, if the cochlea is traumatized and an antigen is injected (or in the case of autoimmune disease, the patient has immune cells directed against inner ear antigens), both the nonspecific and the specific immune responses can be activated simultaneously. This results in the concurrent production of IL-1β as well as TNF-α which causes a greatly amplified level of inflammation leading to substantial damage to the auris interna.

Certain evidence suggests that viral infection is a factor in the initiation of the inflammatory response that results in AIED. Various autoimmune conditions are induced or enhanced by a variety of DNA and RNA virus infections. Acute or persistent viral infections induce or enhance autoimmune diseases in animal models as well. Similar antigenic determinants have also been observed on viruses and host components. Oldstone, M. B. A. *J. Autoimmun.* (1989) 2 (suppl): 187-194. Further, serological tests have identified viral infection in at least one patient diagnosed with a systemic autoimmune disorder that is often associated with AIED (Cogan's syndrome). Garcia-Berrocal, et al. *O.R.L.* (2008) 70: 16-20.

Accordingly, in some embodiments, controlled release antimicrobial agent compositions and formulations disclosed herein are administered for the treatment of AIED. Particularly, in certain embodiments, formulations disclosed herein comprising antiviral agents are administered for treatment of AIED. In other embodiments, the antimicrobial agent formulations disclosed herein are administered for the treatment of AIED in conjunction with other pharmaceutical agents useful for treating the same conditions or symptoms of the same conditions, including steroids, cytotoxic agents, collagen, gamma globulin infusion, or other immune modulating drugs. Steroids include, e.g., prednisone or decadron. Cytotoxic agents for the treatment of AIED include, e.g., methotrexate, cyclophosphamide, and thalidomide. Plasmapheresis procedures are optionally used. Treatment with oral collagen, gamma globulin infusions, or other immune modulating drugs (e.g. beta-interferon, alpha-interferon or copaxone) is also optionally used in combination with the antimicrobial agent formulations disclosed herein. The additional pharmaceutical agents are optionally administered together with the controlled release formulations disclosed herein, or through other modes of administration, e.g., orally, by injection, topically, nasally or through any other suitable means. The additional pharmaceutical agents are optionally co-administered, or administered at different time periods.

Meniere's Disease

Meniere's disease is characterized by sudden attacks of vertigo, nausea and vomiting that may last for 3 to 24 hours, and may subside gradually. Progressive hearing loss, tinnitus and a sensation of pressure in the ears accompanies the disease through time. The cause of symptoms associated with Meniere's disease is likely an imbalance of inner ear fluid homeostasis, including an increase in production or a decrease in reabsorption of inner ear fluid.

Although the cause of Meniere's disease is unknown, certain evidence suggests a viral etiology for the disease. Specifically, histopathologic analysis of temporal bones in patients with Meniere's disease revealed viral ganglionitis. Also, viral DNA has been observed in the ganglia of patients with Meniere's disease at a higher rate than in healthy patients. Oliveira et al. *ORL* (2008) 70: 42-51. Based on these studies, a pilot study of intratympanic injection of the antiviral agent ganciclovir was conducted, resulting in an improvement of patients suffering from Meniere's disease. Guyot et al. *ORL* (2008) 70: 21-27. Accordingly, controlled release formulations disclosed herein comprising antiviral agents, e.g., ganciclvir, acyclovir, famovir, and valgancyclovir, can be administered to the ear for localized treatment of Meniere's disease.

Other treatments of Meniere's disease are aimed at dealing with the immediate symptoms and prevention of recurrence. Low-sodium diets, avoidance of caffeine, alcohol, and tobacco have been advocated. Medications that temporarily relieve vertigo attacks include antihistamines (e.g., meclizine), and central nervous system agents, including barbiturates and/or benzodiazepines (e.g., lorazepam or diazepam). Other examples of drugs that may be useful in relieving symptoms include muscarinic antagonists, including scopolamine. Nausea and vomiting may be relieved by suppositories containing antipsychotic agents, including the phenothiazine agent prochlorperazine (Compazine®, Buccastem, Stemetil and Phenotil). Thus, other treatments of Meniere's disease are optionally used in combination with the controlled release formulations disclosed herein for the treatment of Meniere's disease.

Surgical procedures have also been used to relieve symptoms of Meniere's disease, including destruction of vestibular function to relieve vertigo symptoms. These procedures aim to either reduce fluid pressure in the inner ear and/or to destroy inner ear balance function. An endolymphatic shunt procedure, which relieves fluid pressure, may be placed in the inner ear to relieve symptoms of vestibular dysfunction. Severing of the vestibular nerve may also be employed, which may control vertigo while preserving hearing.

Another approach to destruction of vestibular function for the treatment of severe Meniere's disease is intratympanic application of an agent that destroys sensory hair cell function in the vestibular system, thereby eradicating inner ear balance function. Various antimicrobial agents are used in the procedure, including aminoglycosides such as gentamicin and streptomycin. The agents are injected through the tympanic membrane using a small needle, a tympanostomy tube with or without a wick, or surgical catheters. Various dosing regimens are used to administer the antimicrobial agents, including a low dose method in which less of the agents are administered over longer periods of time (e.g., one month between injections), and high dose methods in which more of the agents are administered over a shorter time frame (e.g., every week). Although the high dose method is typically more effective, it is more risky, as it may result in hearing loss.

Accordingly, formulations disclosed herein are also useful for administration of antimicrobial agents, e.g., gentamicin and streptomycin, for disabling the vestibular apparatus to treat Meniere's disease. The formulations disclosed herein can be used to maintain a steady release of the active agents inside the tympanic membrane, thereby avoiding the need for multiple injections or the insertion of a tympanostomy tube. Further, by keeping the active agents localized in the vestibular system, the formulations disclosed herein can also be used to administer higher doses of the antimicrobial agents with a decreased risk of hearing loss.

Meniere's Syndrome

Meniere's syndrome, which displays similar symptoms as Meniere's disease, is attributed as a secondary affliction to another disease process, e.g. thyroid disease or inner ear inflammation due to syphilis infection. Meniere's syndrome is thus a collection of secondary effects to various processes that interfere with normal production or resorption of endolymph, including microbial infection. Treatment of patients afflicted with Meniere's syndrome is similar to Meniere's disease.

Vestibular Neuronitis

Vestibular neuronitis is characterized by sudden vertigo attacks, which may present as a single attack of vertigo, a series of attacks, or a persistent condition which diminishes over a matter of weeks. Symptoms typically include nausea, vomiting, and previous upper respiratory tract infections, although there are generally no auditory symptoms. Vestibular neuronitis may also be associated with eye nystagmus, a condition characterized by flickering of the eyes involuntarily toward the affected side. It is caused by inflammation of the vestibular nerve, the nerve that connects the inner ear to the brain, and is likely caused by viral infection. Diagnosis of vestibular neuronitis usually involves tests for nystagmus using electronystamography, a method of electronically recording eye movements. Magnetic resonance imaging may also be performed to determine if other causes may play a role in the vertigo symptoms.

Treatment of vestibular neuronitis typically involves alleviating the symptoms of the condition, primarily vertigo, until the condition clears on its own. Treatment of vertigo is often identical to Meniere's disease, and may include meclizine, lorazepam, prochlorperazine, or scopolamine. Fluids and electrolytes may also be intravenously administered if the vomiting is severe. Corticosteroids, such as prednisilone, are also given if the condition is detected early enough.

Compositions disclosed herein comprising an antiviral agent can be administered for the treatment of vestibular neuronitis. Further, the compositions may be administered with other agents that are typically used to treat symptoms of the condition, including anticholinergics, antihistamines, benzodiazepines, or steroids.

Postural Vertigo

Postural vertigo, otherwise known as positional vertigo, is characterized by sudden violent vertigo that is triggered by certain head positions. This condition may be caused by damaged semicircular canals caused by physical injury to the inner ear, otitis media, ear surgery or blockage of the artery to the inner ear.

Vertigo onset in patients with postural vertigo usually develops when a person lies on one ear or tilts the head back to look up. Vertigo may be accompanied by nystagmus. Treatment of postural vertigo often involves the same treatment as in Meniere's disease. In severe cases of postural vertigo, the vestibular nerve is severed to the affected semicircular canal. Treatment of vertigo is often identical to Meniere's disease, and may include meclizine, lorazepam, prochlorperazine or scopolamine. Fluids and electrolytes may also be intravenously administered if the vomiting is severe.

Sensorineural Hearing Loss

Sensorineural hearing loss occurs when the components of the inner ear or accompanying neural components are affected, and may contain a neural (i.e., the auditory nerve or auditory nerve pathways in the brain are affected) or sensory component. Sensory hearing loss may be hereditary, or it may be caused by acoustic trauma (i.e. very loud noises), a viral infection, drug-induced or Meniere's disease. In some instances, noise induced hearing loss is caused by loud noises, for example, gun fire, loud music or other human-based noise. Neural hearing loss may occur as a result of brain tumors, infections, or various brain and nerve disorders, such as stroke. Some hereditary diseases, such as Refsum's disease (defective accumulation of branched fatty acids), may also cause neural disorders affecting hearing loss. Auditory nerve pathways may be damaged by demyelinating diseases, e.g. idiopathic inflammatory demyelinating disease (including multiple sclerosis), transverse myelitis, Devic's disease, progressive multifocal leukoencephalopathy, Guillain-Barre syndrome, chronic inflammatory demyelinating polyneuropathy and anti-MAG perpheral neuropathy.

The incidence of sudden deafness, or sensorineural hearing loss, occurs in about 1 in 5,000 individuals, and may be caused by viral or bacterial infections, e.g. mumps, measles, influenza, chickenpox, cytomegalovirus, syphilis or infectious mononucleosis, or physical injury to the inner ear organ. In some cases, no cause can be identified Tinnitus and vertigo may accompany sudden deafness, which subsides gradually. Oral corticosteroids are frequently prescribed to treat sensorineural hearing loss. In some cases, surgical intervention may be necessary.

Hereditary Disorders

Hereditary disorders, including Scheibe, Mondini-Michelle, Waardenburg's, Michel, Alexander's ear deformity, hypertelorism, Jervell-Lange Nielson, Refsum's and Usher's syndromes, are found in approximately 20% of patients with sensorineural hearing loss. Congenital ear malformations may result from defects in the development of the membranous labyrinthine, the osseous labyrinthine, or both. Along with profound hearing loss and vestibular function abnormalities, hereditary deformities may also be associated with other dysfunctions, including development of recurring meningitis, cerebral spinal fluid (CSF) leaks, as well as perilymphatic fistulas. Treatment of chronic infections may be necessitated in hereditary disorder patients.

Pharmaceutical Agents

Provided herein are antimicrobial agent compositions and formulations that treat otic disorders and/or their attendant symptoms, including but not limited to infection, hearing loss, nystagmus, vertigo, tinnitus, inflammation, swelling, and congestion. Otic disorders, including AIED, otitis media, otitis externa, Meniere's disease, Ramsay Hunt syndrome, otosyphilis, hereditary disorders and vestibular neuronitis, have causes and symptoms that are responsive to the pharmaceutical agents disclosed herein, or other pharmaceutical agents. Antimicrobial agents that are not disclosed herein but which are useful for the amelioration or eradication of otic disorders are expressly included and intended within the scope of the embodiments presented. In some embodiments, pharmaceutically active metabolites, salts, polymorphs, prodrugs, analogues, and derivatives of the antimicrobial agents disclosed herein that retain the ability of the parent antimicrobial agents to treat otic disorders are useful in the formulations.

Moreover, pharmaceutical agents which have been previously shown to be excessively toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways, or through poor PK characteristics, are useful in some embodiments. Accordingly, pharmaceutical agents which have limited or no systemic release, systemic toxicity, poor PK characteristics or combinations thereof are contemplated within the scope of the embodiments disclosed herein.

The antimicrobial agent formulations disclosed herein are optionally targeted directly to otic structures where treatment is needed. For example, one embodiment contemplated is the direct application of the antimicrobial agent formulations disclosed herein to the auris media through piercing of the intratympanic membrane and applying the antimicrobial agent formulation directly to the auris media structures affected, including the walls of the tympanic cavity or auditory ossicles. By doing so, the antimicrobial agent formulations disclosed herein are confined to the targeted auris media structure, and will not be lost, for example, through leakage through the eustachian tube or pierced tympanic membrane. In some embodiments, the antimicrobial agent formulations are targeted to specific regions of the auris media by application with a needle and syringe, a pump, a microinjection device, or any combination thereof.

Antimicrobial Agent

Some embodiments provided herein describe composition comprising an antimicrobial agent. In some embodiments, the antimicrobial agent is an antibacterial agent. In some embodiments, the antibacterial agent treats infections caused by gram positive bacteria. In some embodiments, the antibacterial agent treats infections caused by gram negative bacteria. In some embodiments, the antibacterial agent treats infections caused by mycobacteria. In some embodiments, the antibacterial agent treats infections caused by giardia. In some embodiments, the antibacterial agent (e.g., ciprofloxacin) treats infections caused by *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof. In some embodiments, the antibacterial agent (e.g., ciprofloxacin) treats infections caused by *Streptococcus pneumoniae, Haemophilus influenzae, Moraxella catarrhalis, Streptococcus pyogenes, Staphylococcus aureus*, or a combination thereof. In some embodiments, the antibacterial agent (e.g., ciprofloxacin) treats infections caused by *Streptococcus pneumonia*. In some embodiments, the antibacterial agent (e.g., ciprofloxacin) treats infections caused by *Haemophilus influenzae*. In some embodiments, the antibacterial agent (e.g., ciprofloxacin) treats infections caused by *Moraxella catarrhalis*.

In some embodiments, the antibacterial agent treats infections by inhibiting bacterial protein synthesis. In some embodiments, the antibacterial agent treats infections by disrupting synthesis of bacterial cell wall. In some embodiments, the antibacterial agent treats infections by changing permeability of bacterial cell membranes. In some embodiments, the antibacterial agent treats infections by disrupting DNA replication in bacteria.

In some embodiments, the antibacterial agent is an antibiotic. In some embodiments, the antibiotic is a quinolone. In specific embodiments, the antibiotic is ciprofloxacin. In some embodiments, the antibiotic is micronized ciprofloxacin. In some embodiments, an antibiotic compatible with the compositions described herein is a broad spectrum antibiotic. In some embodiments, an antibiotic compatible with the compositions described herein is effective in treating infections that are resistant to other classes of antibiotics. In some embodiments, intratympanic administration of an antibiotic composition described herein reduces the risk of development of antibiotic resistance that is seen with systemic treatments.

Concentration of Active Agent

In some embodiments, the compositions described herein have a concentration of active pharmaceutical ingredient between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the active ingredient, or pharmaceutically acceptable prodrug or salt thereof, by weight of the composition. In some embodiments, the compositions described herein have a concentration of active pharmaceutical agent, or pharmaceutically acceptable prodrug or salt thereof, between about 1% to about 50%, between about 5% to about 50%, between about 10% to about 40%, or between about 10% to about 30%, of the active ingredient, or pharmaceutically acceptable prodrug or salt thereof, by weight of the composition. In some embodiments, formulations described herein comprise about 70% by weight of an antimicrobial agent, or pharmaceutically acceptable prodrug or salt thereof, by weight of the formulation. In some embodiments, formulations described herein comprise about 60% by weight of an antimicrobial agent, or pharmaceutically acceptable prodrug or salt thereof, by weight of the formulation. In some embodiments, formulations described herein comprise about 50% by weight of an antimicrobial agent, or pharmaceutically acceptable prodrug or salt thereof, by weight of the formulation. In some embodiments, formulations described herein comprise about 40% by weight of an antimicrobial agent, or pharmaceutically acceptable prodrug or salt thereof, by weight of the formulation. In some embodiments, formulations described herein comprise about 30% by weight, or pharmaceutically acceptable prodrug or salt thereof, of an antimicrobial agent by weight of the formulation. In some embodiments, formulations described herein comprise about 20% by weight of an antimicrobial agent, or pharmaceutically acceptable prodrug or salt thereof, by weight of the formulation. In some embodiments, formulations described herein comprise about 15% by weight of an antimicrobial agent, or pharmaceutically acceptable prodrug or salt thereof, by weight of the formulation. In some embodiments, formulations described herein comprise about 10% by weight of an antimicrobial agent by weight of the formulation. In some embodiments, formulations described herein comprise about 5% by weight of an antimicrobial agent, or pharmaceutically acceptable prodrug or salt thereof, by weight of the formulation. In some embodiments, formulations described herein comprise about 2.5% by weight of an antimicrobial agent, or pharmaceutically acceptable prodrug or salt thereof, by weight of the formulation. In some embodiments, formulations described herein comprise about 1% by weight of an antimicrobial agent, or pharmaceutically acceptable prodrug or salt thereof, by weight of the formulation. In some embodiments, formulations described herein comprise about 0.5% by weight of an antimicrobial agent, or pharmaceutically acceptable prodrug or salt thereof, by weight of the formulation. In some embodiments, formulations described herein comprise about 0.1% by weight of an antimicrobial agent, or pharmaceutically acceptable prodrug or salt thereof, by weight of the formulation. In some embodiments, formulations described herein comprise about 0.01% by weight of an antimicrobial agent, or pharmaceutically acceptable prodrug or salt thereof, by weight of the formulation. In some embodiments, the formulations described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the formulation.

In some embodiments, the composition comprises 1-8% by weight of micronized ciprofloxacin. In some embodiments, the composition comprises 1.8 to 6.6% by weight of micronized ciprofloxacin. In some embodiments, the composition comprises 1.8-2.2% by weight of micronized ciprofloxacin. In other embodiments, the composition comprises 5.4-6.6% by weight of micronized ciprofloxacin. In some embodiments, the composition comprises about 1%, about 1.1% about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0% by weight of micronized ciprofloxacin. In some specific embodiments, the composition comprises about 1.8% by weight of micronized ciprofloxacin. In some specific embodiments, the composition comprises about 1.9% by weight of micronized ciprofloxacin. In some specific embodiments, the composition comprises about 2.0% by weight of micronized ciprofloxacin. In some specific embodiments, the composition comprises about 2.1% by weight of micronized ciprofloxacin. In some specific embodiments, the composition comprises 2.2% by weight of micronized ciprofloxacin. In some specific embodiments, the composition comprises 5.4% by weight of micronized ciprofloxacin. In some specific embodiments, the composition comprises 5.5% by weight of micronized ciprofloxacin. In some specific embodiments, the composition comprises 5.6% by weight of micronized ciprofloxacin. In some specific embodiments, the composition comprises 5.7% by weight of micronized ciprofloxacin. In some specific embodiments, the composition comprises 5.8% by weight of micronized ciprofloxacin. In some specific embodiments, the composition comprises 5.9% by weight of micronized ciprofloxacin. In some specific embodiments, the composition comprises 6.0% by weight of micronized ciprofloxacin. In some specific embodiments, the composition comprises 6.1% by weight of micronized ciprofloxacin. In some specific embodiments, the composition comprises 6.2% by weight of micronized ciprofloxacin. In some specific embodiments, the composition comprises 6.3% by weight of micronized ciprofloxacin. In some specific embodiments, the composition comprises 6.4% by weight of micronized ciprofloxacin. In some specific embodiments, the composition comprises 6.5% by weight of micronized ciprofloxacin. In some specific embodiments, the composition comprises 6.6% by weight of micronized ciprofloxacin.

Pharmaceutical Formulations

Provided herein are pharmaceutical compositions or devices that include at least one antimicrobial agent (e.g., ciprofloxacin) and a pharmaceutically acceptable diluent(s), excipient(s), or carrier(s). In some embodiments, the pharmaceutical compositions include other medicinal or pharmaceutical agents, carriers, adjuvants, such as salts for regulating the osmotic pressure, and/or buffers. In other embodiments, the pharmaceutical compositions also contain other therapeutic substances. In some embodiments, the pharmaceutical compositions are preservative-free.

In some embodiments, the auris-compatible formulations described herein are free of preservatives. In some embodiments, any of the formulations described herein are free of sodium bisulfite, sodium thiosulfate, ascorbate, chorobutanol, thimerosal, parabens, benzyl alcohol, Butylated hydroxytoluene (BHT), and phenylethanol. In certain embodiments, any of the formulations described herein are free of BHT.

pH and Practical Osmolarity

In some embodiments, an otic composition or device disclosed herein is formulated to provide an ionic balance that is compatible with inner ear fluids (e.g., endolymph and/or perilymph).

In certain instances, the ionic composition of the endolymph and perilymph regulate the electrochemical impulses of hair cells and thus hearing. In certain instances, changes in the conduction of electrochemical impulses along otic hair cells results in hearing loss. In certain instances, changes in the ionic balance of the endolymph or perilymph results in complete hearing loss. In certain instances, changes in the ionic balance of the endolymph or perilymph results in partial hearing loss. In certain instances, changes in the ionic balance of the endolymph or perilymph results in permanent hearing loss. In certain instances, changes in the ionic balance of the endolymph or perilymph results in temporary hearing loss.

In some embodiments, a composition or device disclosed herein is formulated in order to not disrupt the ionic balance of the endolymph. In some embodiments, a composition or device disclosed herein has an ionic balance that is the same as or substantially the same as the endolymph. In some embodiments, a composition or device disclosed herein does not does not disrupt the ionic balance of the endolymph so as to result in partial or complete hearing loss. In some embodiments, a composition or device disclosed herein does not does not disrupt the ionic balance of the endolymph so as to result in temporary or permanent hearing loss.

In some embodiments, a composition or device disclosed herein does not substantially disrupt the ionic balance of the perilymph. In some embodiments, a composition or device disclosed herein has an ionic balance that is the same as or substantially the same as the perilymph. In some embodiments, a composition or device disclosed herein does not result in partial or complete hearing loss as the composition or device does not disrupt the ionic balance of the perilymph. In some embodiments, a composition or device disclosed herein does not result in temporary or permanent hearing loss as the composition or device does not disrupt the ionic balance of the perilymph.

As used herein, "practical osmolarity/osmolality" or "deliverable osmolarity/osmolality" means the osmolarity/osmolality of a composition or device as determined by measuring the osmolarity/osmolality of the active agent and all excipients except the gelling and/or the thickening agent (e.g., polyoxyethylene-polyooxypropylene copolymers, carboxymethylcellulose or the like). The practical osmolarity of a composition or device disclosed herein is measured by a suitable method, e.g., a freezing point depression method as described in Viegas et. al., *Int. J. Pharm.*, 1998, 160, 157-162. In some instances, the practical osmolarity of a composition or device disclosed herein is measured by vapor pressure osmometry (e.g., vapor pressure depression method) that allows for determination of the osmolarity of a composition or device at higher temperatures. In some instances, vapor pressure depression method allows for determination of the osmolarity of a composition or device comprising a gelling agent (e.g., a thermoreversible polymer) at a higher temperature wherein the gelling agent is in the form of a gel.

In some embodiments, the osmolarity at a target site of action (e.g., the perilymph) is about the same as the delivered osmolarity (i.e., osmolarity of materials that cross or penetrate the round window membrane) of a composition or device described herein. In some embodiments, a composition or device described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an otic composition or device disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition or device described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0. In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

Some embodiments provided herein describe an antimicrobial composition further comprising an osmolality modifier, pH adjusting agent, and a buffering agent. In some embodiments, the antimicrobial composition comprises hydrochloric acid as a pH adjusting agent. In some embodiments, the antimicrobial composition comprises tromethamine as a buffering agent. In some embodiments, the antimicrobial composition comprises sodium chloride as an osmolality modifier. In certain embodiments, the antimicrobial composition consists of ciprofloxacin, poloxamer 407, water, an osmolality modifier (e.g., sodium chloride), a pH adjusting agent (e.g., hydrochloric acid), and a buffering agent (e.g., tromethamine).

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g, by filtration or aseptic mixing or heat treatment and/or autoclaving (e.g., terminal sterilization) of a gel formulation without degradation of the pharmaceutical agent (e.g., antimicrobial agent) or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for sterilization (e.g, by heat treatment and/or autoclaving) of a gel formulation without degradation of the pharmaceutical agent (e.g., antimicrobial agent) or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g, by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g, by filtration or aseptic mixing or heat treatment and/or autoclaving (e.g., terminal sterilization)) of any composition described herein.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any formulation described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L; and preferably about 270 to about 320 mOsm/L. In specific embodiments, auris compositions described herein are formulated to provide a delivered perilymph-suitable osmolality at the target site of action of about 250 to about 320 mOsm/kg $H_2O$; or an osmolality of about 270 to about 320 mOsm/kg $H_2O$. In specific embodiments, the deliverable osmolarity/osmolality of the formulations (i.e., the osmolarity/osmolality of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., perilymph) that causes minimal disturbance to the environment of the inner ear and causes minimum discomfort (e.g., vertigo and/or nausea) to a mammal upon administration.

In some embodiments, any formulation described herein is isotonic with the perilymph and/or endolymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes. In some embodiments, tonicity agents are non-ototoxic.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the formulations described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and/or practical osmolarity as described herein, and have a concentration of active pharmaceutical ingredient between about 0.01%-about 20%, between about 0.01%-about 10%, between about 0.01%-about 7.5%, between about 0.01%-6%, between about 0.01-5%, between about 0.1-about 10%, or between about 0.1-about 6% of the active ingredient by weight of the formulation. In some embodiments, the formulations described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation. In some embodiments, the formulations described herein have a pH and/or practical osmolarity as described herein, and have a concentration of active pharmaceutical ingredient between about 1 µg/mL and about 500 µg/mL, between about 1 µg/mL and about 250 µg/mL, between about 1 µg and about 100 µg/mL, between about 1 µg/mL and about 50 µg/mL, or between about 1 µg/mL and about 20 µg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e., the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 µm to about 100 µm. In some embodiments, the average diameter of particles in a micronized solid is from about 3 µm to about 50 µm. In some embodiments, a particulate micronized solid comprises particle sizes of less than about 5 microns, less than about 20 microns and/or less than about 100 microns.

In some embodiments, the use of particulates (e.g., micronized particles) of antimicrobial agent allows for extended and/or sustained release of the antimicrobial agent from any formulation described herein compared to a formulation comprising non-multiparticulate (e.g, non-micronized) antimicrobial agent. In some instances, formulations containing multiparticulate (e.g. micronized) antimicrobial agent are ejected from a 1 mL syringe adapted with a 27 G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

In some embodiments, a formulation described herein comprises one or more antimicrobial agents wherein the antimicrobial agent comprises nanoparticulates. In some embodiments, a formulation described herein comprises antimicrobial agent beads (e.g., vancomycin beads) that are optionally coated with controlled release excipients. In some embodiments, a formulation described herein comprises an antimicrobial agent that is granulated and/or reduced in size and coated with controlled release excipients; the granulated coated antimicrobial agent particulates are then optionally micronized and/or formulated in any of the compositions described herein.

In some instances, a combination of an antimicrobial agent as a neutral molecule, free acid or free base and/or a salt of the antimicrobial agent is used to prepare pulsed release otic agent formulations using the procedures described herein. In some formulations, a combination of a micronized antimicrobial agent (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the antimicrobial agent (e.g., micronized antimicrobial agent, free base, free acid or salt or prodrug thereof; multiparticulate antimicrobial agent, free base, free acid or salt or prodrug thereof) with the aid of cyclodextrins, surfactants (e.g., poloxamers (407, 338, 188), tween (80, 60, 20,81), PEG-hydrogenated castor oil, cosolvents like N-methyl-2-Pyrrolidone or the like and preparing pulsed release formulations using any procedure described herein.

In specific embodiments, any auris-compatible formulation described herein comprises one or more micronized pharmaceutical agents (e.g., antimicrobial agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises an antimicrobial agent as a neutral molecule, a free acid, a free base, a salt, a prodrug or any combination thereof. In certain embodiments, a pharmaceutical composition described herein comprises an antimicrobial agent as a micronized powder. In certain embodiments, a pharmaceutical composition described herein comprises an antimicrobial agent in the form of a micronized antimicrobial agent powder.

The multiparticulates and/or micronized antimicrobial agents described herein are delivered to an auris structure (e.g., inner ear) by means of any type of matrix including solid, liquid or gel matrices. In some embodiments, the multiparticulates and/or micronized antimicrobial agents described herein are delivered to an auris structure (e.g., inner ear) by means of any type of matrix including solid, liquid or gel matrices via intratympanic injection.

Tunable Release Characteristics

The release of active agent from any formulation, composition or device described herein is optionally tunable to the desired release characteristics. In some embodiments, a composition described herein is a solution that is substantially free of gelling components. In such instances, the composition provides essentially immediate release of an active agent. In some of such embodiments, the composition is useful in perfusion of otic structures, e.g., during surgery.

In some embodiments, a composition described herein is a solution that is substantially free of gelling components and comprises micronized otic agent (e.g., a corticosteroid, an antimicrobial agent or the like). In some of such embodiments, the composition provides release of an active agent from about 2 days to about 4 days.

In some embodiments, a composition described herein comprises a gelling agent (e.g., poloxamer 407) and provides release of an active agent over a period of from about 1 day to about 3 days. In some embodiments, a composition described herein comprises a gelling agent (e.g., poloxamer 407) and provides release of an active agent over a period of from about 1 day to about 5 days. In some embodiments, a composition described herein comprises a gelling agent (e.g., poloxamer 407) and provides release of an active agent over a period of from about 2 days to about 7 days.

In some embodiments, a composition described herein comprises a thermoreversible polymer (e.g., poloxamer 407) in combination with micronized otic agent (e.g., ciprofloxacin) and provides extended sustained release over a longer period of time. In some embodiments, a composition described herein comprises about 14-17% of a thermoreversible polymer (e.g., poloxamer 407) and micronized otic agent (e.g., ciprofloxacin), and provides extended sustained release over a period of from about 1 week to about 3 weeks. In some embodiments, a composition described herein comprises about 18-21% of a thermoreversible polymer (e.g., poloxamer 407) and micronized otic agent (e.g., ciprofloxacin), and provides extended sustained release over a period of from about 3 weeks to about 6 weeks. In some embodiments, a composition described herein comprises about 15-17% by weight of a thermoreversible polymer (e.g., poloxamer 407). In some embodiments, a composition described herein comprises about 14.4-17.6% by weight of a thermoreversible polymer (e.g., poloxamer 407). In some embodiments, a composition described herein comprises about 15.5-16.5% by weight of a thermoreversible polymer (e.g., poloxamer 407). In some embodiments, a composition described herein comprises about 14.4%, about 14.6%, about 14.8%, about 15%, about 15.1%, about 15.2%, about 15.3%, about 15.4%, about 15.5%, about 15.6%, about 15.7%, about 15.8%, about 15.9%, about 16%, about 16.1%, about 16.2%, about 16.3%, about 16.4%, about 16.5%, about 16.6%, about 16.7%, about 16.8%, about 16.9%, about 17%, about 17.2%, about 17.4%, about 17.6%, about 17.8%, about 18% by weight of a thermoreversible polymer (e.g., poloxamer 407). In some embodiments, a composition described herein comprises about 15% by weight of a thermoreversible polymer (e.g., poloxamer 407). In some embodiments, a composition described herein comprises about 15.5% by weight of a thermoreversible polymer (e.g., poloxamer 407). In some embodiments, a composition described herein comprises about 16% by weight of a thermoreversible polymer (e.g., poloxamer 407). In some embodiments, a composition described herein comprises about 16.5% by weight of a thermoreversible polymer (e.g., poloxamer 407). In some embodiments, a composition described herein comprises about 17% by weight of a thermoreversible polymer (e.g., poloxamer 407).

Accordingly, the amount of gelling agent in a composition, and the particle size of an otic agent are tunable to the desired release profile of an otic agent from the composition.

As described herein, compositions comprising micronized otic agents (e.g., ciprofloxacin) provide extended release over a longer period of time compared to compositions comprising non-micronized otic agents. In some instances, the micronized otic agent (e.g., ciprofloxacin) provides a steady supply (e.g., +/−20%) of active agent via slow degradation and serves as a depot for the active agent; such a depot effect increases residence time of the otic agent in the ear. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

In some embodiments, the viscosity of any formulation described herein is designed to provide a suitable rate of release from an auris compatible gel. In some embodiments, the concentration of a thickening agent (e.g., gelling components such as polyoxyethylene-polyoxypropylene copolymers) allows for a tunable mean dissolution time (MDT). The MDT is inversely proportional to the release rate of an active agent from a composition or device described herein. Experimentally, the released otic agent is optionally fitted to the Korsmeyer-Peppas equation $$\frac{Q}{Q_\alpha} = kt^n + b$$

where Q is the amount of otic agent released at time t, $Q\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is optionally calculated by:

$$MDT = \frac{nk^{-1/n}}{n+1}$$

For example, a linear relationship between the mean dissolution time (MDT) of a composition or device and the concentration of the gelling agent (e.g., poloxamer) indicates that the otic agent is released due to the erosion of the polymer gel (e.g., poloxamer) and not via diffusion. In another example, a non-linear relationship indicates release of otic agent via a combination of diffusion and/or polymer gel degradation. In another example, a faster gel elimination time course of a composition or device (a faster release of active agent) indicates lower mean dissolution time (MDT). The concentration of gelling components and/or active agent in a composition are tested to determine suitable parameters for MDT. In some embodiments, injection volumes are also tested to determine suitable parameters for preclinical and clinical studies. The gel strength and concentration of the active agent affects release kinetics of an otic agent from the composition. At low poloxamer concentration, elimination rate is accelerated (MDT is lower). An increase in otic agent concentration in the composition or device prolongs residence time and/or MDT of the otic agent in the ear.

In some embodiments, the MDT for poloxamer from a composition or device described herein is at least 6 hours. In some embodiments, the MDT for poloxamer from a composition or device described herein is at least 10 hours.

In some embodiments, the MDT for an active agent from a composition or device described herein is from about 30 hours to about 48 hours. In some embodiments, the MDT for an active agent from a composition or device described herein is from about 30 hours to about 96 hours. In some embodiments, the MDT for an active agent from a composition or device described herein is from about 30 hours to about 1 week. In some embodiments, the MDT for a composition or device described herein is from about 1 week to about 6 weeks.

In some embodiments, the mean residence time (MRT) for an active agent in a composition or device described herein is from about 20 hours to about 48 hours. In some embodiments, the MRT for an active agent from a composition or device described herein is from about 20 hours to about 96 hours. In some embodiments, the MRT for an active agent from a composition or device described herein is from about 20 hours to about 1 week.

In some embodiments, the MRT for an active agent is about 20 hours. In some embodiments, the MRT for an active agent is about 30 hours. In some embodiments, the MRT for an active agent is about 40 hours. In some embodiments, the MRT for an active agent is about 50 hours. In some embodiments, the MRT for an active agent is about 60 hours. In some embodiments, the MRT for an active agent is about 70 hours. In some embodiments, the MRT for an active agent is about 80 hours. In some embodiments, the MRT for an active agent is about 90 hours. In some embodiments, the MRT for an active agent is about 1 week. In some embodiments, the MRT for an active agent is about 90 hours. In some embodiments, the MRT for a composition or device described herein is from about 1 week to about 6 weeks. In some embodiments, the MRT for an active agent is about 1 week. In some embodiments, the MRT for an active agent is about 2 weeks. In some embodiments, the MRT for an active agent is about 3 weeks. In some embodiments, the MRT for an active agent is about 4 weeks. In some embodiments, the MRT for an active agent is about 5 weeks. The half life of an otic agent and mean residence time of the otic agent are determined for each formulation by measurement of concentration of the otic agent in the perilymph using procedures described herein.

In some embodiments, the use of a composition comprising micronized ciprofloxacin described herein for the treatment of middle ear effusion provides a middle ear MRT of 150 to 300 h. In some embodiments, the use of a composition comprising micronized ciprofloxacin described herein for the treatment of middle ear effusion provides a middle ear MRT of 175 to 275 h. In some embodiments, the use of a composition comprising micronized ciprofloxacin described herein for the treatment of middle ear effusion provides a middle ear MRT of 200 to 250 h. In some embodiments, the use of a composition comprising micronized ciprofloxacin described herein for the treatment of middle ear effusion provides a middle ear MRT of 160 to 190 h. In some embodiments, the use of a composition comprising micronized ciprofloxacin described herein for the treatment of middle ear effusion provides a middle ear MRT of 170 to 180 h. In some embodiments, the use of a composition comprising micronized ciprofloxacin described herein for the treatment of middle ear effusion provides a middle ear MRT of 250 to 300 h. In some embodiments, the use of a composition comprising micronized ciprofloxacin described herein for the treatment of middle ear effusion provides a middle ear MRT of 265 to 285 h. In some embodiments, the use of a composition comprising micronized ciprofloxacin described herein for the treatment of middle ear effusion provides a middle ear MRT of about 175 h, about 180 h, about 185 h, about 190 h, about 195 h, about 200 h, about 210 h, about 220 h, about 225 h, about 230 h, about 240 h, about 250 h, about 260 h, about 270 h, or about 275 h.

In certain embodiments, any controlled release otic formulation described herein increases the exposure of an otic agent and increases the Area Under the Curve (AUC) in otic fluids (e.g., endolymph and/or perilymph) by about 30%, about 40%, about 50%, about 60%, about 70%, about 80% or about 90% compared to a formulation that is not a controlled release otic formulation.

In certain embodiments, any controlled release otic formulation described herein increases the exposure time of an otic agent and decreases the Cmax in otic fluids (e.g., endolymph and/or perilymph) by about 40%, about 30%, about 20%, or about 10%, compared to a formulation that is not a controlled release otic formulation. In certain embodiments, any controlled release otic formulation described herein alters (e.g. reduces) the ratio of Cmax to Cmin compared to a formulation that is not a controlled release otic formulation. In certain embodiments, any controlled release otic formulation described herein increases the exposure of an otic agent and increases the length of time that the concentration of an otic agent is above Cmin by about 30%, about 40%, about 50%, about 60%, about 70%, about 80% or about 90% compared to a formulation that is not a controlled release otic formulation. In certain instances, controlled release formulations described herein delay the time to Cmax. In certain instances, the controlled steady release of a drug prolongs the time the concentration of the drug will stay above the Cmin. In some embodiments, auris compositions described herein prolong the residence time of a drug in the inner ear and provide a stable drug exposure profile. In some instances, an increase in concentration of an active agent in the composition saturates the clearance process and allows for a more rapid and stable steady state to be reached.

In some embodiments, the use of a composition comprising micronized ciprofloxacin described herein for the treatment of middle ear effusion provides exposure to high and stable ciprofloxacin concentrations in the middle ear compartment. In some embodiments, the use of a composition comprising micronized ciprofloxacin described herein for the treatment of middle ear effusion provides a middle ear ciprofloxacin $C_{max}$ of 50 to 125 µg/mL. In some embodiments, the use of a composition comprising micronized ciprofloxacin described herein for the treatment of middle ear effusion provides a middle ear ciprofloxacin $C_{max}$ of 75 to 100 µg/mL. In some embodiments, the use of a composition comprising micronized ciprofloxacin described herein for the treatment of middle ear effusion provides a middle ear ciprofloxacin $C_{max}$ of about 75 µg/mL, about 80 µg/mL, about 85 µg/mL, about 90 µg/mL, about 95 µg/mL, or about 100 µg/mL. In some embodiments, the use of a composition comprising micronized ciprofloxacin described herein for the treatment of middle ear effusion provides a middle ear ciprofloxacin $C_{max}$ of at least 50 µg/mL, at least 75 µg/mL, at least 80 µg/mL, at least 85 µg/mL, at least 90 µg/mL, at least 95 µg/mL, or at least 100 µg/mL. In some embodiments, the use of a composition comprising micronized ciprofloxacin described herein for the treatment of middle ear effusion provides a middle ear ciprofloxacin $C_{max}$ of at least 50 µg/mL. In some embodiments, the use of a composition comprising micronized ciprofloxacin described herein for the treatment of middle ear effusion provides a middle ear ciprofloxacin $C_{max}$ of at least 60 µg/mL. In some embodiments, the use of a composition comprising micronized ciprofloxacin described herein for the treatment of middle ear effusion provides a middle ear ciprofloxacin $C_{max}$ of at least 75 µg/mL.

In some embodiments, the use of a composition comprising micronized ciprofloxacin described herein for the treatment of middle ear effusion provides a middle ear ciprofloxacin AUC of 7,500 to 50,000 µg·h/mL. In certain embodiments, the use of a composition comprising micronized ciprofloxacin described herein for the treatment of middle ear effusion provides a middle ear ciprofloxacin AUC of 10,000 to 25,000 µg·h/mL. In certain embodiments, the use of a composition comprising micronized ciprofloxacin described herein for the treatment of middle ear effusion provides a middle ear ciprofloxacin AUC of about 10,000 µg·h/mL, 12,000 µg·h/mL, about 15,000 µg·h/mL, about 17,000 µg·h/mL, about 20,000 µg·h/mL, about 22,000 µg·h/mL, or about 25,000 µg·h/mL. In certain embodiments, the use of a composition comprising micronized ciprofloxacin described herein for the treatment of middle ear effusion provides a middle ear ciprofloxacin AUC of about 10,000 µg·h/mL. In certain embodiments, the use of a composition comprising micronized ciprofloxacin described herein for the treatment of middle ear effusion provides a middle ear ciprofloxacin AUC of about 15,000 µg·h/mL. In certain embodiments, the use of a composition comprising micronized ciprofloxacin described herein for the treatment of middle ear effusion provides a middle ear ciprofloxacin AUC of about 17,000 µg·h/mL. In certain embodiments, the use of a composition comprising micronized ciprofloxacin described herein for the treatment of middle ear effusion provides a middle ear ciprofloxacin AUC of about 20,000 µg·h/mL. In certain embodiments, the use of a composition comprising micronized ciprofloxacin described herein for the treatment of middle ear effusion provides a middle ear ciprofloxacin AUC of about 25,000 µg·h/mL.

In some embodiments, the use of a composition comprising micronized ciprofloxacin described herein for the treatment of middle ear effusion provides a middle ear ciprofloxacin $AUC_{0-24}$ of 1,000 to 3,000 µg·h/mL. In certain embodiments, the use of a composition comprising micronized ciprofloxacin described herein for the treatment of middle ear effusion provides a middle ear ciprofloxacin $AUC_{0-24}$ of 2,000 to 2,500 µg·h/mL. In certain embodiments, the use of a composition comprising micronized ciprofloxacin described herein for the treatment of middle ear effusion provides a middle ear ciprofloxacin $AUC_{0-24}$ of about 1,000 µg·h/mL, 1,200 µg·h/mL, about 1,400 µg·h/mL, about 1,600 pg·h/mL, about 1,800 µg·h/mL, about 2,000 µg·h/mL, about 2,100 µg·h/mL, about 2,200 µg·h/mL, about 2,300 µg·h/mL, about 2,400 µg·h/mL, about 2,500 µg·h/mL, about 2,600 µg·h/mL, about 2,700 µg·h/mL, about 2,800 µg·h/mL, or about 3,000 µg·h/mL. In certain embodiments, the use of a composition comprising micronized ciprofloxacin described herein for the treatment of middle ear effusion provides a middle ear ciprofloxacin $AUC_{0-24}$ of about 2,000 µg·h/mL. In certain embodiments, the use of a composition comprising micronized ciprofloxacin described herein for the treatment of middle ear effusion provides a middle ear ciprofloxacin $AUC_{0-24}$ of about 2,100 µg·h/mL. In certain embodiments, the use of a composition comprising micronized ciprofloxacin described herein for the treatment of middle ear effusion provides a middle ear ciprofloxacin $AUC_{0-24}$ of about 2,200 µg·h/mL. In certain embodiments, the use of a composition comprising micronized ciprofloxacin described herein for the treatment of middle ear effusion provides a middle ear ciprofloxacin $AUC_{0-24}$ of about 2,300 µg·h/mL. In certain embodiments, the use of a composition comprising micronized ciprofloxacin described herein for the treatment of middle ear effusion provides a middle ear ciprofloxacin $AUC_{0-24}$ of about 2,400 µg·h/mL. In certain embodiments, the use of a composition comprising micronized ciprofloxacin described herein for the treatment of middle ear effusion provides a middle ear ciprofloxacin $AUC_{0-24}$ of about 2,500 µg·h/mL.

In some embodiments, the use of a composition comprising micronized ciprofloxacin described herein for the treatment of middle ear effusion provides a middle ear ciprofloxacin T>MIC (time of ciprofloxacin above minimum inhibitory concentration) of about 350 to 800 h. In some embodiments, the use of a composition comprising micronized ciprofloxacin described herein for the treatment of middle ear effusion provides a middle ear ciprofloxacin T>MIC of about 400 to 730 h. In some embodiments, the use of a composition comprising micronized ciprofloxacin described herein for the treatment of middle ear effusion provides a middle ear ciprofloxacin T>MIC of about 400 h, about 425 h, about 450 h, about 475 h, about 500 h, about 525 h, about 550 h, about 575 h, about 600 h, about 625 h, about 650 h, about 675 h, about 700 h, about 725 h, or about 730 h. In some embodiments, the use of a composition comprising micronized ciprofloxacin described herein for the treatment of middle ear effusion provides a middle ear ciprofloxacin T>MIC of about 450 h. In some embodiments, the use of a composition comprising micronized ciprofloxacin described herein for the treatment of middle ear effusion provides a middle ear ciprofloxacin T>MIC of about 500 h. In some embodiments, the use of a composition comprising micronized ciprofloxacin described herein for the treatment of middle ear effusion provides a middle ear ciprofloxacin T>MIC of about 550 h. In some embodiments, the use of a composition comprising micronized ciprofloxacin described herein for the treatment of middle ear effusion provides a middle ear ciprofloxacin T>MIC of about 600 h. In some embodiments, the use of a composition comprising micronized ciprofloxacin described herein for the treatment of middle ear effusion provides a middle ear ciprofloxacin T>MIC of about 650 h.

In some embodiments, the use of a composition comprising micronized ciprofloxacin described herein for the treatment of middle ear effusion provides a middle ear ciprofloxacin $C_{max}$/MIC (minimum inhibitory concentration) ratio of 40 to 50. In some embodiments, the use of a composition comprising micronized ciprofloxacin described herein for the treatment of middle ear effusion provides a middle ear ciprofloxacin $C_{max}$/MIC ratio of about 40. In some embodiments, the use of a composition comprising micronized ciprofloxacin described herein for the treatment of middle ear effusion provides a middle ear ciprofloxacin $C_{max}$/MIC ratio of about 42. In some embodiments, the use of a composition comprising micronized ciprofloxacin described herein for the treatment of middle ear effusion provides a middle ear ciprofloxacin $C_{max}$/MIC ratio of about 44. In some embodiments, the use of a composition comprising micronized ciprofloxacin described herein for the treatment of middle ear effusion provides a middle ear ciprofloxacin $C_{max}$/MIC ratio of about 46. In some embodiments, the use of a composition comprising micronized ciprofloxacin described herein for the treatment of middle ear effusion provides a middle ear ciprofloxacin $C_{max}$/MIC ratio of about 48. In some embodiments, the use of a composition comprising micronized ciprofloxacin described herein for the treatment of middle ear effusion provides a middle ear ciprofloxacin $C_{max}$/MIC ratio of about 50. In some embodiments, the use of a composition comprising micronized ciprofloxacin described herein for the treatment of middle ear effusion provides a middle ear ciprofloxacin $C_{max}$/MIC (minimum inhibitory concentration) ratio of at least 10. In some embodiments, the use of a composition comprising micronized ciprofloxacin described herein for the treatment of middle ear effusion provides a middle ear ciprofloxacin $C_{max}$/MIC (minimum inhibitory concentration) ratio of at least 20. In some embodiments, the use of a composition comprising micronized ciprofloxacin described herein for the treatment of middle ear effusion provides a middle ear ciprofloxacin $C_{max}$/MIC (minimum inhibitory concentration) ratio of at least 30. In some embodiments, the use of a composition comprising micronized ciprofloxacin described herein for the treatment of middle ear effusion provides a middle ear ciprofloxacin $C_{max}$/MIC (minimum inhibitory concentration) ratio of at least 40.

In some embodiments, the use of a composition comprising micronized ciprofloxacin described herein for the treatment of middle ear effusion provides a middle ear ciprofloxacin $AUC_{0-24}$/MIC (minimum inhibitory concentration) ratio of 1000 to 1200. In some embodiments, the use of a composition comprising micronized ciprofloxacin described herein for the treatment of middle ear effusion provides a middle ear ciprofloxacin $AUC_{0-24}$/MIC ratio of about 900. In some embodiments, the use of a composition comprising micronized ciprofloxacin described herein for the treatment of middle ear effusion provides a middle ear ciprofloxacin $AUC_{0-24}$/MIC ratio of about 1000. In some embodiments, the use of a composition comprising micronized ciprofloxacin described herein for the treatment of middle ear effusion provides a middle ear ciprofloxacin $AUC_{0-24}$/MIC ratio of about 1050. In some embodiments, the use of a composition comprising micronized ciprofloxacin described herein for the treatment of middle ear effusion provides a middle ear ciprofloxacin $AUC_{0-24}$/MIC ratio of about 1100. In some embodiments, the use of a composition comprising micronized ciprofloxacin described herein for the treatment of middle ear effusion provides a middle ear ciprofloxacin $AUC_{0-24}$/MIC ratio of about 1150. In some embodiments, the use of a composition comprising micronized ciprofloxacin described herein for the treatment of middle ear effusion provides a middle ear ciprofloxacin $AUC_{0-24}$/MIC ratio of about 1200. In some embodiments, the use of a composition comprising micronized ciprofloxacin described herein for the treatment of middle ear effusion provides a middle ear ciprofloxacin $AUC_{0-24}$/MIC (minimum inhibitory concentration) ratio of at least 100. In some embodiments, the use of a composition comprising micronized ciprofloxacin described herein for the treatment of middle ear effusion provides a middle ear ciprofloxacin $AUC_{0-24}$/MIC (minimum inhibitory concentration) ratio of at least 250. In some embodiments, the use of a composition comprising micronized ciprofloxacin described herein for the treatment of middle ear effusion provides a middle ear ciprofloxacin $AUC_{0-24}$/MIC (minimum inhibitory concentration) ratio of at least 500. In some embodiments, the use of a composition comprising micronized ciprofloxacin described herein for the treatment of middle ear effusion provides a middle ear ciprofloxacin $AUC_{0-24}$/MIC (minimum inhibitory concentration) ratio of at least 1000.

In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, or 1 week, 3 weeks, 6 weeks, 2 months). In some embodiments, the steady state concentration of active agent released from a controlled release formulation described herein is about 5 to about 20 times the steady state concentration of an active agent released from a formulation that is not a controlled release formulation. In some embodiments, the steady state concentration of active agent released from a controlled release formulation described herein is about 20 to about 50 times the steady state concentration of an active agent released from a formulation that is not a controlled release formulation.

Controlled Release Formulations

In general, controlled release drug formulations impart control over the release of drug with respect to site of release and time of release within the body. As discussed herein, controlled release refers to immediate release, delayed release, sustained release, extended release, variable release, pulsatile release and bi-modal release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

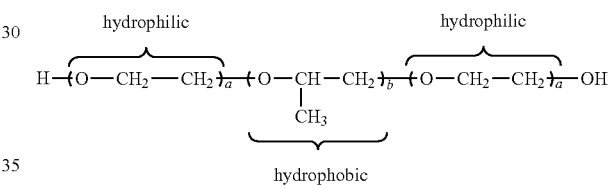

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly (DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The antimicrobial agent and various additives such as buffers, salts, and preservatives are subsequently added and dissolved. In some instances the antimicrobial agent and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of which is incorporated herein by reference for such disclosure).

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising an antimicrobial agent and a pharmaceutically acceptable buffer. In another embodiment, the pharmaceutically acceptable excipient or carrier is a gelling agent.

In other embodiments, useful antimicrobial agent auris-acceptable pharmaceutical formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris media or auris interna's natural buffering system, or does not interfere with the natural pH of the endolymph or perilymph: depending on where in the cochlea the antimicrobial agent formulation is targeted. In some embodiments, from about 10 μM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are aqueous thermoreversible gel formulations comprising an antimicrobial agent and a thermoreversible polymer, such as a poloxamer (e.g. Poloxamer 407). In some embodiments, the concentration of the thermoverisble polymer in the water being sufficient to provide a final viscosity (after intratympanic injection) from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP.

In some embodiments, the viscosity of the gel formulations presented herein is measured by any means described. For example, in some embodiments, an LVDV-II+CP Cone Plate Viscometer and a Cone Spindle CPE-40 are used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

If desired, the auris-acceptable pharmaceutical gels also contain osmolality adjustors and other excipients in addition, buffering agents, and pH adjusting agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at about 7.0 to about 8.0. In some embodiments, the buffering agent (e.g. tromethamine) is included at a concentration of about 0.4% to about 0.6% on a weight basis of the total composition.

General Methods of Sterilization

Provided herein are otic compositions that ameliorate or lessen pediatric otic disorders described herein. Further provided herein are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing".

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave. In some embodiments, the formulations described herein comprise micronized antimicrobial agents (e.g., micronized ciprofloxacin) that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}Co$ source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 μm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., ciprofloxacin) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In some instances, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma irradiation, filtration) lead to degradation of polymeric components (e.g., thermosetting, gelling or mucoadhesive polymer components) and/or the active agent in the formulation. In some instances, sterilization of an auris formulation by filtration through membranes (e.g., 0.2 µM membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The bioburden (e.g., microbial limit) and/or sterility (e.g., endotoxin level) is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP) <71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

Methods of Treatment

Administration—Otic Surgery

In some embodiments, administration of an antimicrobial composition or device described herein in combination with an otic intervention (e.g., an intratympanic injection, a stapedectomy, myringotomy, tympanostomy tube surgery, a medical device implant or a cell-based transplant) delays or prevents collateral damage to auris structures, e.g., irritation, inflammation and/or infection, caused by the external otic intervention (e.g., installation of an external device and/or cells in the ear). In some embodiments, administration of an antimicrobial composition or device described herein in combination with an implant allows for a more effective restoration of hearing loss compared to an implant alone.

In some embodiments, administration of an antimicrobial composition or device described herein reduces damage to cochlear structures caused by underlying conditions (e.g., bacterial meningitis, autoimmune ear disease (AIED)) allowing for successful cochlear device implantation. In some embodiments, administration of a composition or device described herein, in conjunction with otic surgery, medical device implantation and/or cell transplantation, reduces or prevents cell damage and/or inflammation associated with otic surgery, medical device implantation and/or cell transplantation.

In some embodiments, administration of an antimicrobial composition or device described herein (e.g., a composition or device comprising ciprofloxacin) in conjunction with a cochlear implant or stem cell transplant has a trophic effect (e.g., promotes healthy growth of cells and/or healing of tissue in the area of an implant or transplant). In some embodiments, a trophic effect is desirable during otic surgery or during intratympanic injection procedures. In some embodiments, a trophic effect is desirable after installation of a medical device or after a cell transplant. In some of such embodiments, the antimicrobial compositions or devices described herein are administered via direct cochlear injection, through a chochleostomy or via deposition on the round window. In some embodiments, a medical device is coated with a composition described herein prior to implantation in the ear.

In one aspect, the formulations described herein, and modes of administration thereof, are applicable to methods of direct injection into the middle ear. Thus, the formulations described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, myringotomy, tympanostomy tube surgery, endolymphatic sacculotomy or the like. In some embodiments, the inner ear compartments are perfused with a formulation described herein prior to otic intervention, during otic intervention, or after otic intervention, or a combination thereof.

In some embodiments, the auris gel formulations are capable of being administered into the middle ear via intratympanic injection. In other embodiments, the auris gel formulations are administered into the middle ear via a post-auricular incision. Alternatively, the auris gel formulation is applied via syringe and needle, wherein the needle is inserted through the tympanic membrane and into the middle ear. The auris gel formulations are then deposited into the middle ear for localized treatment of otic disorders. In other embodiments, the auris gel formulations are applied via microcathethers implanted into the patient, and in yet further embodiments the formulations are administered via a pump device through the surgical incision on the tympanic membrane. In still further embodiments, the auris gel formulations are administered into the middle ear via a microinjection device. In yet other embodiments, the auris gel formulations are administered into the tympanic cavity. In some embodiments, the auris gel formulations are applied on the tympanic membrane. In still other embodiments, the auris gel formulations are applied onto or in the auditory canal.

In certain embodiments, a composition described herein is administered before a pediatric otic intervention (e.g., before implantation of a medical device or a cell-based therapeutic). In certain embodiments, a composition described herein is administered during a pediatric otic intervention (e.g., during implantation of a medical device or a cell-based therapeutic). In other embodiments, a composition described herein is administered after a pediatric otic intervention (e.g., after implantation of a medical device or a cell-based therapeutic). In some of such embodiments, a composition described herein that is administered after the pediatric otic intervention is an intermediate release or extended release composition (e.g., a composition comprising an antibiotic and optionally comprising an anti-inflammatory agent) and contains gelling components as described herein. In some embodiments, an implant (e.g., a tympanostomy tube) is coated with a composition or device described herein prior to insertion in the ear.

In some embodiments, a composition described herein comprising micronized ciprofloxacin is administered to a pediatric patient via an intratympanic injection anterior to the round window membrane. In some embodiments, a composition described herein comprising micronized ciprofloxacin is administered to a pediatric patient at the site of myringotomy. In some embodiments, a composition described herein comprising micronized ciprofloxacin is administered to a pediatric patient before myringotomy. In other embodiments, a composition described herein comprising micronized ciprofloxacin is administered to a pediatric patient after myringotomy. In some embodiments, a composition described herein comprising micronized ciprofloxacin is administered to a pediatric patient before tympanostomy tube placement. In other embodiments, a composition described herein comprising micronized ciprofloxacin is administered to a pediatric patient after tympanostomy tube placement. In some embodiments, a composition described herein comprising micronized ciprofloxacin is administered to a pediatric patient after myringotomy and before tympanostomy tube placement. In some embodiments, a composition described herein comprising micronized ciprofloxacin is administered to a pediatric patient before myringotomy and before tympanostomy tube placement. In some embodiments, a composition described herein comprising micronized ciprofloxacin is administered to a pediatric patient after myringotomy and after tympanostomy tube placement.

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the antimicrobial agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the antimicrobial agent compositions or formulations, the gauge level of the syringe or hypodermic needle may be varied accordingly. In another embodiment, the internal diameter of the needle can be increased by reducing the wall thickness of the needle (commonly referred as thin wall or extra thin wall needles) to reduce the possibility of needle clogging while maintaining an adequate needle gauge.

In another embodiment, the needle is a hypodermic needle used for instant delivery of the gel formulation. The hypodermic needle may be a single use needle or a disposable needle. In some embodiments, a syringe may be used for delivery of the pharmaceutically acceptable gel-based antimicrobial agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the antimicrobial agent pharmaceutically acceptable gel-based compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the antimicrobial agent or other pharmaceutical compounds contained therein.

In some embodiments, the syringe comprises a cylindrical syringe body wherein the body is compartmentalized in that each compartment is able to store at least one component of the auris-acceptable antimicrobial agent gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises an antimicrobial agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

In some embodiments, the auris-acceptable composition described herein is administered through a single intratypanic injection, wherein the composition contains from about 2 mg to about 14 mg, from about 2 mg to about 12 mg, from about 4 mg to about 12 mg, from about 4 mg to about 10 mg, from about 4 mg to about 8 mg, from about 5 mg to about 8 mg, from about 5 mg to about 7 mg, or from about 5.5 mg to about 6.5 mg, of the antimicrobial agent, sucha as ciprofloxacin. In some embodiments, those dosages are in the form of a composition comprising 15-17% by weight of poloxamer 407 and 5.4-6.6% by weight of micronized ciprofloxacin. In some embodiments, those dosages are in the form of a composition comprising 15-17% by weight of poloxamer 407 and 1.8-2.2% by weight of micronized ciprofloxacin. In some embodiment, 200 μL of a composition containing 4 mg of ciprofloxacin is administered to an ear through intratympanic injection. In some embodiment, 200 μL of a composition containing 12 mg of ciprofloxacin is administered to an ear through intratympanic injection. In some embodiment, 100 μL of a composition containing 6 mg of ciprofloxacin is administered to an ear through intratympanic injection The auris-acceptable compositions or formulations containing the antimicrobial agent compound(s) described herein are administered for prophylactic and/or therapeutic treatments. In therapeutic applications, the antimicrobial agent compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

Frequency of Administration

In some embodiments, a composition disclosed herein is administered to an individual in need thereof once. In some embodiments, a composition disclosed herein is administered to a pediatric patient in a single injection to the patient's infected ear. In some embodiments, a composition disclosed herein is administered to an individual in need thereof more than once.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an antimicrobial may be administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the antimicrobial agent compounds may be administered chronically, that is, for an extended period of time, including throughout the duration of the patient's life in order to ameliorate or otherwise control or limit the symptoms of the patient's disease or condition.

The amount of antimicrobial agent that will correspond to such an amount will vary depending upon factors such as the particular compound, disease condition and its severity, according to the particular circumstances surrounding the case, including, e.g., the specific antimicrobial agent being administered, the route of administration, the autoimmune condition being treated, the target area being treated, and the subject or host being treated.

Pharmacokinetics of Controlled Release Formulations

In some embodiments, the formulation provides an extended/sustained release formulation of at least one antimicrobial agent. In certain embodiments, diffusion of at least one antimicrobial agent from the formulation occurs for a time period exceeding 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one antimicrobial agent is released from the formulation for a time period exceeding 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In a specific embodiment the formulation provides a therapeutically effective amount of at least one antimicrobial agent at the site of disease with essentially no systemic exposure. In an additional embodiment the formulation provides a therapeutically effective amount of at least one antimicrobial agent at the site of disease with essentially no detectable systemic exposure. In other embodiments, the formulation provides a therapeutically effective amount of at least one antimicrobial agent at the site of disease with little or no detectable detectable systemic exposure.

The combination of immediate release, delayed release and/or extended release antimicrobial agent compositions or formulations may be combined with other pharmaceutical agents, as well as the excipients, diluents, stabilizers, tonicity agents and other components disclosed herein. As such, depending upon the antimicrobial agent used, the thickness or viscosity desired, or the mode of delivery chosen, alternative aspects of the embodiments disclosed herein are combined with the immediate release, delayed release and/or extended release embodiments accordingly.

Kits/Articles of Manufacture

The disclosure also provides kits for preventing, treating or ameliorating the symptoms of a disease or disorder in a mammal. Such kits generally will comprise one or more of the antimicrobial agent controlled-release compositions or devices disclosed herein, and instructions for using the kit. The disclosure also contemplates the use of one or more of the antimicrobial agent controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of antimicrobial agent formulations compositions provided herein are contemplated as are a variety of treatments for any disease, disorder, or condition that would benefit by controlled release administration of an antimicrobial agent to the inner ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1

Preparation of a Thermoreversible Gel Ciprofloxacin Composition Comprising Micronized Ciprofloxacin Powder (Composition A)

| Ingredient | Quantity (mg/mL of formulation) |
| --- | --- |
| ciprofloxacin | 60.0 |
| Poloxamer 407 | 157 |
| Sodium Chloride | 4.5 |
| Tromethamine | 5.8 |
| Hydrochloric acid (37.5% w/w) | QS for pH adjustment (pH 7.0-8.0) |
| Water for injection | QS to 1040 |

Ciprofloxacin was purchased from Neuland Laboratories. CIPRODEX® Otic (0.3% ciprofloxacin and 0.1% dexamethasone suspension) and CETRAXAL® Otic (0.2% ciprofloxacin solution) were obtained from MWI Veterinary. Acepromazine, ketamine and xylazine were also from MWI Veterinary. Poloxamer 407 was purchased from BASF. Ciprofloxacin was heat sterilized and combined with a heat or filtration sterilized diluent comprising the Poloxamer 407 and other ingredients to form the finalized formulation. Other Composition As (with different ciprofloxacin concentrations) were prepared similarly.

Example 2

In Vivo Testing of Intratympanic Injection of Composition a in Guinea Pigs

Male and female guinea pigs (Hartley HA:Crl, Charles River Laboratories, n=4-5 per sex, per group) weighing 200-300 g, of approximately 6-8 weeks of age were used for the pharmacokinetic and toxicology experiments. Prior to any procedure, animals were anesthetized either using a combination of xylazine (10 mg/kg), ketamine (40 mg/kg), and acepromazine (0.75 mg/kg) for up to an hour via the intramuscular route, or using isoflurane to effect via inhalation. During the procedure and until recovery, animals were placed on a temperature controlled (40° C.) heating pad. After consciousness was regained, animals were returned to the vivarium.

Intratympanic injection of Composition A anterior to the round window membrane (IT-ANT)—All animals were injected bilaterally. Each animal was positioned so that the head was tilted at an angle to favor injection away from the round window niche to the middle ear cavity. Briefly, under visualization with an operating microscope, 50 μl of Composition A was injected using a 22 G needle through the tympanic membrane into the inferior anterior quadrant.

Tympanostomy tube placement—While the animal was anesthetized, a 27 G needle was used to create a pinhole (myringotomy) in the lower anterior portion of the tympanic membrane. A ventilation tube (FEP, internal diameter 0.56 mm, wall thickness 0.15 mm, length 2.5-3.0 mm) was inlayed through the hole.

CIPRODEX® and CETRAXAL® treatment course—Awake guinea pigs were manually restrained for a short period of time while the otic drops (10 μl auris utraque (AU) for CIPRODEX®, 15 μl AU for CETRAXAL®) were administered into the external ear canal in proximity to the tympanostomy tube. Tragal pumping was then performed several times to ensure penetration of the drug into the middle ear cavity. Drugs were administered twice daily (9 AM and 5 PM) for 7 consecutive days.

Free ciprofloxacin (middle ear lavage) and tissue-bound ciprofloxacin (epithelium) collections—For the middle ear lavage, the lower anterior and posterior portion of the tympanic membrane was removed, with an attempt to prevent disturbing the upper anterior and upper posterior portions of the tympanum. Using a 27 gauge blunt needle, the middle ear cavity was lavaged twice in the following manner: 100 μl of sterile water was placed into the middle ear and then extracted using the same syringe. Both washes (totaling about 200 μl) were collected into a single tube for subsequent analysis. The lavage volume was chosen as it represents the average volume capacity of the guinea pig middle ear. Free drug concentration data were normalized to a hypothetical middle ear volume of 250 μl. For the middle ear epithelium collection, the bulla from each guinea pig was removed and extensively flushed with sterile water. The bulla was then slightly surgically exposed, the middle epithelium layer dissected from the bulla and weighed and stored for analysis. Tissue-bound drug concentration data were expressed as µg ciprofloxacin per gram of tissue weight.

Ossicle mobility assessment—At necropsy, using a dissecting microscope, the middle ear was opened, and the ossicles revealed by removing regions of the temporal bone. A forceps was used to gently apply pressure to the ossicles to determine mobility.

Example 2A

Middle Ear Free Ciprofloxacin Levels

Female guinea pigs received a single IT-ANT injection of various doses of Composition A: 0.06% (closed inverted triangles), 0.2% (stars), 0.6% (closed circles), 2% (closed triangles), 6% (closed squares) and 12% Composition A (closed diamonds). A twice-daily one-week course of CIPRODEX® (B) or CETRAXAL® (C) administered through a tympanostomy tube was given. Free drug levels of ciprofloxacin, obtained by lavaging the middle ear, were determined at the indicated times. (B and C) Predicted profile of ciprofloxacin by combining peak and trough levels.

Determination of free ciprofloxacin concentrations was performed using high pressure liquid chromatography (HPLC). The limit of detection of the method was 100 ng/ml. Middle ear lavage samples were centrifuged 10 min at 15000 rpm and the supernatant collected. Extraction of ciprofloxacin was performed by a 1:1 dilution using acetonitrile:TEA phosphate buffer (40:60 v/v, pH 3.0) followed by centrifugation. Middle ear epithelium samples were extracted using acetonitrile:TEA phosphate buffer (20:80 v/v, pH 3.0) and submitted to sonication and vortexing. The samples were analyzed by reverse phase HPLC (1200 series, Agilent) equipped with UV detection (278 nm) using a phenyl-hexyl Luna column (3 µm; 250×4.6 mm). A flow rate of 0.7 ml/min was applied with the following gradient method: isocratic (20:80 acetonitrile:TEA-phosphate buffer) the first 8 minutes followed by a gradient from 8-10 min up to a ratio of 50:50 acetonitrile:TEA-phosphate buffer, isocratic up to 24 min then a gradient from min 24-26 to the original conditions. Quantification was performed against an external standard. Sample ciprofloxacin concentrations were interpolated based upon from the calibration curves.

Figure 4:
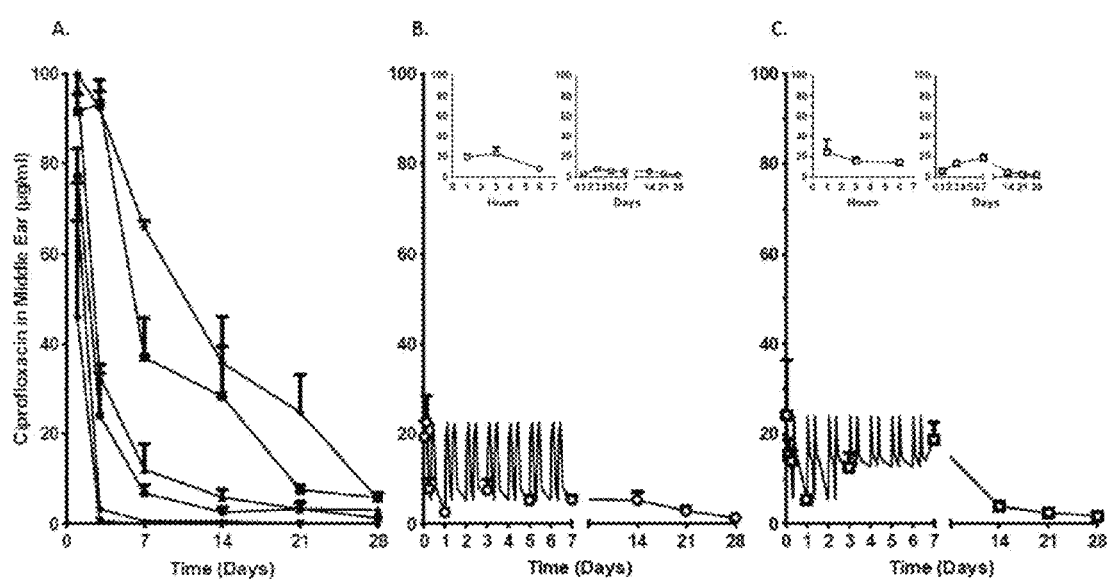
FIG. 4: Middle ear free ciprofloxacin levels following administration of Composition A, CIPRODEX® or CETRAXAL®. (A) Female guinea pigs received a single IT-ANT injection of various doses of Composition A: 0.06% (closed inverted triangles), 0.2% (stars), 0.6% (closed circles), 2% (closed triangles), 6% (closed squares) and 12% Composition A (closed diamonds). A twice-daily one-week course of CIPRODEX® (B) or CETRAXAL® (C) administered through a tympanostomy tube was given. Free drug levels of ciprofloxacin, obtained by lavaging the middle ear, were determined at the indicated times. (B and C) Predicted profile of ciprofloxacin by combining peak and trough levels. Left inset: peak levels; right inset: trough levels. Data are presented as mean±SEM (n=4 ears per group per time point).

Administration of Composition A: The levels of free ciprofloxacin in the middle ear were determined following a single IT-ANT injection of various doses of Composition A, ranging from 0.06% to 12% (FIG. 4A). Depending on the dose given, ciprofloxacin levels peaked at Day 1 between 45.4±22.1 and 99.9±5.6 µg/ml. Disappearance from the middle ear compartment was strongly dependent upon the Composition A dose, with drug levels dropping below 2 µg/ml in as little as 3 days with 0.06% Composition A, approximately 7 days with 0.2% Composition A, but remaining on or above these levels for 28 days with higher Composition A doses. Overall, a single intratympanic injection of Composition A provided high $C_{max}$ and steady dose, with progressive decline over time.

Administration of CIPRODEX®: Following a single application of CIPRODEX® drops, ciprofloxacin peak levels reached 22.6±5.9 µg/ml within 3 hours, then declined sharply to 7.8±2.2 µg/ml by 6 hours (FIG. 4B). During the twice daily for 7 days regimen, the trough levels were determined 16 hours post the second daily administration from the preceding day. Ciprofloxacin levels varied from 2.6±0.4 µg/ml at Day 1, immediately before the $3^{rd}$ dose, to 8.6±0.4 µg/ml at treatment completion. By compiling the data from peak and trough levels, the predicted middle ear free ciprofloxacin profile following CIPRODEX® treatment was derived. The pulsatile nature of CIPRODEX® administration was quite evident, with free ciprofloxacin levels in the middle ear cycling rapidly between each otic drop application. The amplitude between the lowest and highest drug levels within each cycle varied by almost 10-fold, from 2.6±0.4 to 22.6±5.9 µg/ml. There was a noted drug accumulation during the treatment course reaching 8.6±0.4 µg/ml at Day 7. Following the completion of the twice daily for 7 days dosing regimen, ciprofloxacin levels slowly decreased, reaching 1.3±0.9 µg/ml by Day 28.

Administration of CETRAXAL®: (FIG. 4C). Ciprofloxacin free middle ear levels reached 24.1±12.2 µg/ml at 1 hour, decreasing to 14.0±2.4 µg/ml by 6 hours. Drug accumulation during the twice daily for 7 days treatment was pronounced, increasing from 5.3±0.8 µg/ml at Day 1 to 18.6±4.1 µg/ml at Day 7. Thereafter, elimination was slow with levels declining to 1.8±0.8 µg/ml by Day 28.

A compilation of the middle ear ciprofloxacin pharmacokinetic parameters is presented in FIG. 3. The administration of Composition A yielded significantly higher $C_{max}$ values, ranging from 45.4 to 99.9 µg/ml, than either CIPRODEX® or CETRAXAL®, 22.6 µg/ml and 24.1 µg/ml, respectively. Consequently, the degree of exposure (as measured by AUC) following Composition A administration was comparable to that of CIPRODEX® and CETRAXAL® at low Composition A doses (0.06 to 0.6%), but significantly larger at higher Composition A doses, being 6- to 10-fold higher at 12% Composition A. Measures of predicted antimicrobial clinical efficacy were determined and based upon a MIC of 2 µg/ml, which defines the breakpoint for bacteria of intermediate susceptibility to ciprofloxacin. Three parameters were considered: time of ciprofloxacin above MIC (T>MIC), $C_{max}$/MIC and $AUC_{0-24}$/MIC ratios. For both CIPRODEX® and CETRAXAL®, T>MIC is of 25 days, specifically 601 and 611 hours, respectively. The different Composition A doses bracket these values, with a T>MIC of 2.6 days (63 h) at 0.06% Composition A to 30.0 days (721 h) at 12% Composition A. Both CIPRODEX® and CETRAXAL® exhibit good predicted clinical efficacy values, typically 1-2 fold above the proposed limits. Composition A values are excellent with $C_{max}$/MIC ratios 2-5 fold and $AUC_{0-24}$/MIC 5-12 fold above the recommended values, respectively.

Example 2B

Middle Ear Epithelium (Tissue-Bound) Ciprofloxacin

Figure 5:
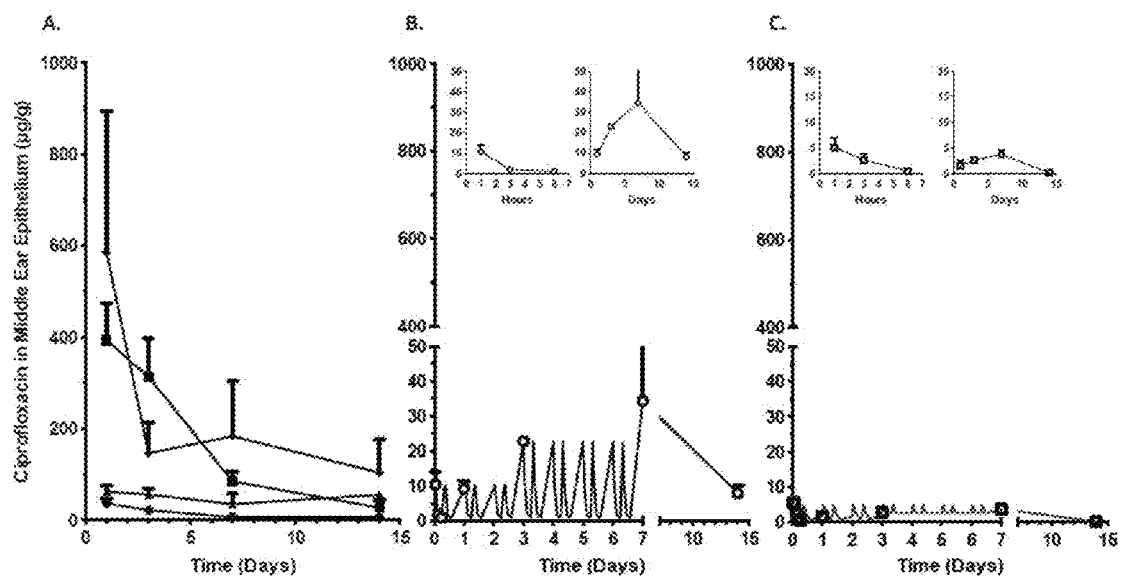
FIG. 5: Middle ear epithelium (tissue-bound) ciprofloxacin levels following administration of Composition A, CIPRODEX® or CETRAXAL®. (A) Female guinea pigs received a single IT-ANT injection of various doses of Composition A: 0.6% (closed circles), 2% (closed triangles), 6% (closed squares) or 12% (closed diamonds). A twice-daily one-week course of CIPRODEX® (B) or CETRAXAL® (C) administered through a tympanostomy tube was given. Tissue-bound levels of ciprofloxacin, obtained by harvesting the middle ear epithelium, were determined at the indicated times. (B and C) Predicted profile of ciprofloxacin by combining peak and trough levels. Left inset: peak levels; right inset: trough levels. Data are presented as mean±SEM (n=4 ears per group per time point).

Administration of Composition A: Female guinea pigs received a single IT-ANT injection of various doses of Composition A: 0.6% (closed circles), 2% (closed triangles), 6% (closed squares) or 12% (closed diamonds). A single IT-ANT injection of Composition A (0.6% to 12%) resulted in tissue-bound drug levels reaching 37.0±10.2 to 586±309 µg/ml at Day 1, depending on the dose (FIG. 5A). These values were 1-6 fold higher than the free ciprofloxacin concentrations noted in the middle ear. Ciprofloxacin elimination from the middle ear epithelium was limited, with concentrations remaining between 7.0±2.1 µg/ml and 103.8±72.4 µg/ml at Day 14, at the 0.6% and 12% Composition A doses, respectively.

Administration of CIPRODEX® or CETRAXAL®: A twice-daily one-week course of CIPRODEX® or CETRAXAL® was administered to female guinea pigs through a tympanostomy tube. Tissue-bound levels of ciprofloxacin, obtained by harvesting the middle ear epithelium, were determined at the indicated times. (FIGS. 5B and 5C) Following administration of CIPRODEX®, tissue-bound ciprofloxacin peaked at 10.5±3.5 µg/ml within 1 hour decreasing to 1.0±0.3 µg/ml within 6 hours (FIG. 5B). Drug accumulation was marked during the treatment course reaching 34.4±16.3 µg/ml at Day 7. Over the next 7 days, ciprofloxacin levels decreased sharply to 8.0±2.2 µg/ml by Day 14. Following administration of CETRAXAL® (FIG. 5C), middle ear epithelium ciprofloxacin levels reached a maximum of 5.1±1.8 µg/ml at 1 hour decreasing to 0.5±0.3 µg/ml by 6 hours. Over the twice daily for 7 days treatment course, tissue-bound ciprofloxacin accumulated to 3.7±0.7 µg/ml at Day 7 from 1.5±1.1 µg/ml at Day 1, but decreased rapidly to 0.1±0.1 µg/ml by Day 14.

Example 2C

Inner Ear Ciprofloxacin Levels

Perilymph collection—The skin behind the ear of anesthetized guinea pigs was shaved and disinfected with povidone-iodine. An incision was then made behind the ear, and muscles were carefully retracted from over the bulla. A hole was drilled though the bulla using a dental burr so that the middle ear was exposed and accessible. The cochlea and the round window membrane were visualized under a stereo surgical microscope. Mucosal tissues of the cochlea were removed and the area washed carefully to remove any potential drug contaminants. A unique microhole was hand drilled through the bony shell of the cochlea (otic capsule) adjacent to the round window. Perilymph (5 µl) was then collected using a microcapillary inserted into the cochlear scala tympani.

Perilymphatic ciprofloxacin—Determination of ciprofloxacin concentrations was performed using HPLC combined with mass spectrometry detection (MS/MS). The limit of detection of the method was 1 ng/ml. Samples were extracted by protein precipitation using acetonitrile and the organic supernatant was diluted in aqueous solution (1:2 v/v) prior to analysis. The samples were analyzed by reversed phase HPLC (1200 series, Agilent) using an ACE C18 column (3 µm; 50×2.1 mm) at room temperature. The compound was ionized by electrospray and detected using MS/MS in positive mode (Tandem quadrupole mass spectrometer, API4000, Applied Biosystems). Peak areas of ciprofloxacin were determined using Analyst 1.5 software (Applied Biosystems). The calibration curves were obtained by fitting the peak area ratios of analyte/internal standard and the nominal standard concentrations to a suitable equation using Analyst. Sample ciprofloxacin concentrations were then interpolated using the equations derived from the calibration curves.

Figure 6:
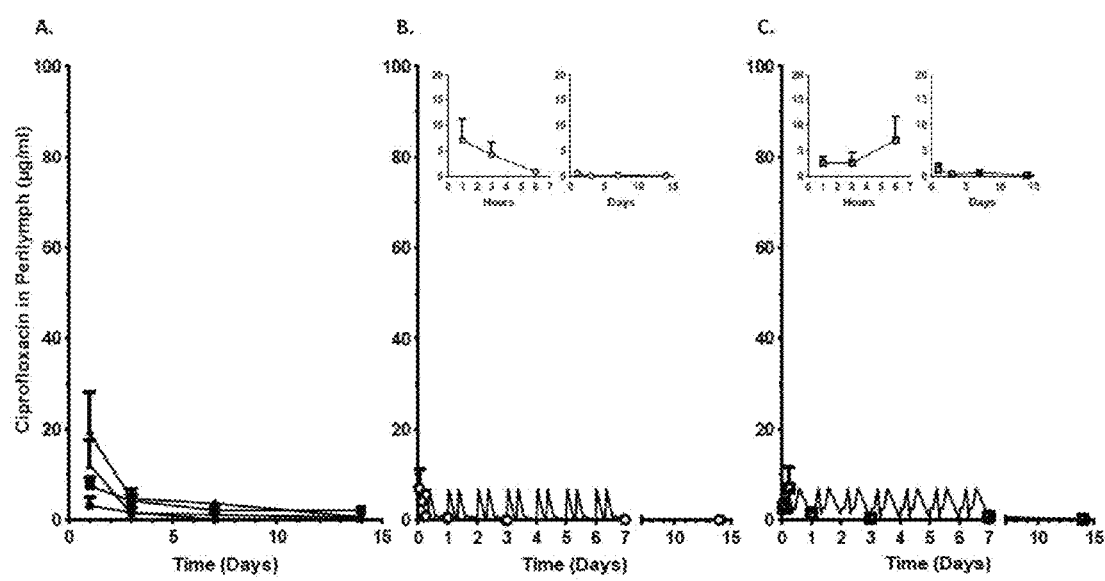
FIG. 6: Inner ear ciprofloxacin levels following administration of Composition A, CIPRODEX® or CETRAXAL®. (A) Guinea pigs received a single IT-ANT injection of various doses of Composition A: 0.6% (closed circles), 2% (closed triangles), 6% (closed squares) or 12% (closed diamonds). A twice-daily one-week course of CIPRODEX® (B) or CETRAXAL® (C) administered through a tympanostomy tube was given. Perilymph levels of ciprofloxacin were determined at the indicated times. (B and C) Predicted profile of ciprofloxacin by combining peak and trough levels. Left inset: peak levels; right inset: trough levels. Data are presented as mean±SEM (n=4 ears per group per time point).

Administration of Composition A: Guinea pigs received a single IT-ANT injection of various doses of Composition A: 0.6% (closed circles), 2% (closed triangles), 6% (closed squares) or 12% (closed diamonds). One day post administration of Composition A (FIG. 6A), perilymph concentrations of ciprofloxacin ranged from 3.1±1.8 µg/ml at 0.6% Composition A to a maximum of 19.0±9.2 µg/ml at 12% Composition A. These values were 5 to 25-fold lower than the levels observed in the middle ear, depending on the dose. Elimination from this compartment was relatively rapid, with ciprofloxacin concentrations dropping below 2 µg/ml within 1-2 weeks.

Administration of CIPRODEX® or CETRAXAL®: A twice-daily one-week course of CIPRODEX® (B) or CETRAXAL® (C) administered through a tympanostomy tube was given. Perilymph levels of ciprofloxacin were determined at the indicated times. (FIGS. 6B and 6C) Following administration of CIPRODEX® (FIG. 6B), levels of ciprofloxacin in the perilymph cycled rapidly and extensively between each dose from 7.0±4.2 µg/ml to 0.9±0.3 µg/ml. No drug accumulation was evident in the inner ear compartment during the treatment course. By Day 14, ciprofloxacin levels were below 0.1±0.1 µg/ml. When CETRAXAL® was given (FIG. 6C), perilymph ciprofloxacin concentrations fluctuated from 0.3±0.1 µg/ml to 7.1±4.6 µg/ml. At Day 7, upon completion of treatment, drug levels were of 0.7±0.3 µg/ml, declining to 0.2±0.2 µg/ml by Day 14.

Example 3

Intratympanic Injection of Composition A in Chinchillas Otitis Media Model

Otitis media was induced in chinchillas by middle ear inoculation of *S. pneumoniae*. Three days later, when otitis media was well established, the middle ear effusion was drained, a tympanostomy tube placed and the therapeutic agent applied.

Male chinchillas (chinchilla laniger, Moulton Chinchilla Ranch, n=6-13 per group) weighing 400-700 g, 4 months to 4 years of age were used for the otitis media experiments. Prior to any procedure, animals were anesthetized for a period of up to an hour using a cocktail of xylazine (2 mg/kg), ketamine (40 mg/kg), and acepromazine (0.5 mg/kg) administered intramuscularly. During the procedure and until recovery, animals were placed on a temperature controlled (40° C.) heating pad. After consciousness was regained, animals were returned to the vivarium.

Bacterial inoculum—The inoculum was always generated from a freshly grown isolated colony from the original bacterial stock (*Streptococcus pneumoniae* serotype 6C variant 10AR004), to minimize genetic drift. The clinical isolate strain was obtained from a patient with documented otitis media, and generously provided by Dr. Stephen Pelton. A starter culture of 10 ml Brain Heart Infusion (BHI) media was inoculated with one isolated colony and grown for 10 h at 31° C. to prevent autolyzing activity. One ml of the starter culture was used to seed a 100 ml BHI flask and grown at 37° C. until mid-log phase. The mid-log phase was previously determined to be optimal at an optical density of 0.3 arbitrary units when determined at 600 nm. Typically the mid-log phase was reached within 3-4 h. The bacterial culture was centrifuged (5000 rpm, 15 min) and the pellet resuspended in 10 ml BHI. Subsequently, serial dilutions were made to obtain inoculum at 2000 CFU/ml. Calculations were based on previously established growth titration curves. The inoculum was used immediately to inoculate chinchilla ears. Aliquots of serial dilutions were immediately plated onto chocolate agar plates (1.0% bovine hemoglobin) in duplicates, and incubated overnight at 37° C. in 5% $CO_2$ to confirm the titer of the inoculum.

Induction of otitis media—Anesthetized chinchillas received a bilateral middle ear injection of the bacterial inoculate (100 µl of a solution containing 200 CFUs of exponentially-growing *S. pneumoniae*). The inoculum was injected directly into the middle ear via the intratympanic route using a 27 G or 30 G needle. Otitis media was evident in the large majority of animals by Day 3 post inoculation, as documented by the high bacterial titer and presence of effusion in the middle ear.

Intratympanic injection of Composition A anterior to the round window membrane (IT-ANT)—All animals were treated bilaterally. Each animal was positioned so that the head was tilted at an angle to favor visualization of the tympanic membrane. A 27 G or 30 G needle was used to drain the middle ear effusion by aspiration through the tympanic membrane. The procedure was conducted under visualization with an operating microscope. Immediately after, 50 µl of Composition A was injected intratympanically using a 22 G needle through the tympanic membrane into the posterior superior quadrant, through the same pinhole used for drainage. Then, a ventilation tube (FEP, internal diameter 0.81 mm, wall thickness 0.15 mm, length 3.5-4.0 mm) was placed opposite of the site of intratympanic injection to limit the risk of the hydrogel formulation interfering with tube patency.

CIPRODEX® and CETRAXAL® treatment course—All animals were treated bilaterally. Each animal was positioned so that the head was tilted at an angle to favor visualization of the tympanic membrane. At time of treatment initiation, the middle ear was drained of any effusion and immediately thereafter a tympanostomy tube was placed as described above. The otic drops (10 µl AU for CIPRODEX®, 15 µl AU for CETRAXAL®) were administered into the external ear canal in proximity to the tympanostomy tube and the tragus pumped several times to ensure penetration of the drug into the middle ear cavity. Drugs were administered twice daily (9 AM and 5 PM) for 3 consecutive days. The initial dosing occurred while the chinchillas were anesthetized. For the subsequent applications, chinchillas were manually restrained for a short period of time.

Determination of middle ear effusion volumes, bacterial titer and ciprofloxacin levels—Middle ear effusion volumes were collected at Day 6 (3 days post treatment initiation and 6 days post bacterial inoculation), quantified and split in two. For the determination of the bacterial titer, the middle ear effusion volumes were adjusted to an arbitrary volume of 1 ml from which serial dilutions of 10-fold increments were conducted up to the $10^8$ dilution. Aliquots of 100 µl of each serial dilution were plated onto chocolate agar plates (1.0% bovine hemoglobin) in duplicates, and incubated overnight at 37° C. in 5% $CO_2$. Bacterial titer was determined by counting the number of colonies present, corrected for the different dilution factors and presented as CFU/ml. Only *S. pneumoniae* colonies were counted, reflecting the initial otitis media with effusion infection. For the determination of ciprofloxacin concentrations, the middle ear effusion aliquots were submitted to HPLC analysis.

Example 3A

Middle Ear Bacterial Load and Effusion Volume in Chinchillas with Otitis Media

Figure 7:
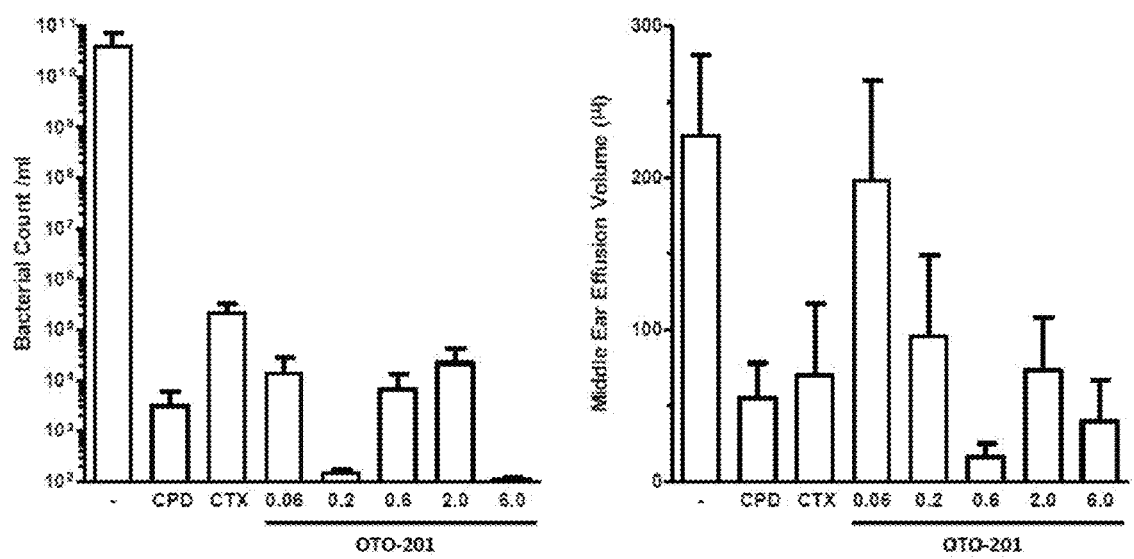
FIG. 7: Middle ear bacterial load and effusion volume in chinchillas with otitis media treated with Composition A, CIPRODEX® or CETRAXAL®. Otitis media was induced by middle ear inoculation of *S. pneumoniae*. Immediately prior to drug administration (at Day 3 post inoculation), the middle ear was drained of effusion and a tympanostomy tube placed. Chinchillas received either a single IT-ANT injection of various doses of Composition A, or a twice daily for 3 days treatment course of CIPRODEX® (CPD) or CETRAXAL® (CTX). The bacterial titer and effusion volume in the middle ear were determined. Data are presented as mean±SEM (n=6-13 ears).

Administration of Composition A: Chinchillas received a single IT-ANT injection of various doses of Composition A as a single IT-ANT injection immediately prior to tympanostomy tube placement. A summary of the treatment regimens is presented in FIG. 2. The bacterial titer and effusion volume in the middle ear were determined (FIG. 7).

Various doses of Composition A were evaluated, ranging from 0.06% to 6%. All doses were effective in reducing the middle ear bacterial load by 6-8 log orders of magnitude, depending on the dose. Values ranged from $1.1 \times 10^2$ CFU/ml to $2.2 \times 10^4$ CFU/ml. All doses, with the exception of 0.06% Composition A, were also effective in reducing the middle ear effusion to the levels seen with either CIPRODEX® and CETRAXAL®. The middle ear effusion volume in the 0.06% Composition A treatment group was 198±66 µl, not significantly different than the control group. For the other doses that were effective, the volumes ranged from 16±9 µl to 73±35 µl.

Administration of CIPRODEX® and CETRAXAL®: CIPRODEX® and CETRAXAL® were administered twice daily for 3 days to chinchillas following tympanostomy tube placement. A summary of the treatment regimens is presented in FIG. 2. The bacterial titer and effusion volume in the middle ear were determined. CIPRODEX® reduced the bacterial load in the middle ear by more than 6 log orders of magnitude relative to untreated subjects, to $3.2 \times 10^3$ CFU/ml from $4.0 \times 10^{10}$ CFU/ml, respectively (FIG. 7). A significant decrease in the extent of the middle ear effusion was also noted, with volumes of 55±23 µl relative to the control 228±53 µl. Following treatment with CETRAXAL®, the bacterial titer was decreased by about 5 logs to $2.1 \times 10^5$ CFU/ml and the middle ear effusion volume to 70±47 µl.

Example 3B

Time to Clinical Cure in Chinchillas with Otitis Media

Figure 8:
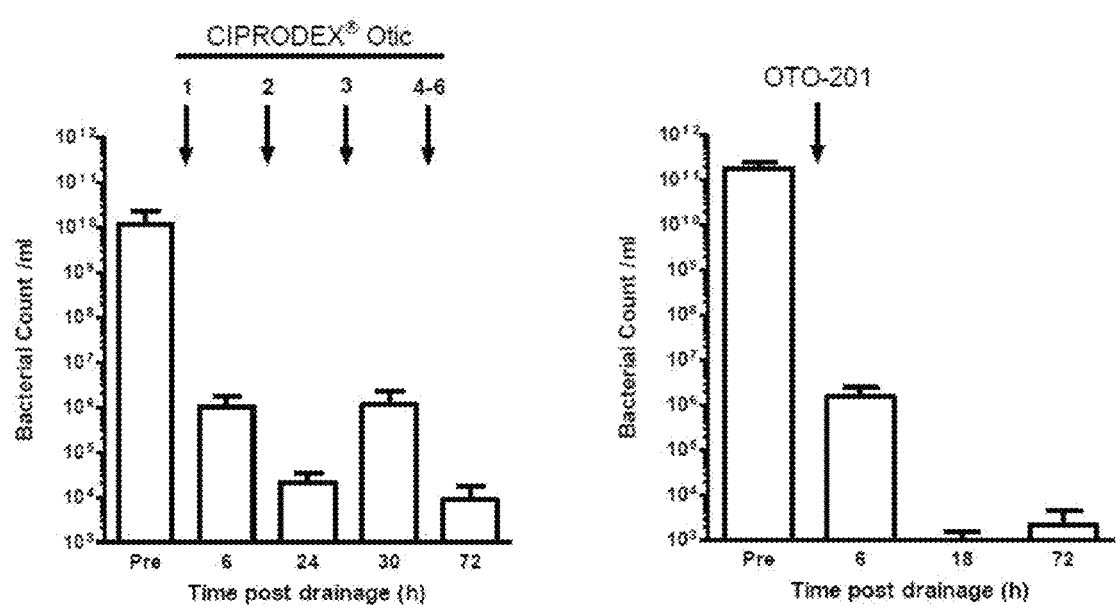
FIG. 8: Time to clinical cure in chinchillas with otitis media treated with Composition A or CIPRODEX®. Otitis media was induced by middle ear inoculation of *S. pneumoniae*. Immediately prior to drug administration (at Day 3 post inoculation), the middle ear was drained of effusion and a tympanostomy tube placed. Chinchillas received either a single IT-ANT injection of various doses of Composition A, or a twice daily for 3 days treatment course of CIPRODEX®. The bacterial titer was determined at the indicated times. Data are presented as mean±SEM (n=6-10 ears). Arrows refer to the time of administration of Composition A or CIPRODEX®.

Administration of Composition A: Chinchillas received a single IT-ANT injection of various doses of Composition A as a single IT-ANT injection immediately prior to tympanostomy tube placement. The bacterial titer was determined at the indicated times (FIG. 8). The single IT-ANT administration of Composition A yielded rapid clinical cure, with a bacterial titer dropping to $9.2 \times 10^5$ CFU/ml at 6 h from $1.8 \times 10^{11}$ CFU/ml. Clinical cure was present within 18 h of Composition A treatment, as evidenced by a bacterial load of $2.2 \times 10^3$ CFU/ml.

Administration of CIPRODEX®: Chinchillas received a twice daily for 3 days treatment course of CIPRODEX® following tympanostomy tube placement. The bacterial titer was determined at the indicated times (FIG. 8). Following the first application of CIPRODEX®, the bacterial titer dropped by about 4 logs within the first 6 h of treatment, from $1.2 \times 10^{10}$ CFU/ml to $1.0 \times 10^6$ CFU/ml. However, evidence of intermittent bacterial growth was evident in between CIPRODEX® applications: at 24 h, the bacterial load was of $2.2 \times 10^4$ CFU/ml while at 30 h it had increased to $1.2 \times 10^6$ CFU/ml. By 72 h, clinical cure was evident with a bacterial titer of $8.7 \times 10^3$ CFU/ml, i.e. a 6-Log reduction compared to pre-treatment levels.

Example 3C

Middle Ear Ciprofloxacin Levels in Chinchillas with Otitis Media

Figure 9:
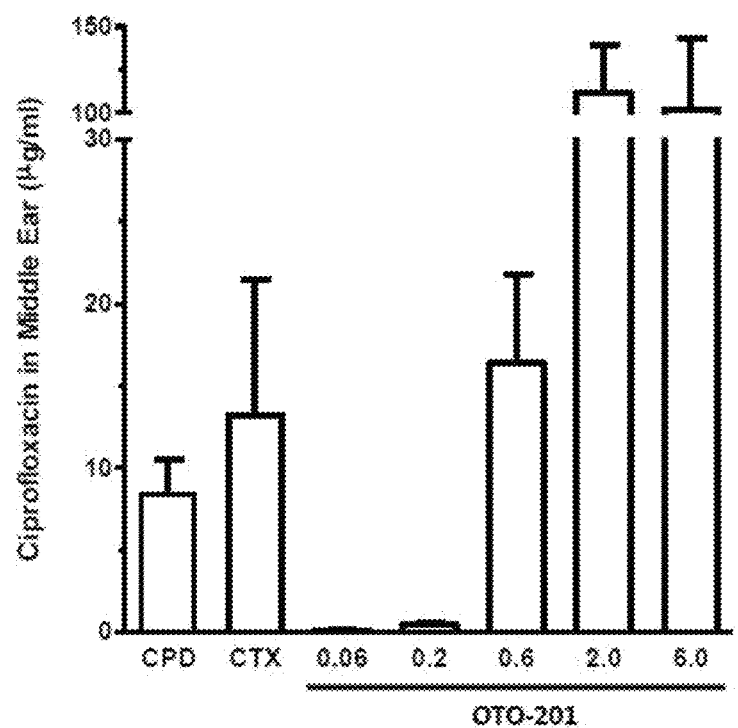
FIG. 9: Middle ear ciprofloxacin levels in chinchillas with otitis media treated with Composition A, CIPRODEX® or CETRAXAL®. The levels of free ciprofloxacin in the middle ear of treated chinchillas with OM was determined. Three days post treatment initiation, middle ear samples were collected and the concentration of ciprofloxacin determined. Data are presented as mean±SEM (n=6-13 ears). CPD: CIPRODEX®, CTX: CETRAXAL®.

Three days post treatment initiation, middle ear samples were collected and the concentrations of free ciprofloxacin in the middle ear were determined (FIG. 9).

of Composition A: Chinchillas received a single IT-ANT injection of various doses of Composition A as a single IT-ANT injection immediately prior to tympanostomy tube placement. A summary of the treatment regimens is presented in FIG. 2. Following the single IT-ANT administration of Composition A, ciprofloxacin concentrations were relatively low when 0.06% and 0.2% Composition A were given, at 0.1±0.0 µg/ml and 0.4±0.2 µg/ml, respectively. At higher Composition A doses, concentrations of ciprofloxacin were significant higher, from 16.4±5.4 µg/ml to 112.0±27.4 µg/ml. The concentrations observed were 2 to 13-fold higher than the ones reached with administration of CIPRODEX® or CETRAXAL®.

Administration of CIPRODEX® and CETRAXAL®: CIPRODEX® and CETRAXAL® were administered twice daily for 3 days to chinchillas. A summary of the treatment regimens is presented in FIG. 2. Following the twice daily for 3 days treatment course of CIPRODEX® or CETRAXAL®, ciprofloxacin levels were significant with values of 8.4±2.1 µg/ml and 13.2±8.3 µg/ml, respectively.

Example 4

Otic Tissue Assessments of Intratympanic Injection of Composition A in Guinea Pigs A one-month acute ototoxicity study was conducted in guinea pigs to compare the toxicological potential of Composition A to that of CIPRODEX® and CETRAXAL®. At termination, functional and anatomic assessments of the middle and inner ear compartments were conducted. Saline and the known ototoxicant gentamicin, both administered as a single IT-ANT injection, were included as negative and positive controls, respectively.

Example 4A

Auditory Brainstem Responses (ABR) Assessment

ABRs were recorded in an electrically and acoustically shielded chamber. Needle electrodes were placed at the vertex (active) and immediately below the pinna of the test ear (reference) and contralateral ear (ground). TDT System III hardware and SigGen/BioSig software (Tucker Davis Technologies) were used to present the stimulus and record the ABR responses. Tones were delivered through a Tucker-Davis EC1 driver (aluminum-shielded enclosure made in house), with the speculum placed just inside the tragus. Acoustic calibration was performed with TDT software (SigCal) and thresholds are expressed as dB SPL. Stimulus presentation (15 ms tone bursts, with 1 ms rise/fall times) was presented 10 per second. Up to 1024 responses were averaged for each stimulus level. Responses were collected for stimulus levels in 10 dB steps at higher stimulus levels, with additional 5 dB steps near threshold. Thresholds were interpolated between the lowest stimulus level where a response was observed, and 5 dB lower, where no response was observed.

Figure 10:
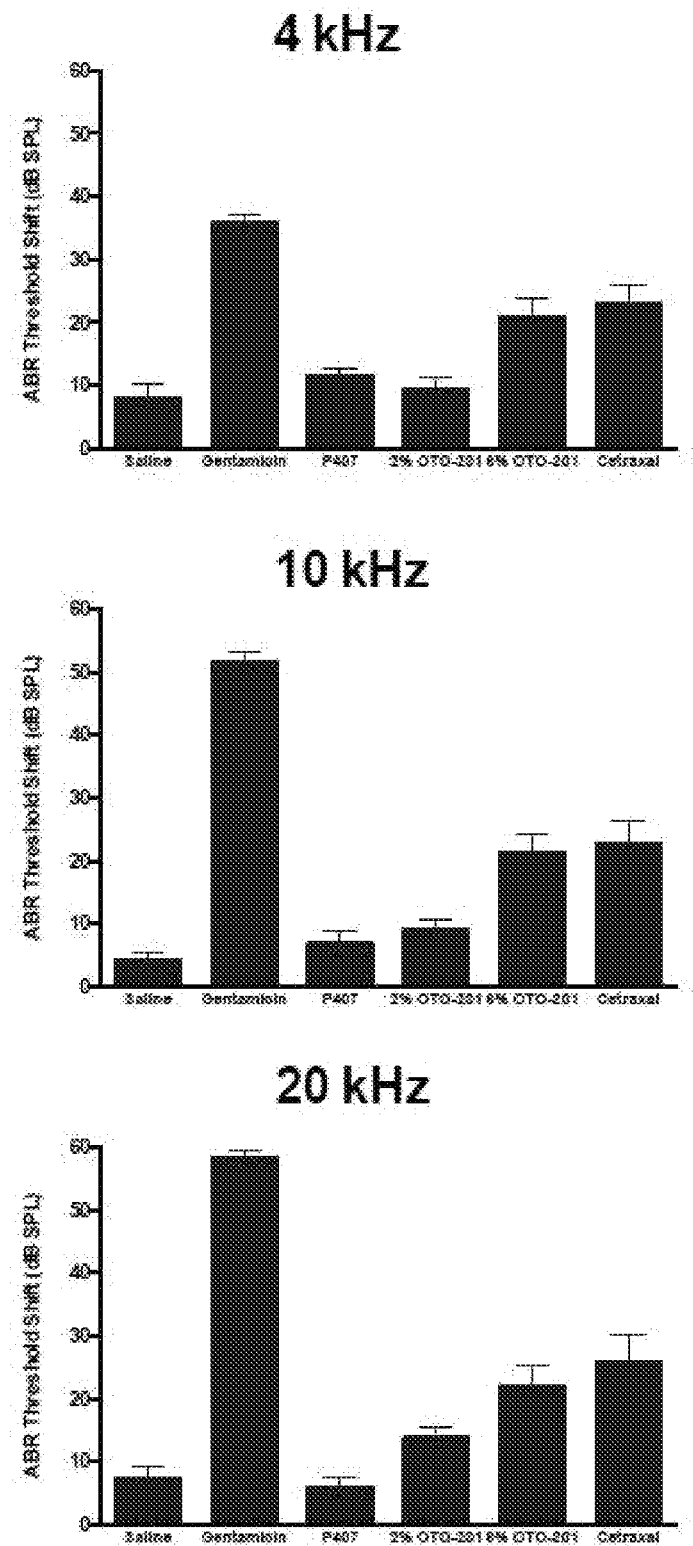
FIG. 10: Auditory function following administration of Composition A or CETRAXAL®. The auditory function of male and female guinea pigs was monitored using Auditory Brainstem Responses at baseline and termination. Animals received a single IT-ANT injection of poloxamer 407 vehicle, 2% or 6% Composition A, or a twice daily for 7 days treatment course of CETRAXAL®. Hearing threshold shifts were reported at low (4 kHz), medium (10 kHz) and high (20 kHz) frequencies. Data are presented as mean±SEM (n=5 per sex per group).

The auditory function of male and female guinea pigs was monitored using Auditory Brainstem Responses at baseline and termination (FIG. 10). Animals received a single IT-ANT injection of poloxamer 407 vehicle, 2% or 6% Composition A, or a twice daily for 7 days treatment course of CETRAXAL®. Hearing threshold shifts were reported at low (4 kHz), medium (10 kHz) and high (20 kHz) frequencies.

The variability of the baseline ABR thresholds was similar between guinea pigs assigned to the different treatment groups at each tested frequency. Mean ABR thresholds in the saline group increased marginally from baseline upon study completion across frequencies ($\leq$10 dB SPL). IT-ANT administration of the known ototoxicant gentamicin (400 mg/ml) resulted in severe ABR threshold shifts ($\geq$40-60 dB SPL) across frequencies. Following administration of the vehicle P407, minimal elevations in ABR threshold were observed across frequencies ($\leq$10 dB SPL), comparable to that seen with saline. In the Composition A treatment groups (2% and 6%), a dose-dependent mild ABR threshold shift was evident at termination (10-20 dB SPL) across the frequencies tested, with 2% Composition A exhibiting ABR shifts comparable to saline. The twice daily for 7 days CETRAXAL® treatment course generally resulted in mild to moderate hearing loss at termination (20-30 dB SPL) across frequencies. Overall, Composition A treatment was associated with minimal to mild ABR threshold shift across the frequencies tested, and compared favorably to CETRAXAL® treatment, which was associated with mild to moderate hearing loss.

Example 4B

Middle Ear Histology

Male and female guinea pigs (n=5 per sex, per group) received a single IT-ANT injection of poloxamer 407 vehicle, 2% or 6% Composition A, or a twice daily for 7 days treatment course of CIPRODEX® or CETRAXAL®. Histological analysis of middle ear paraffin sections was conducted at termination.

Middle ear histology—Guinea pigs received vascular perfusion through the heart with an isotonic saline solution followed by fixative containing 4% paraformaldehyde (PFA) in phosphate buffer. Left and right temporal bones were removed and trimmed. Left ear cochleae were designated for inner ear assessment and the right ear cochleae for middle ear histology. Cochleae of the left ear were fixed by intrascalar perfusion of 4% PFA. The temporal bones were then placed in 4% PFA for approximately 1 hour and transferred to a vial containing 0.5% PFA in phosphate buffer. The right temporal bones were trimmed, and then each was placed in a cassette containing 5% EDTA in phosphate buffer. The cassettes were placed into a PELCO 3451 Microwave System, running constantly for 3-5 days. Ears were then dehydrated in EtOH and processed in JB-4 Glycol Methacrylate resin, placed into molds containing the resin and polymerized at ~4° C. for ~12 h. Blocks containing temporal bones were trimmed and 5 µm sections were cut with a Leica RM2165 Microtome and stained with Paragon stain. Sections were examined under bright field optics. Middle ear sections were assessed for tissue reaction and inflammatory response. Mild tissue reaction was defined as small increases in the thickness of the tissue associated with mucosal linings with some possible vesiculation. Mild— moderate tissue reaction was defined as small regions of new tissue growth or inflammatory response. Moderate tissue reaction was defined as larger tissue growth often associated with an inflammatory response. Moderate to large tissue reaction was defined as several regions with large amounts of new tissue growth and cells associated with inflammatory response. Large response was defined as a large tissue growth and inflammatory response associated with much to all of the middle ear often with new bone growth.

Figure 11:
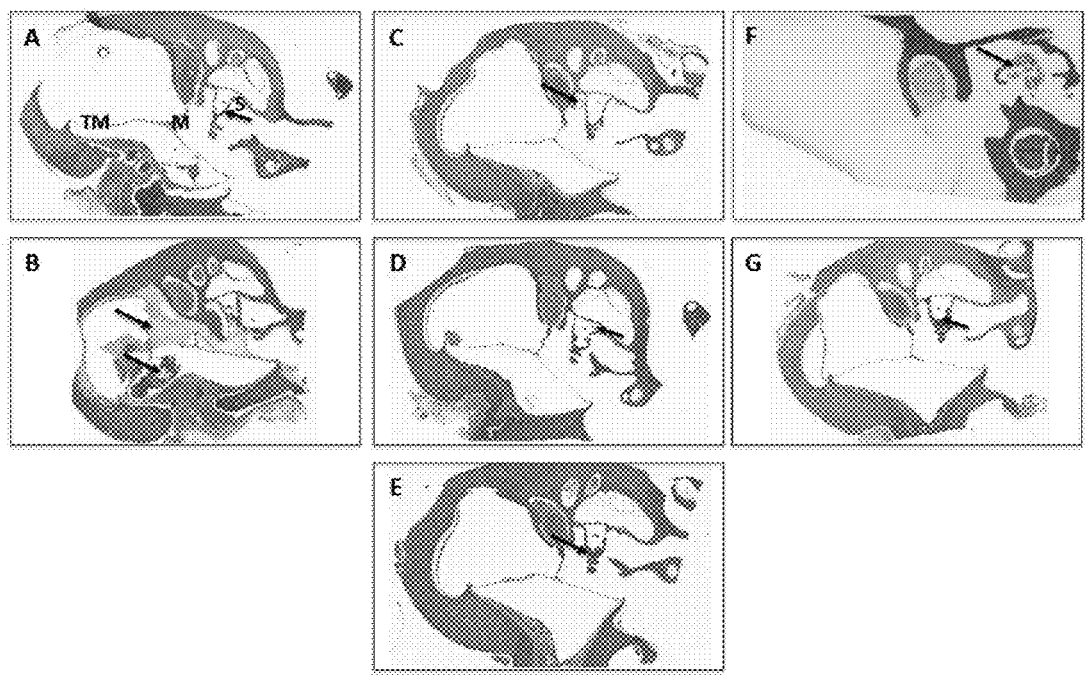
FIG. 11: Middle ear histology following administration of Composition A, CIPRODEX® or CETRAXAL®. Male and female guinea pigs (n=5 per sex, per group) received a single IT-ANT injection of poloxamer 407 vehicle, 2% or 6% Composition A, or a twice daily for 7 days treatment course of CIPRODEX® or CETRAXAL®. Representative tissue sections of the middle ear (at termination) from guinea pigs treated with saline (A), gentamicin (B), P407 vehicle (C), 2% Composition A (D), 6% Composition A (E), CIPRODEX® (F) and CETRAXAL® (G) are presented. Legend: M: malleus, S: stapes, TM: tympanic membrane. Arrows make references of: (A) foamy macrophages; (B) upper arrow: fibroplasia and inflammation, lower arrow: mixed cellular and proteinaceous debris; (C) foamy macrophages; (D) foamy macrophages; (E) granulomatous inflammation; (F) reactive cells; (G) basophilic foamy macrophages.

Assessments focused on tissue reaction and inflammatory response in the region of the tympanic membrane and the middle ear. Histology of the middle ear revealed the presence of minimal subacute inflammation in the vast majority of animals treated with saline, poloxamer 407 vehicle, Composition A (2% and 6%), CIPRODEX® and CETRAXAL® (FIG. 11). The known ototoxicant gentamicin caused moderate chronic inflammation in all treated ears, and associated moderate to severe fibroplasia, mild hemorrhage and bone remodeling. The findings observed in all treatment groups, with the exception of gentamicin, were considered secondary to the intratympanic injection procedure and tympanostomy tube placement.

Example 4C

Inner Ear Cytocochleogram

Male and female guinea pigs (n=5 per sex, per group) received a single IT-ANT injection of poloxamer 407 vehicle, 2% or 6% Composition A, or a twice daily for 7 days treatment course of CIPRODEX® or CETRAXAL®.

Inner ear cytocochleogram—The left ear cochleae were carefully removed from the temporal bones and then further dissected, first removing the bony otic capsule, followed by removal of lateral wall tissues, including spiral ligament and stria vascularis. The tectorial membrane was then removed and the cochleae placed in a solution of rhodamine labeled phalloidin, diluted 1:100 in phosphate buffered saline (PBS), for 30-120 min, in the dark, followed by two washes in PBS. The cochlear sensory neural epithelium was then dissected away from the modiolus, starting at the apex, to produce surface preparations of the cochlear spiral. Each segment was mapped for location and placed on a slide. A quantitative assessment of presence or absence of hair cells was then carried out, beginning at apex and proceeding to the base, to produce a cytocochleogram, with presence or absence or hair cells mapped by position along the cochlear spiral.

Figure 12:
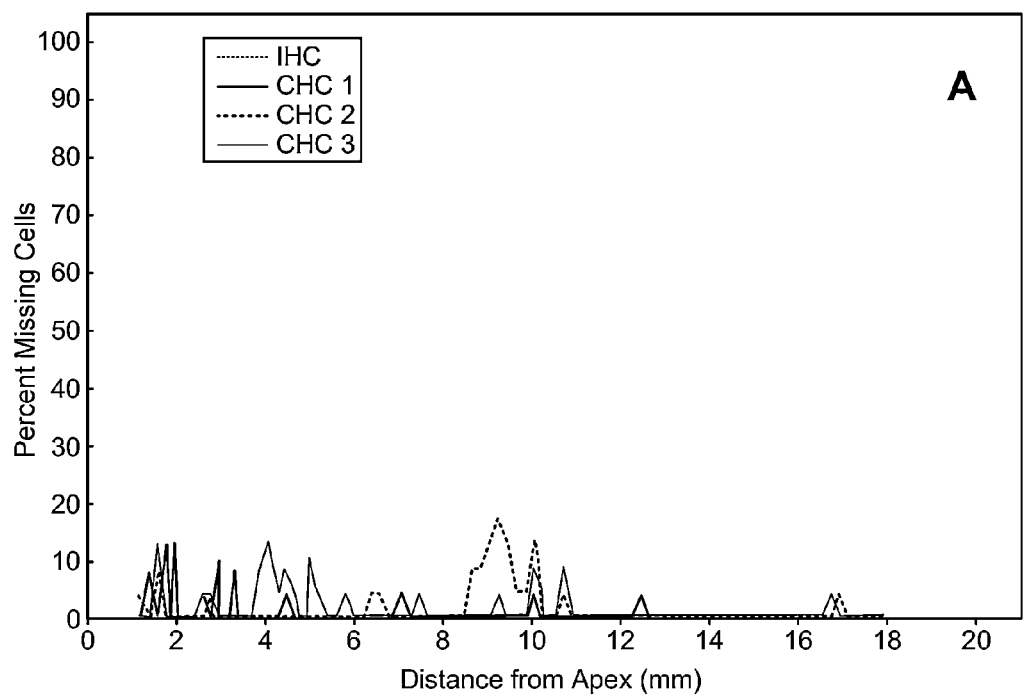
FIG. 12: Inner ear cytocochleogram following administration of Composition A, CIPRODEX® or CETRAXAL®. Male and female guinea pigs (n=5 per sex, per group) received a single IT-ANT injection of poloxamer 407 vehicle, 2% or 6% Composition A, or a twice daily for 7 days treatment course of CIPRODEX® or CETRAXAL®. Representative cytocochleograms (at termination) mapping the presence or absence of inner hair cells (black line) and the three rows of outer hairs (row 1—red line; row 2—blue line; row 3—green line) by position along the cochlear spiral, with apex on the left and base on the right, from the cochleae of treated guinea pigs having received saline (A), gentamicin (B), P407 vehicle (C), 2% Composition A (D), 6% Composition A (E), CIPRODEX® (F) and CETRAXAL® (G).
Figure 12:
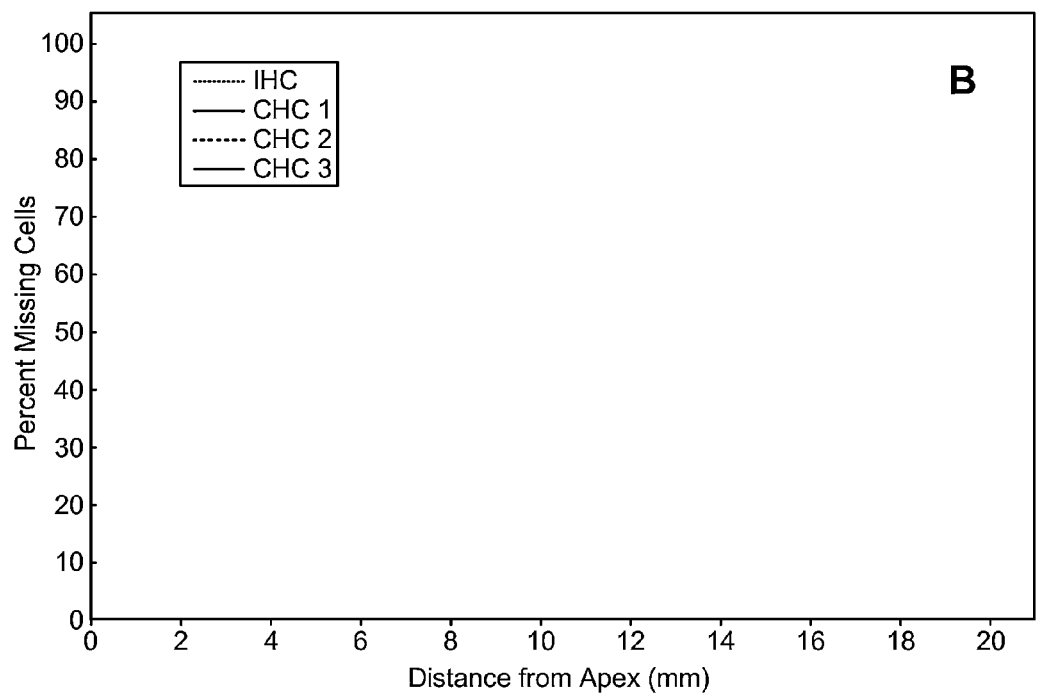
Figure 12:
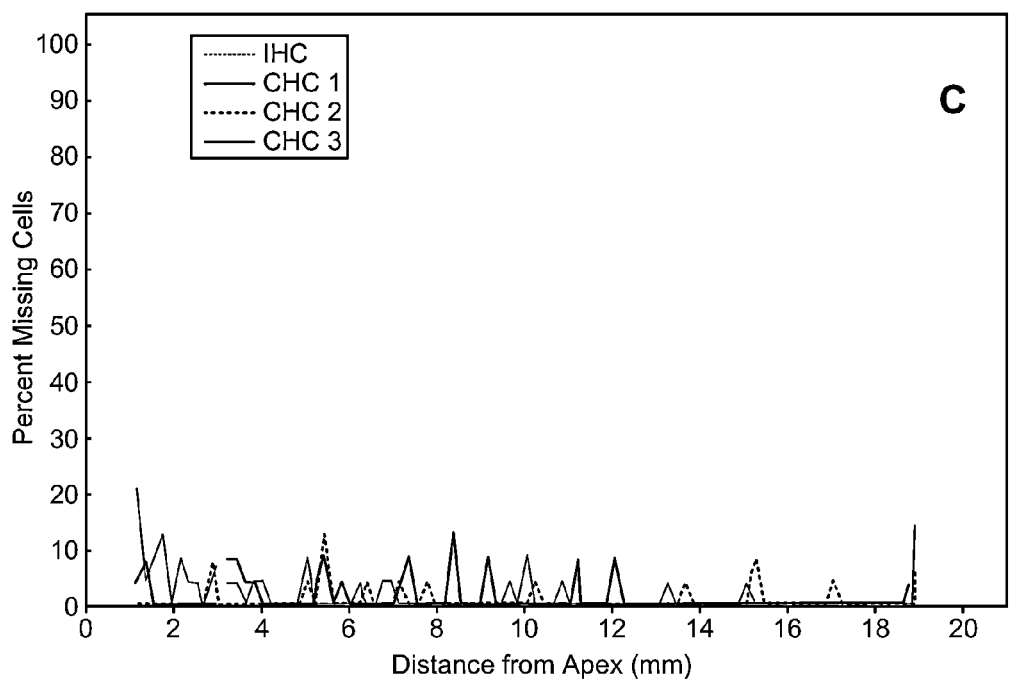
Figure 12:
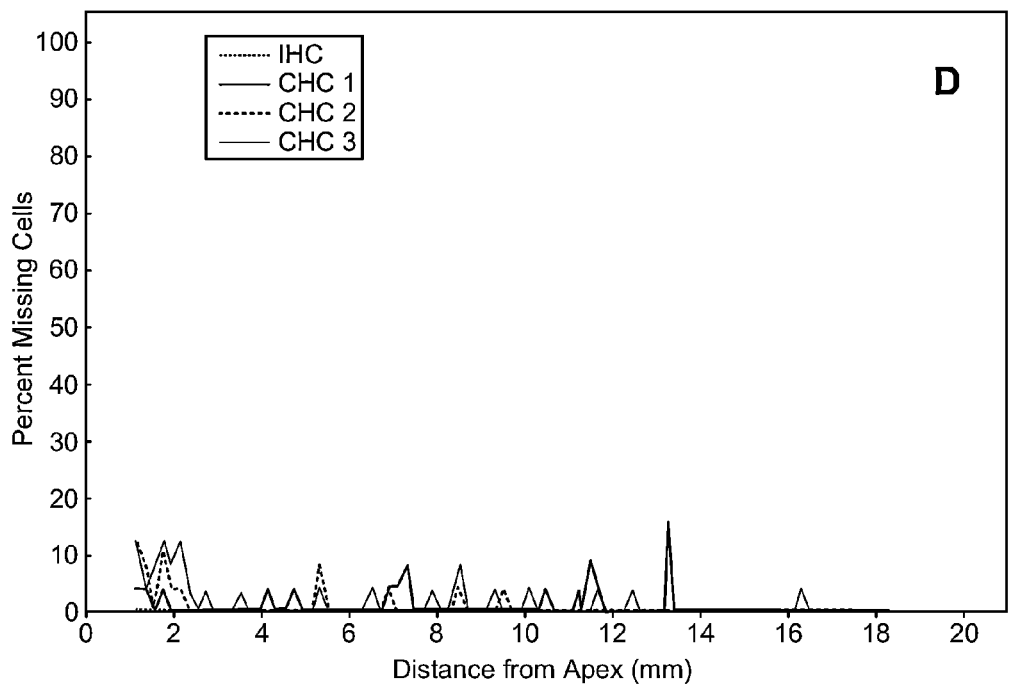
Figure 12:
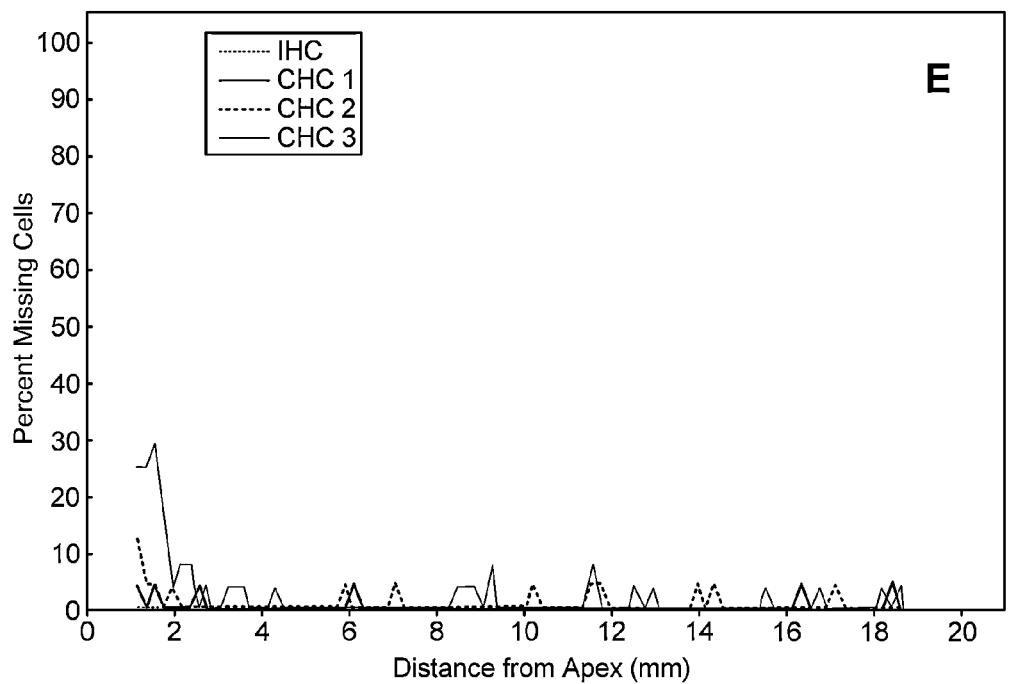
Figure 12:
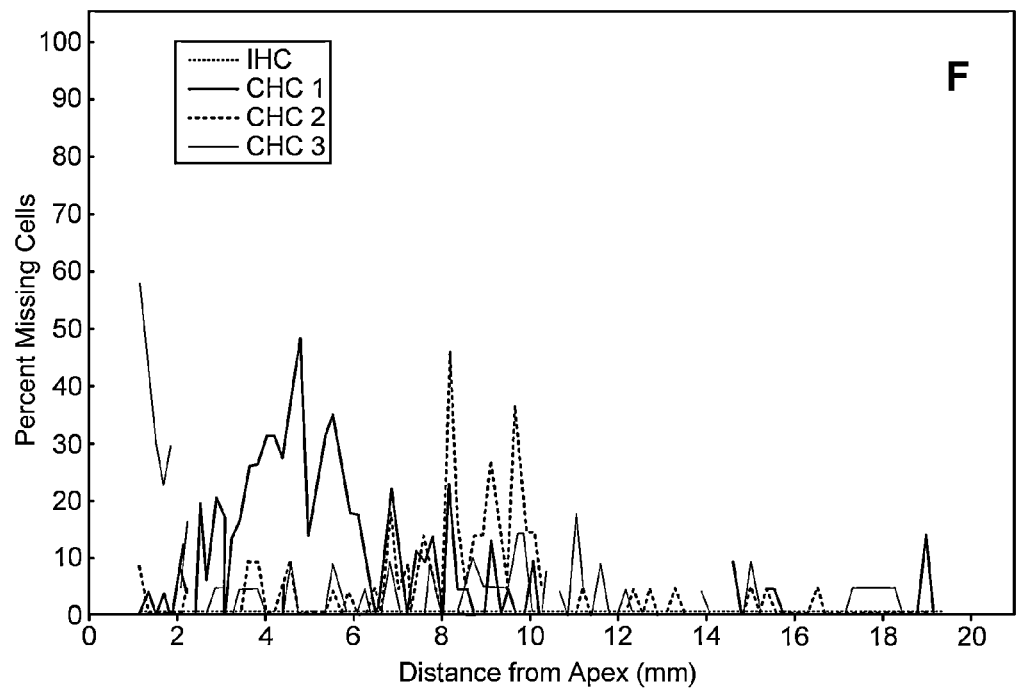
Figure 12:
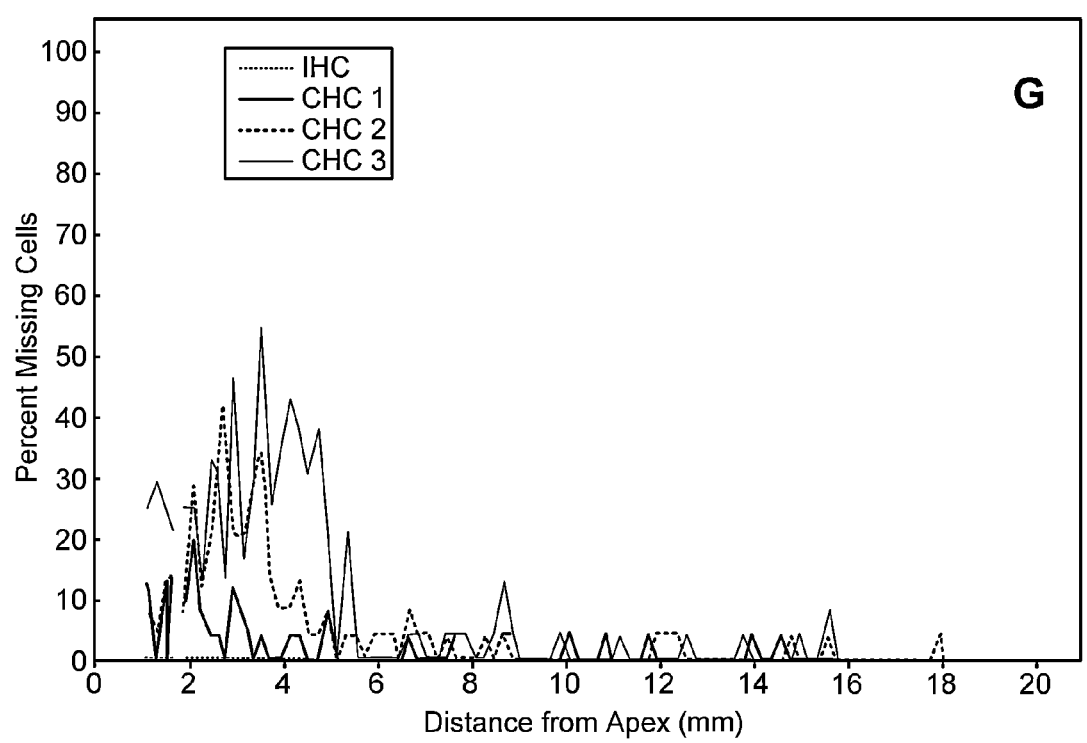

The integrity of the sensorineural epithelium was examined in a quantitative assessment of inner and outer hair cells from surface preparations of the cochlear spiral generating cytocochleograms (FIG. 12). IT-ANT administration of saline was not associated with hair cell loss in any of the treated animals, while administration of the known ototoxicant gentamicin resulted in profound to complete hair cell loss. IT-ANT administration of poloxamer 407 vehicle was not associated with hair cell loss in any of the treated animals, similarly to saline. OTO 201 at doses of 2% and 6% did not produce otopathology, with no evidence of outer and inner hair cell loss. In contrast, both CIPRODEX® and CETRAXAL® group produced mild to moderate hair cell loss (outer only), primarily confined to the apical half of the cochlea.

Example 4D

Tympanostomy Tube Patency

Figure 13:
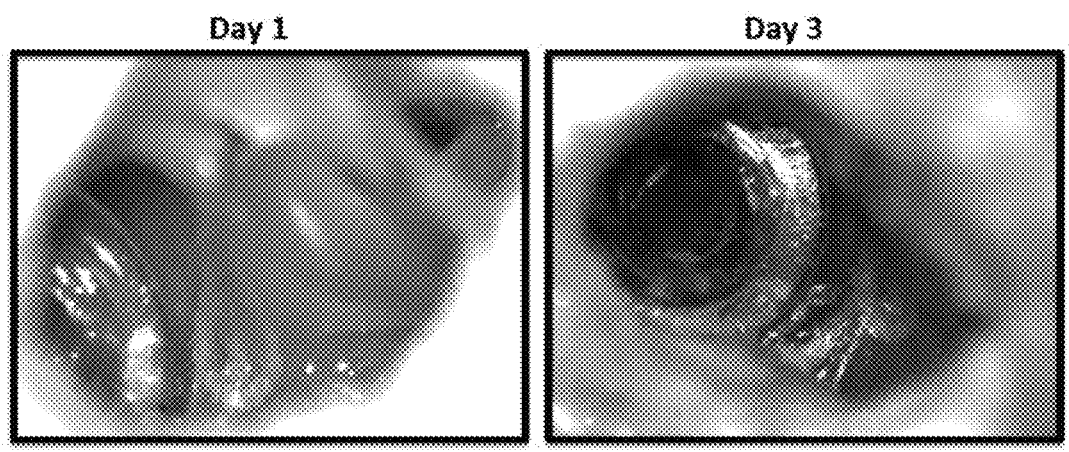
FIG. 13: Tympanostomy tube patency. Pictures of the tympanic membrane region depicting the patency at Day 1 and Day 3 following IT-ANT administration in guinea pigs of poloxamer 407 vehicle (dyed with Evans Blue), immediately prior to tympanostomy tube placement.

Tympanostomy tube patency was examined. The presence or absence of clogging of the ventilation tube by the P407 hydrogel was evaluated by visualization under a surgical microscope. Following IT-ANT administration of poloxamer 407 vehicle to the middle ear of guinea pigs immediately prior to ventilation tube placement, there was no evidence of tube clogging at Day 1 and Day 3 post-treatment (FIG. 13). Thus, the presence of poloxamer 407 hydrogel in the middle ear does not affect the patency of ventilation tubes inlayed through the tympanic membrane.

Example 5

Clinical Trial of Antimicrobial Agent Formulations in Combination with Tympanostomy for Treatment of Pediatric Otitis Media with Effusion The purpose of this study is to determine if a composition comprising Ciprofloxacin and poloxamer 407 administered in combination with a tympanostomy is safe and effective in preventing and/or treating middle ear infections in pediatric patients with ear tubes.

Study Type: Interventional

Study Design: This is a randomized, double-blind, placebo- and sham-controlled, multicenter, dose escalation Phase 1b study of Composition A administered intra-operatively in pediatric subjects with bilateral middle ear effusion who require tympanostomy tube placement. Two dose levels of Composition A are evaluated relative to placebo (vehicle only) and sham (no vehicle). Within each dose cohort, subjects are randomized to either Composition A, placebo or sham using a 2:1:1 allocation ratio; the cohorts will be stratified by age: 1) 6 months to 2 years, or 2) greater than 2 years.

Cohort 1:
  Diluted Composition A 4 mg; single 200 µL intratympanic injection in each ear
  Placebo (Vehicle) for Composition A; single 200 µL intratympanic injection in each ear
  Sham Injection Cohort 2:
  Composition A 12 mg; single 200 µL intratympanic injection in each ear
  Placebo (Vehicle) for Composition A; single 200 µL intratympanic injection in each ear
  Sham Injection Dose and Mode of Administration:
  4 mg Diluted Composition A (4 mg ciprofloxacin in 16% poloxamer 407), single bilateral 200 µL intratympanic injections The 4 mg Diluted Composition A final product suspension for dosing is prepared on site at the clinic from two separate vials, 6% Composition A Drug Product and Composition A Diluent. An appropriate volume of both 6% Composition A Drug Product and Composition A Diluent is withdrawn and added to an empty vial and mixed to achieve a visually homogeneous suspension of the target drug concentration.

12 mg Composition A (12 mg ciprofloxacin in 16% poloxamer 407), single bilateral 200 µL intratympanic injections.

The 12 mg Composition A is supplied from one vial (6% Composition A Drug Product).

Placebo consists of the vehicle used to formulate Composition A and is supplied from one vial (Composition A Diluent). Subjects assigned to sham receive a sham injection with an empty syringe.

Each dose of Composition A or placebo is administered as a single, intratympanic injection into each ear. The recommended injection procedure for intratympanic administration of Composition A, placebo or sham is as follows:
1. Place myringotomy site where clinically indicated
2. Collect culture specimen and remove remaining middle ear fluid
3. Using a tuberculin syringe, direct 2000 µL of Diluted Composition A, Composition A or placebo anterior and inferior to the myringotomy site through the open tympanic membrane
   a. For sham injections, the syringe is prepped to the 2000 µL graduation on the syringe; however, the syringe will not contain any material
4. Place ventilation tube after administration of Composition A, placebo or sham Duration of Treatment: Single bilateral 200 µL intratympanic injection Methodology: Subjects have a clinical diagnosis of bilateral middle ear effusion requiring tympanostomy tube (TT)

placement. On the day of surgery, prior to surgery, eligible subjects entering the first cohort are examined to confirm bilateral middle ear effusion. Subjects with bilateral middle ear effusion are randomized to either 4 mg Diluted Composition A, placebo or sham. When at least 18 subjects in the 4 mg dose cohort have completed the Day 15 visit, a Data Review Group (DRG) reviews all safety data to date. If no safety issues are identified by the DRG, enrollment of eligible subjects with bilateral middle ear effusion into the second dose cohort begins. Subjects in the second dose cohort with bilateral middle ear effusion on the day of surgery, prior to surgery, are randomized to either 12 mg Composition A, placebo or sham. When both cohorts are enrolling simultaneously, subjects are first randomized to one of the two cohorts and then to either Composition A, placebo or sham. Subjects without bilateral effusion on day of surgery are not randomized.

Within each dose cohort, 40 subjects are randomized to Composition A, placebo or sham using a 2:1:1 allocation ratio. Randomization to study drug within each cohort is stratified by age: 1) 6 months to 2 years, or 2) greater than 2 years.

During surgery, a culture of the effusion from each ear is obtained prior to Composition A, placebo or sham injection. Composition A, placebo or sham is administered in both ears following myringotomy. All syringes, including sham, are prepared to maintain the blind. Following administration of Composition A, placebo or sham and subsequent TT placement, caregivers and subjects receive standard post-operative instructions.

Composition A, placebo or sham syringes are prepared by an unblinded qualified health care professional at the investigative site not otherwise associated with the trial. The pediatric otolaryngologist becomes unblinded at the time of Composition A, placebo or sham administration based on the appearance of the treatment being administered. Caregivers, subjects, and study staff are blinded to treatment.

During Days 1 through 29, caregivers report the presence of otorrhea daily using an interactive voice response system (IVRS). In addition, caregivers are instructed to bring the subject to the study site for examination if otorrhea in one or both ears is observed on or after 3 days post-surgery (Day 4). A blinded investigator who was not involved in the administration of study drug assesses the presence of otorrhea, and if present, a specimen is collected for culture.

Subjects visit the study site on Days 4, 8, 15 and 29 for safety assessments and otoscopic examination. The assessment of otorrhea for the clinical activity endpoint occurs on Days 4, 8, and 15 by the blinded investigator. Subjects with visible otorrhea in the auditory canal on external examination by the blinded investigator are considered "treatment failures" if otorrhea is observed on or after 3 days post-surgery (Day 4) through Day 15. Treatment failures are eligible for rescue medication and are considered treatment failures for the remainder of the study. Subjects designated as treatment failures are asked to remain on-study and continue to be monitored for safety.

Inclusion Criteria:
Subjects meeting all of the following criteria may be eligible for the study:
1. Subject is a male or female aged 6 months to 12 years, inclusive
2. Subject has a clinical diagnosis of bilateral middle ear effusion requiring tympanostomy tube placement
3. Subject's caregiver is willing to comply with the protocol and attend all study visits
4. Subject's caregiver is able to use the telephone and understand and respond to English or Spanish
5. Subject's caregiver is able to provide written informed consent and Health Insurance Portability and Accountability Act (HIPAA) of 1996 documents before the initiation of any study-related procedures
6. Subject of appropriate age is able to provide assent for participation in the study Exclusion Criteria:
Subjects meeting any of the following criteria are not eligible for participation:
1. Subject has a history of prior ear or mastoid surgery, not including myringotomy or myringotomy with TT placement
2. Subject has been designated for any other surgical procedure that would occur concurrently with TT placement, such as, but not limited to adenoidectomy or tonsillectomy
3. Subject has a history of sensorineural hearing loss
4. Subject has a history of chronic or recurrent bacterial infections other than otitis media that likely will require treatment with antibiotics during the course of the study
5. Subject has tympanic membrane perforation
6. Subject has a history of known immunodeficiency disease
7. Subject has an abnormality of the tympanic membrane or middle ear that would preclude precise placement of study drug or intratympanic injection
8. Use of topical nonsteroidal otic agents within 1 day of randomization
9. Use of topical or otic corticosteroids within 3 days of randomization or systemic corticosteroids within 7 days of randomization
10. Presence of any infection requiring systemic antimicrobial or antifungal agents
11. Use of topical or systemic antimicrobial or antifungal agents; amoxicillin, Augmentin®, Omnicef®, ceftriaxone, and cephalexin within 3 days of randomization; doxycycline and fluoroquinolones within 7 days and Zithromax® within 14 days of randomization
12. Concurrent use of oral anti-inflammatory agents
13. Subject has a history of allergy to ciprofloxacin or any of the components of Composition A
14. Subject has any other clinically significant illness or medical condition that, in the opinion of either the investigator or medical monitor, would prohibit the subject from participating in the study
15. Subject has used an investigational drug or device in the month prior to screening
16. Subject has been previously exposed to Composition A
17. Subject is a menarcheal or post-menarcheal female
18. Subject is not able to complete all baseline assessments. For subjects 4 years or younger, the subject must complete, at a minimum, DPOAE in both ears and VRA in one ear at two frequencies, using both air and bone conduction in order to be eligible for enrollment.

Outcome Measures for Evaluation:
Safety Endpoints:
Safety assessments include:
  Adverse events
  Otoscopic examinations
  Tympanometry assessments
  Audiometry assessments—Conventional audiometry assessments, including air conduction and bone conduction, are performed on subjects that are mature enough to participate, as determined by the investigator, typically age 4 years and older.

Visual Reinforcement Audiometry (VRA), using air conduction and bone conduction, and distortion product otoacoustic emission (DPOAE) assessments are performed on all subjects not mature enough for conventional audiometry, typically below the age of 4 years.

Vital sign measurements

Physical examinations

Clinical Activity Endpoints:

Clinical activity assessments include:

The proportion of treatment failures defined as any subject receiving rescue medications at any time post-surgery or having physician documented otorrhea at any time on or after 3 days post-surgery in one or both ears through each of the following time points:

Day 4

Day 8

Day 15

Time-to-otorrhea based on caregiver diaries, defined as:
The time-to-caregiver observed otorrhea on or after 3 days post-surgery through Day 15
The time-to-caregiver observed otorrhea beginning on the first calendar day post-surgery through Day 15

Receipt of rescue medication as defined above applies for this endpoint.

Microbiological eradication (absence, presumed or documented) of pretherapy bacteria based on comparison to any bacteria in otorrhea present at any visit, Day 4 through Day 15 inclusive.

Day 29 Evaluations: Exploratory analyses also examine each of the clinical activity endpoints noted above through Day 29.

Safety

Safety is assessed through Day 29. Safety endpoints are summarized for each Composition A dose group as well as the placebo and sham control groups for both the individual cohorts and pooled across cohorts. Examination of any potential dose-response relationship with respect to safety outcomes are also assessed. If no significant adverse event (AE) is observed, a sample size of 20 subjects per dose cohort receiving Composition A (4 mg or 12 mg in each ear, total dose of 8 mg or 24 mg) would be expected to "rule-out" an AE with a subject incidence rate of approximately 0.14 or more with 95% confidence. Although this quantitative information is helpful in assessing potential safety issues, decisions with regard to dose escalation are based on expert medical review of the emerging safety profile.

Clinical Activity

The primary clinical activity endpoint is the proportion of treatment failures defined as any subject receiving rescue medications at any time post-surgery or having physician documented otorrhea at any time on or after 3 days post-surgery in one or both ears. For this Phase 1b study, three separate time points are examined: Days 4, 8 and 15. Subjects with physician documented otorrhea in either ear 3 days post-surgery or receiving rescue medications at any time post-surgery are defined as a treatment failure from the earliest time point of either event through all subsequent time points.

Additional exploratory analyses examine clinical activity endpoints in the subset of subjects who were culture positive at the time of TT placement. Analyses explore differences between Composition A, placebo and sham control groups, both within individual dose cohorts as well as comparisons of the two Composition A doses to the pooled placebo group and the pooled sham group across cohorts.

Given the primary safety objective, the study is not designed to provide adequate power for statistical hypothesis testing. Therefore, the analysis of clinical activity is primarily descriptive and considered exploratory.

Example 6

Clinical Trial of Antimicrobial Agent Formulations in Combination with Tympanostomy for Treatment of Pediatric Otitis Media with Effusion The purpose of this study is to determine if a composition comprising Ciprofloxacin and poloxamer 407 administered in combination with a tympanostomy is safe and effective in preventing and/or treating middle ear infections in pediatric patients with ear tubes.

Study Type: Interventional

Study Design: This is a randomized, double-blind, sham-controlled, multicenter, Phase 3 study of 6 mg Composition A administered intra-operatively in pediatric subjects with bilateral middle ear effusion who require tympanostomy tube placement. One dose level of Composition A (6 mg ciprofloxacin, 100 µL) is evaluated relative to sham (empty syringe). Subjects are randomized to either 6 mg Composition A (6 mg ciprofloxacin, 100 µL), or sham using a 2:1 allocation ratio; the subjects are be stratified by age: 1) 6 months to 2 years, or 2) greater than 2 years.

Composition A (6 mg ciprofloxacin); single 100 µL intra-tympanic injection in each ear Sham Injection Dose:

6 mg Composition A (6 mg ciprofloxacin in 16% poloxamer 407), single bilateral 100 nt intratympanic injections.

Duration of Treatment: Single bilateral 100 nt intratympanic injection

Methodology: Subjects have a clinical diagnosis of bilateral middle ear effusion requiring tympanostomy tube (TT) placement. On the day of surgery, prior to surgery, eligible subjects entering the first cohort are examined to confirm bilateral middle ear effusion. Subjects with bilateral middle ear effusion are randomized to either 6 mg Composition A or sham. Subjects without bilateral effusion on day of surgery are not randomized.

Subjects are randomized to 6 mg Composition A or sham using a 2:1 allocation ratio. Randomization to study drug is stratified by age: 1) 6 months to 2 years, or 2) greater than 2 years.

During surgery, a culture of the effusion from each ear is obtained prior to 6 mg Composition A or sham injection. 6 mg Composition A or sham is administered in both ears following myringotomy. All syringes, including sham, are prepared to maintain the blind. Following administration of 6 mg Composition A or sham and subsequent TT placement, caregivers and subjects receive standard post-operative instructions.

6 mg Composition A or sham syringes are prepared by an unblinded qualified health care professional at the investigative site not otherwise associated with the trial. The pediatric otolaryngologist becomes unblinded at the time of 6 mg Composition A or sham administration based on the appearance of the treatment being administered. Caregivers, subjects, and study staff are blinded to treatment.

Caregivers are instructed to bring the subject to the study site for examination if otorrhea in one or both ears is observed on or after 3 days post-surgery (Day 4). A blinded investigator who was not involved in the administration of study drug assesses the presence of otorrhea, and if present, a specimen is collected for culture.

Subjects visit the study site on Days 4, 8, 15 and 29 for safety assessments and otoscopic examination. The assessment of otorrhea for the clinical activity endpoint occurs on Days 4, 8, and 15 by the blinded investigator who looks for visible otorrhea in the auditory canal on external examination. Once the blinder investigator determines the presence of visible otorrhea, subjects are eligible for rescue medication.

The primary efficacy endpoint is the cumulative proportions for otic treatment failures through the Day 15 visit. An otic treatment failure is defined as any subject receiving otic antibiotic drops at any time post-surgery or having documented otorrhea by the blinded investigator at any time on or after 3 days post-surgery (Day 4) in one or both ears through the Day 15 visit. Subjects are defined as an otic treatment failure from the earliest time point of either event as defined above and considered an otic treatment failure for the remainder of the study. Subjects designated as treatment failures are asked to remain on-study and continue to be monitored for safety.

Inclusion Criteria:
Subjects meeting all of the following criteria may be eligible for the study:
1. Subject is a male or female aged 6 months to 12 years, inclusive
2. Subject has a clinical diagnosis of bilateral middle ear effusion requiring tympanostomy tube placement
3. Subject's caregiver is willing to comply with the protocol and attend all study visits
4. Subject's caregiver is able to provide written informed consent and Health Insurance Portability and Accountability Act (HIPAA) documents before the initiation of any study-related procedures
5. Subject of appropriate age is able to provide assent for participation in the study Exclusion Criteria:
Subjects meeting any of the following criteria are not eligible for participation:
1. Subject has a history of prior ear or mastoid surgery, not including myringotomy or myringotomy with TT placement
2. Subject has been designated for any other surgical procedure that would occur concurrently with TT placement, such as, but not limited to adenoidectomy or tonsillectomy
3. Subject has a history of sensorineural hearing loss
4. Subject has a history of chronic or recurrent bacterial infections other than otitis media that likely will require treatment with antibiotics during the course of the study
5. Subject has tympanic membrane perforation
6. Subject has a history of known immunodeficiency disease
7. Subject has an abnormality of the tympanic membrane or middle ear that would preclude precise placement of study drug or intratympanic injection
8. Use of topical nonsteroidal otic agents within 1 day of randomization
9. Use of topical or otic corticosteroids within 3 days of randomization or systemic corticosteroids within 7 days of randomization
10. Presence of any infection requiring systemic antimicrobial or antifungal agents
11. Use of topical or systemic antimicrobial or antifungal agents; amoxicillin, Augmentin®, Omnicef®, ceftriaxone, and cephalexin within 3 days of randomization; doxycycline and fluoroquinolones within 7 days and Zithromax® within 14 days of randomization
12. Concurrent use of oral anti-inflammatory agents
13. Subject has a history of allergy to ciprofloxacin or any of the components of Composition A
14. Subject has any other clinically significant illness or medical condition that, in the opinion of either the investigator or medical monitor, would prohibit the subject from participating in the study
15. Subject has used an investigational drug or device in the month prior to screening
16. Subject has been previously exposed to Composition A
17. Subject is a menarcheal or post-menarcheal female
18. Subject is not able to complete all baseline assessments.

Outcome Measures for Evaluation:
Safety Endpoints:
Safety assessments include:
  Adverse events
  Otoscopic examinations
  Tympanometry assessments
  Audiometry assessments—Conventional audiometry assessments, including air conduction and bone conduction, are performed on subjects that are mature enough to participate, as determined by the investigator, typically age 4 years and older.
  Vital sign measurements
  Physical examinations Primary Efficacy Endpoints:
  The primary efficacy endpoint is the cumulative proportion of otic treatment failures through the Day 15 visit. An otic treatment failure is defined as any subject receiving otic antibiotic drops at any time post-surgery or having documented otorrhea by the blinded assessor at any time on or after 3 days post-surgery (Day 4) in one or both ears through the Day 15 visit. Subjects will be defined as an otic treatment failure from the earliest time point of either event as defined above and considered an otic treatment failure for the remainder of the study. Subjects whose treatment failure status is unknown at the scheduled Day 15 visit due to loss-to-followup, study termination, or a missed visit, will be classified as a treatment failure for the primary analysis. The test of efficacy will be the difference between the proportion of otic treatment failures through the Day 15 visit between the 6 mg Composition A group and the sham group.

Secondary Efficacy Endpoints:
  The cumulative proportion of otorrhea at any time on or after 3 days post-surgery in one or both ears through Day 15. The cumulative proportion of treatment failures defined as any subject receiving otic rescue medications and/or systemic antibiotic medication at any time post-surgery or having physician documented otorrhea at any time on or after 3 days post-surgery in one or both ears through Day 15. Microbiological eradication (absence, presumed or documented) of pre-therapy bacteria based on comparison to any bacteria in otorrhea present at any visit, Day 4 through Day 15 inclusive.

Statistical Methods:
Sample Size:
  To estimate the sample size for the current trial several assumptions were made. First, to account for sampling variability in the P1b trial, a treatment effect was assumed that was smaller than that observed in the P1b. Second, a lost-to-follow-up rate resulting in unknown Day 15 treatment failure status due to early withdrawal or missed visits was estimated to be 5%. Assuming subjects with an unknown treatment failure status would be analyzed as a treatment failure for the primary analysis, a dilution of the estimated treatment effect was incorporated. Lastly, due to revised entry criteria, it is anticipated that the mix of younger subjects (6-months to 2 years) will comprise approximately 60% of the total sample size with subjects greater than 2 years comprising the remaining 40% of the sample. Although the P1b trial had a 50:50 mix of younger to older subjects, the data suggested the possibility of a larger treatment effect for younger subjects, albeit older subjects were also observed to benefit from treatment with OTO-201. As such, an adjustment to the overall treatment effect based on an enriched sample with approximately 60% younger subjects was also incorporated into the sample size calculations.

In a non-limiting example, the 6 mg Composition A treatment effect based on the difference between the 6 mg Composition A and sham otic treatment failure proportions is estimated to be −0.21 and is based on treatment failure rates in the 6 mg Composition A and sham groups of 0.25 and 0.46, respectively. A Z-test for the difference between two independent proportions using a pooled variance estimate with a two-tailed alpha level of 0.05 and a 2:1 allocation ratio was used to estimate power and sample size. The study has an approximate power of 93% to reject the null hypothesis of no difference. The current sample size would also yield a power, 88%, if the lost-to-follow-up rate increases to 10% and would provide additional power if the mix of younger subjects is greater than 60%.

Safety:

Safety will be assessed through Day 29. Safety endpoints will be summarized for the 6 mg Composition A dose group as well as the sham control group for the safety population—subjects receiving at least one dose of study drug or a sham injection.

Primary Efficacy Endpoint:

The proportion of otic treatment failures between the 6 mg Composition A and sham groups will be compared using a Ztest for independent proportions at a two-tailed alpha level of 0.05 using the Intent-to-Treat (ITT) population. Specific details of handling missing data and sensitivity analyses will be provided in the Statistical Analysis Plan which will be finalized prior to unblinding and database lock.

Figure 14:
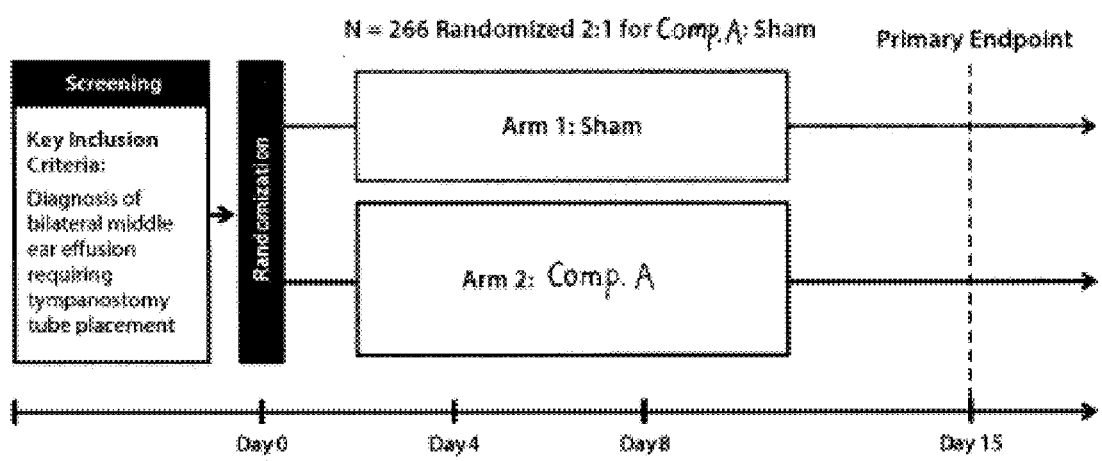
FIG. 14: Design of an exemplary clinical trial in pediatric patients (2 identical trials).

FIG. 14 schematically illustrates an exemplar clinical trial according to the present disclosure. The examplary clinical trial program consists of two identical prospective, randomized, double-blind, sham-controlled, multicenter, studies of Composition A given as a single IT injection for intraoperative treatment of middle ear effusion in pediatric patients requiring TTP surgery. As shown in FIG. 14, each trial consists of two treatment arms of Composition A as Arm 2 and no treatment (sham) as Arm 1, with patients randomized 2 to 1, respectively.

The primary endpoint of the exemplary clinical trials is the cumulative proportion of treatment failures defined as otorrhea (fluid draining through the tube) observed by a blinded assessor from Day 4 through the Day 15 visit, or use of rescue antibiotics from Day 1 through the Day 15 visit, whichever occured first. Patients ages six months to 17 years are eligible for the clinical trial if they presented with effusion (fluid) in both ears (bilateral) at the time of TTP surgery. Following randomization, patients receive either Composition A or no treatment (sham). Treatment is administered in the operating room following the myringotomy (a small incision in the ear drum) and suctioning, and before the placement of the tube. As is customary in pediatric patients, all patients are under general anesthesia for the procedure. Follow-up visits occurr on Day 4, 8, 15 and 29 after surgery.

A total of 532 pediatric patients at 60 trial sites in the United States and Canada have been enrolled across the two clinical trials designated as Study 302 and Study 303. An analysis of the baseline patient demographics data from both trials suggests reasonable balance with no notable differences between the treatment groups. All enrolled patients have completed the Day 15 study visit, except for one patient in a sham group and one patient in an Composition A group who were randomized but not treated.

Figure 15:
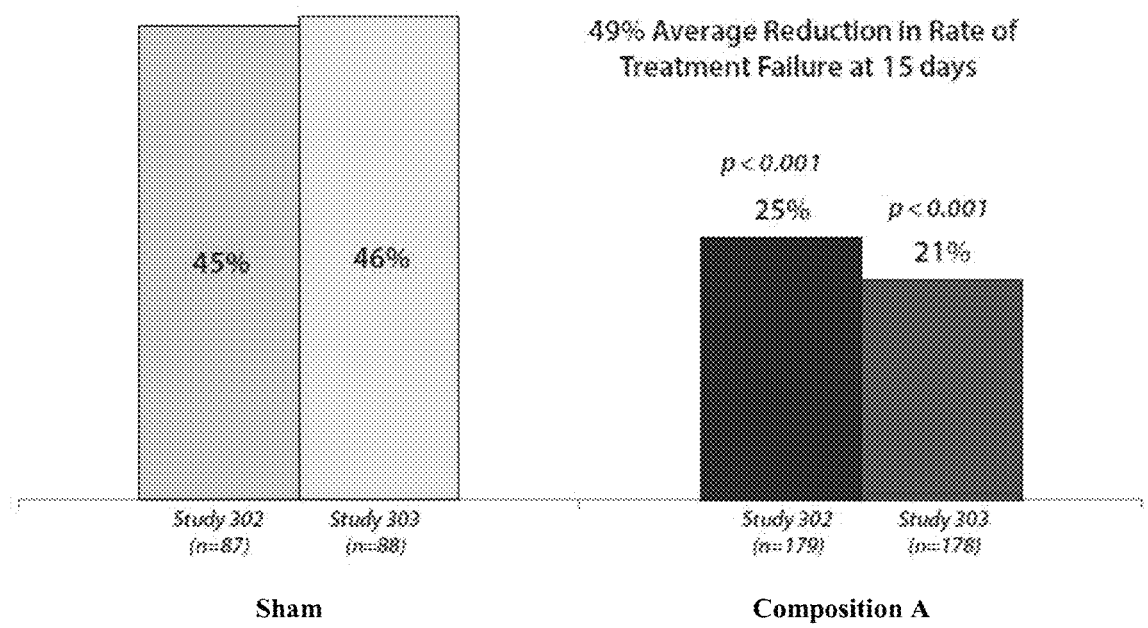
FIG. 15: Exemplary clinincal trial results: Cumulative proportion of treatment failures through Day 15 (all patients; "n" denotes sample size per group).

The exemplary clinical trial has demonstrated that Composition A achieves its primary efficacy endpoint as well as several secondary endpoints and is well tolerated. As shown in FIG. 15, Composition A has demonstrated a reduction for the primary efficacy endpoint, the incidence of treatment failures through Day 15 in all randomized patients, which averaged 49% across the two trials, in each case as compared to sham. This effect on the incidence of treatment failures is statistically significant (p<0.001) for both trials. The p-value is the probability that the reported result was achieved purely by chance (e.g., a p-value≤0.001 means that there is a 0.1% or less probability that the difference between the sham group and the treatment group is purely due to chance). A p-value≤0.05 is a commonly used criterion for statistical significance and may be supportive of a finding of efficacy by regulatory authorities.

Figure 16:
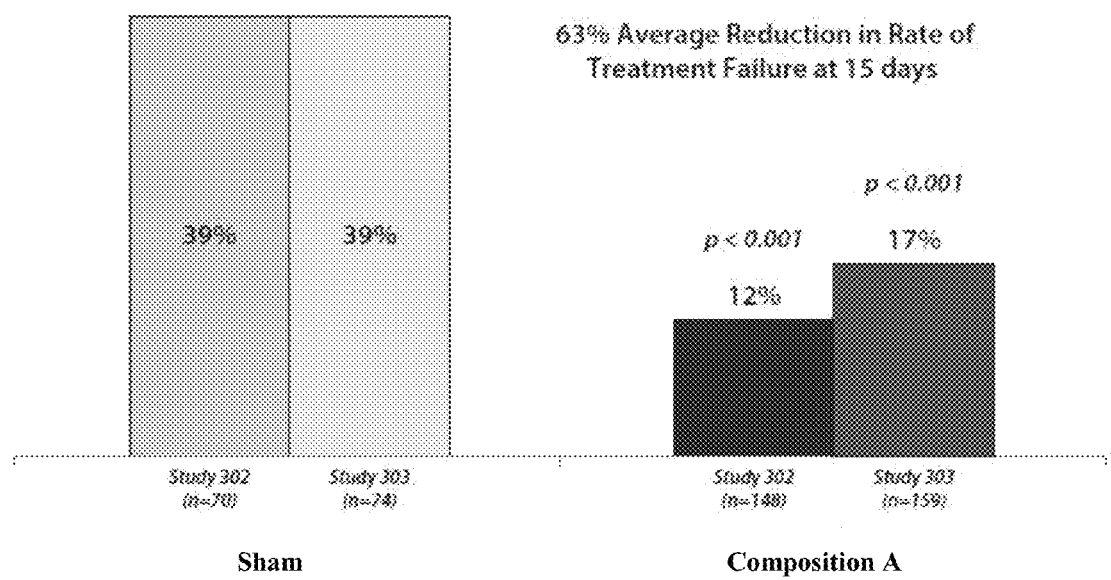
FIG. 16: Exemplary clinincal trial results: Cumulative proportion of treatment through Day 15 (per-protocol analysis; "n" denotes sample size per group).

One sensitivity analysis performed on the primary endpoint, the per-protocol analysis, evaluates the incidence of treatment failures in all enrolled patients who did not have a major protocol deviation. More than 80% of patients in each trial and treatment group qualified for this analysis. As shown in FIG. 16, Composition A provides a reduction in the rate of treatment failure through Day 15 in the per-protocol population averaging more than 60% across the two trials, in each case as compared to sham. This effect is statistically significant (p<0.001) for both trials.

Figure 17:
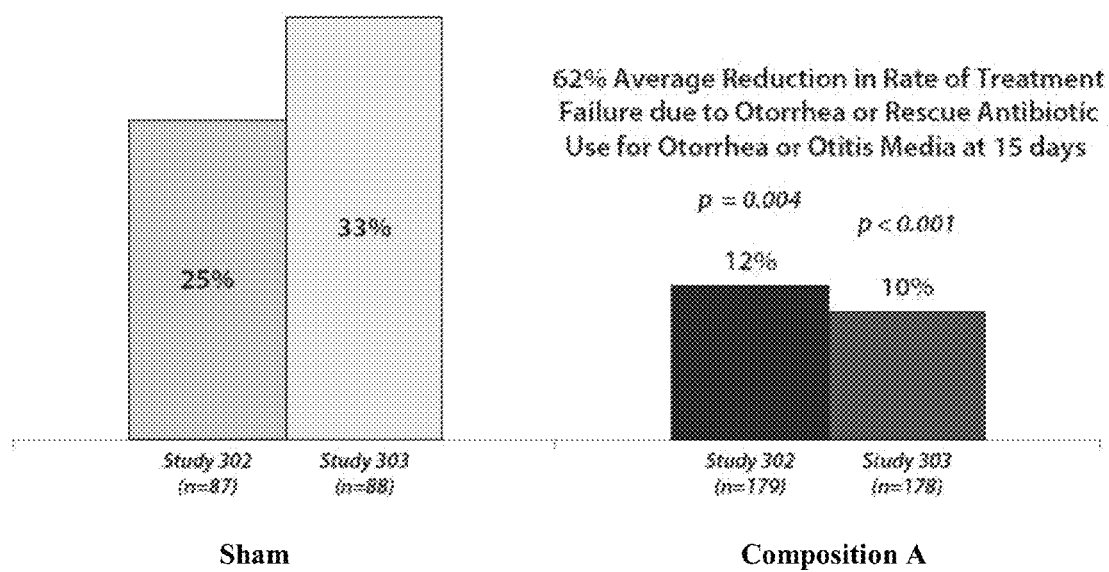
FIG. 17: Exemplary clinincal trial results: Cumulative proportion of treatment failures due to otorrhea or rescue antibiotic use for otorrhea or otitis media through Day 15 ("n" denotes sample size per group).

A post-hoc analysis has been conducted that evaluated the cumulative proportion of patients in the exemplary trials considered treatment failures due to observation of otorrhea by the blinded observer or use of either otic or systemic antibiotics with documentation of otorrhea or otitis media through Day 15. FIG. 17 presents this data for the Phase 3 trials which indicate that Composition A reduces the rate of post-operative otorrhea or use of rescue antibiotics for documented otorrhea or otitis media by more than 60% when averaged across both trials, in each case as compared to sham. This effect is statistically significant in both trials (p≤0.004).

Composition A has been well tolerated in the exemplary clinical trials. No deaths, no serious adverse events related to Composition A occurred in the exemplary clinical trial, and no subjects were discontinued due to adverse events. There were no adverse findings demonstrated on physical examination or vital signs. Most adverse events were mild or moderate in severity. Safety assessments included treatment-emergent adverse events, or TEAEs, hearing function testing and tympanometry (middle ear function). Results for TEAEs are presented in the table below. Overall, there are no observed differences between AuriPro and sham treatment. Additionally, treatment with Composition was not found to have a negative impact on hearing, tympanometry or otoscopy (general examination of the ear), and there was no increase in the incidence of tube clogging with AuriPro.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. A method of alleviating, abating or ameliorating a pediatric otic disease or condition associated with a microbial infection, the method comprising administering into the middle ear of a pediatric patient in need thereof an aqueous thermoreversible gel composition comprising about 6.0% by weight of micronized ciprofloxacin and 15-17% by weight of poloxamer 407, wherein the composition is administered to the pediatric patient through a single, intratympanic injection to each infected ear, wherein the otic disease or condition is otitis media.

2. The method of claim 1, wherein the composition comprises from about 5 mg to about 7 mg by weight of micronized ciprofloxacin.

3. The method of claim 1, wherein the composition comprises 5.4-6.6% by weight of micronized ciprofloxacin.

4. The method of claim 1, wherein the composition is free of butylated hydroxytoluene (BHT).

5. The method of claim 1, wherein the composition is preservative-free.

6. The method of claim 1, wherein the composition further comprises tromethamine.

7. The method of claim 1, wherein the composition has a pH of about 7.0 to about 8.0.

8. The method of claim 1, wherein the composition is administered following myringotomy.

9. The method of claim 8, wherein the composition is administered to the site of myringotomy of the pediatric patient.

10. The method of claim 8, wherein the composition is administered before tympanostomy tube placement.

11. The method of claim 8, wherein the composition is administered after tympanostomy tube placement.

12. The method of claim 1, wherein the pediatric otic disease or condition is otitis media with effusion.

13. The method of claim 1, wherein the pediatric otic disease or condition is bilateral middle ear effusion.

14. The method of claim 1, wherein the pediatric patient is 6 months to 12 years old.

15. The method of claim 1, wherein the pediatric patient is 6 months to 2 years old.

16. The method of claim 1, wherein the pediatric patient is 2 years to 12 years old.

17. The method of claim 1, wherein the pediatric otic disease or condition is associated with a bacterial infection.

18. The method of claim 17, wherein the bacterial infection is associated with *Escherichia coli, Klebsiella pneumoniae, Enterobacter cloacae, Proteus mirabilis, Proteus rettgeri, Proteus vulgaris, Proteus morgani, Providencia stuartii, Morganella morganii, Citrobacter freundii, Pseudomonas aeruginosa, Staphylococcus aureus, Staphylococcus epidermidis, Streptococcus pyogenes, Streptococcus pneumoniae, Streptococcus faecalis, Alcaligenes faecalis, Klebsiella aerogenes, Klebsiella pneumonia, Haemophilus influenzae, Moraxella catarrhalis*, or a combination thereof.

* * * * *